US005872231A

United States Patent [19]

Engvall et al.

[11] Patent Number: 5,872,231
[45] Date of Patent: Feb. 16, 1999

[54] NUCLEIC ACIDS ENCODING MEROSIN

[75] Inventors: Eva Engvall, Escondido, Calif.; Ilmo Leivo, Helsinki, Finland

[73] Assignee: La Jolla Cancer Research Foundation, La Jolla, Calif.

[21] Appl. No.: 125,077

[22] Filed: Sep. 22, 1993

Related U.S. Application Data

[63] Continuation-in-part of Ser. No. 919,951, Jul. 27, 1992, abandoned, which is a continuation of Ser. No. 472,319, Jan. 30, 1990, abandoned.

[51] Int. Cl.[6] .......................... C07H 21/02; C07H 19/00; C12P 21/06; C12N 15/00
[52] U.S. Cl. ...................... 536/23.1; 536/22.1; 536/23.5; 435/69.1; 435/69.3; 435/320.1
[58] Field of Search .......................... 536/34, 22.1, 23.1, 536/23.5, 24.3, 24.31; 435/91.6, 320.1, 69.1, 71.1, 71.2, 91, 69.3; 530/350

[56] References Cited

U.S. PATENT DOCUMENTS

| 5,444,158 | 8/1995 | Engvall et al. ........................ 590/395 |

FOREIGN PATENT DOCUMENTS

| 204 302 | 3/1986 | European Pat. Off. ........ C12N 15/00 |
| 5011462 | 8/1991 | WIPO ............................ C07K 13/00 |
| WO 91/11462 | 8/1991 | WIPO ............................ C07K 13/00 |

OTHER PUBLICATIONS

Rudinger, J., Peptide Hormones, ed. J.A. Parsons, Jun. 1976, pp. 1–7.

Cornbrooks et al., "In vivo and in vitro observations on laminin production by Schwann cells," *Proc. Natl. Acad. Sci. USA* 80:3850–3854 (1983).

Davis et al., "Isolation and characterization of rat Schwannoma neurite–promoting factor: evidence that the factor contains laminin," *J. Neurosci.* 5:2662–2671 (1985).

Deutzmann et al., "Structural study of long arm fragments of laminin: evidence for repetitive C–terminal sequences in the A–chain, not present in the B–chains," *Eur. J. Biochem.* 177:35–45 (1988).

Edgar et al., "Structural requirements for the stimulation of neurite outgrowth by two variants of laminin and their inhibition by antibodies," *J. Cell. Biol.* 106:1299–1306 (1988).

Ehrig et al., "Merosin, a tissue–specific basement membrane protein, is a laminin–like protein", *Proc. Natl. Acad. Sci. USA* 87:3264–3268 (1990).

Engvall et al., "Distribution and isolation of four laminin variants: tissues restricted distribution of heterotrimers assembled from five different subunits," *Cell. Regul.* 1(10):731–740 (1990).

Engvall et al., "Merosin is a tissue–restricted basement membrane component and a member of a family of laminin like protein," *J. Cell. Biol.* 109:4 part 2 (1989), (New York US), Twenty–Ninth Annual Meeting of the American Society for Cell Biology, Houston, TX, 5–9 Nov. 1989, Mini-symposium 1, Abstract 3.

Engvall et al., "Merosin promotes cell attachment and neurite outgrowth and is a component of the neurite–promoting factor of RN22 Schwannoma cells," *E. Cell. Res.* 198:115–123 (1992).

Hagg et al., "Merosin is associated with neurons of the adult mammalian central nervous system," *J. Cell. Biol.* 111, 5 part 2 (1990), Abstract 2227.

Hassell et al., "Isolation of two forms of basement membrane proteoglycans," *J. Biol. Chem.* 260:8098–8105 (1984).

Hunter et al., "A laminin–like adhesive protein concentrated in the synaptic cleft of the neuromuscular junction," *Nature* 338:229–233 (1989).

Lander et al., "Laminin is associated with the neurite outgrowth–promoting factors found in conditioned media," *Proc. Natl. Acad. Sci. USA* 82:2183–2187 (1985).

Leivo et al., "Distribution of merosin, a laminin–related, tissue–specific basement membrane protein, in human schwann cell neoplasms," *Laboratory Invest.* 61:426–432 (1989).

Leivo et al., "Merosin, a protein specific for basement membranes of Schwann cells, striated muscle, and trophoblast, is expressed late in nerve and muscle development," *Proc. Natl. Acad. Sci. USA* 85:1544–1548 (1988).

Manthorpe et al., "A dissection of tissue culture," *Manual of the Nervous System*, pp. 322–326 (1989).

Martin and Timpl, "Laminin and other basement membrane components," *Ann. Rev. Cell. Biol.* 3:57–85 (1987).

Ohno et al., "Isolation of laminin from human placental basement membranes: amnion, chorion and chorionic microvessels", *Biochem. Biophys. Res. Commun.* 112(3):1091–1098 (1983).

Paulsson and Saladin, "Mouse heart laminin," *J. Biol. Chem.* 264:18726–18732 (1989).

Sandrock and Matthew, "Identification of a peripheral nerve neurite growth–promoting activity by development and use of an in vitro bioassay," *Proc. Natl. Acad. Sci. USA* 84:6934–6938 (1987).

(List continued on next page.)

*Primary Examiner*—Susan A. Loring
*Attorney, Agent, or Firm*—Campbell & Flores LLP

[57] ABSTRACT

This invention provides an isolated nucleic acid molecule encoding a subunit of a protein, the protein having an apparent molecular weight of about 800 kD, designated merosin. Also provided are isolated nucleic acid molecules which encode merosin fragments. Anti–merosin antibodies, vectors for the recombinant production of merosin, and the expression of recombinant proteins by use of a host vector system also are provided. The invention further provides the use of merosin to promote neurite growth and for certain diagnostic applications.

29 Claims, 30 Drawing Sheets

OTHER PUBLICATIONS

Steele and Hoffman, "Neurite–promoting activity from fetal skeletal muscle: partial purification of a high–molecular––weight form," *J. Neurosci. Res.* 15:323–339 (1986).

Terranova et al., "Laminin promotes rabbit neutrophil motility and attachment," *J. Clin. Invest.* 77:1180–1186 (1986).

Palm and Furcht, "Production of Laminin and Fibronectin by Schwannoma Cells: Cell–Protein Interactions In Vitro and Protein Localization in Peripheral Nerve In Vivo" *J. Cell Biol.* 96:1218–1226 (1983).

Hayashi and Miki, "Purification and Characterization of a Neurite Outgrowth Factor from Chicken Gizzard Smooth Muscle" *J. Biol. Chem.* 260:14269–14278 (1985).

Wewer et al., "Human Laminin Isolated in a Nearly Intact, Biologically Active Form from Placenta by Limited Proteolysis" *J. Biol. Chem.* 258:12654–12660 (1983).

Paulsson et al., "Structure of Laminin Variants—The 300–kDa chains of murine and bovine heart laminin are related to the human placenta merosin heavy chain and replace the A chain in some laminin variants" *J. Biol. Chem.* 266:17545–17551 (1991).

Ohno et al., "Laminin M is found in placental basement membranes, but not in basement membranes of neoplastic origin" *Conn. Tissue Res.* 15:199–207 (1986).

Ehrig et al Proc. Natl. Acad. Science May, .87:3264–3268, 1990.

Leivo et al Ontogenez vol. 20 pp. 461–470, 1989 (Translation).

Ehrig et al, Annals of the NYA of S, 2nd NYA of S conf on Collagen, 1989, pp. 276–280.

Maniates et al pp. 98–106, chapter 6, and pp. 224–246 Moleculer Cloning a Laboratory Manual 1982, Cold Spring Harbor.

Ehrig et al PNAS 87:3264–3268, 1990.

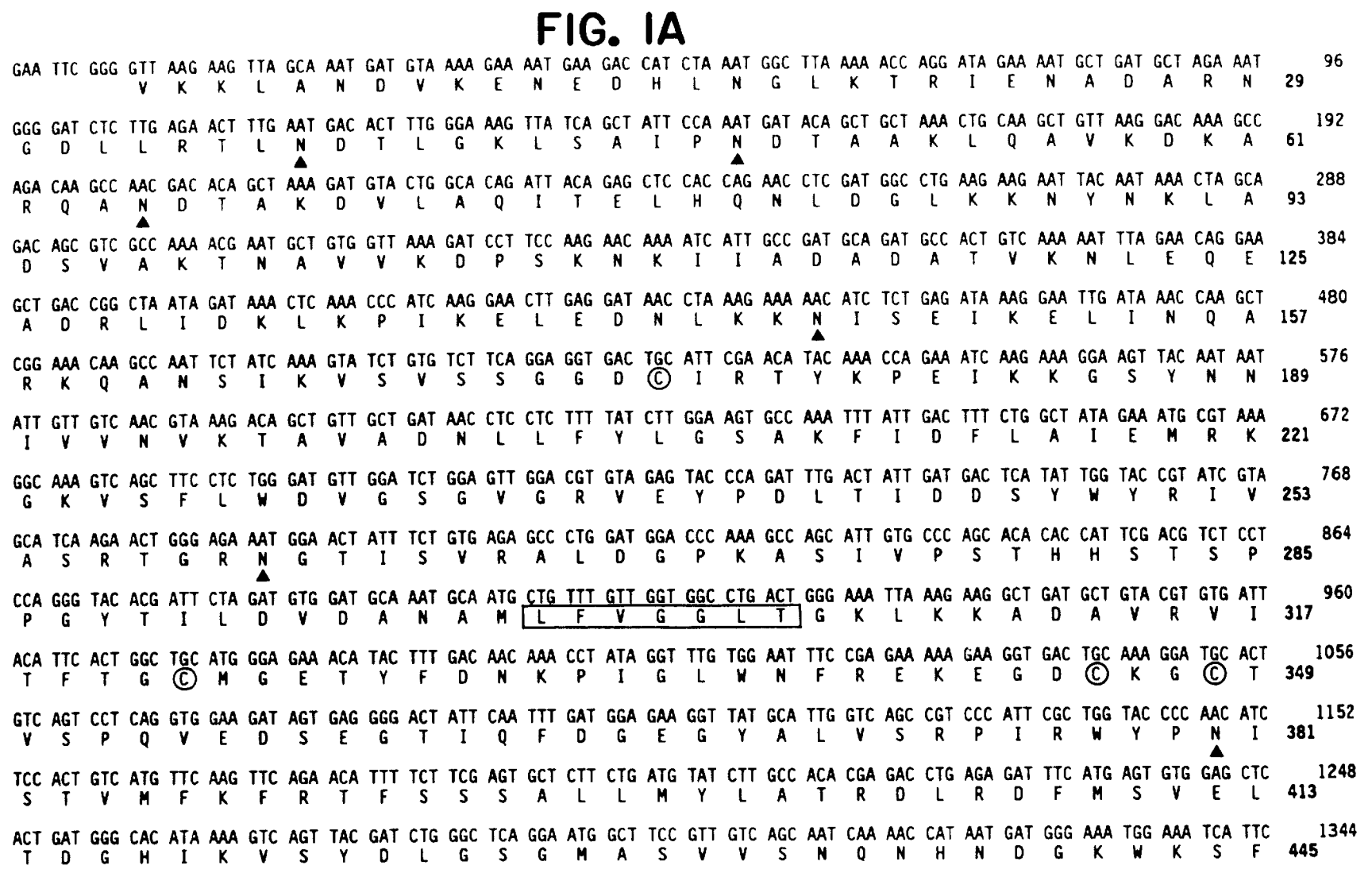

```
AAA AAA GCC GAC ATC CTG GAT GTC GTG GGA ATG CTG TAT GTT GGT GGG TTA CCC ATC AAC TAC ACT ACC CGA AGA ATT GGT CCA GTG ACC TAT AGC      2784
 K   K   A   D   I   L   D   V   V   G   M   L   Y   V   G   G   L   P   I   N   Y   T   T   R   R   I   G   P   V   T   Y   S       925

ATT GAT GGC GTC AGG AAT CTC CAC ATG GCA GAG GCC CCT GCC GAT CTG GAA CAA ACC CCC AGC TCC AGC TTC CAT GTT GGG ACA TGT TTT GCA AAT      2880
 I   D   G   V   R   N   L   H   M   A   E   A   P   A   D   L   E   Q   T   P   S   S   S   F   H   V   G   T   C   F   A   N       957

GCT CAG AGG ACA GGA ACA TAT TTT GAC CTC ACA GAC GTC GAT GGG TTT GCC AAA GCA GTT GGT GGA TTG GAC CTT GTA GAA TTT GAA TTC CGC          2976
 A   Q   R   T   G   T   Y   F   D   L   T   D   V   D   G   F   A   K   A   V   G   G   L   D   L   V   E   F   E   F   R           989

ACA ACT ACA ACG ACT GGA GTT GGA ATC GCT GCT CGG GAT GGG ATG GAT GGA ATT GAT GAA AAG TTG ATG TTT CAT GTG                              3072
 T   T   T   T   T   G   V   G   I   S   S   Q   K   M   D   G   M   D   G   I   D   E   K   L   M   F   H   V                      1021

GAC AAT CGC CGG GCG ATT GAT GCT GTC ACT GCT GGG CAG GGG CAT TTG TGT CCA GTT GGG CAA AGC CCA GAA GTC AAA AAC AAC ATC                  3168
 D   N   R   R   A   I   D   A   V   T   A   G   Q   G   H   L   C   P   V   G   Q   S   P   E   V   K   N   K   I                  1053

AAA CAC CGC ATT GAG CTC ACA GTC GAT GGG AAC CAG GTG GAA GCC ACC AGT ATT CCG TTC CGA GGT TGC ATC AGA TCC CTG AAG CTC ACC AAA GGC GTG TTT  3264
 K   H   R   I   E   L   T   V   D   G   N   Q   V   E   A   T   S   I   P   F   R   G   C   I   R   S   L   K   L   T   K   G   V   F  1085

GTT GGA TTC CCA AGG CAG TTT GGC CTA ACA CTT ACA ATC CGA GGT TGC ATC AGA TCC CTG AAG CTC ACC AAA GGC ACA                              3360
 V   G   F   P   R   Q   F   G   L   T   L   T   I   R   G   C   I   R   S   L   K   L   T   K   G   T                              1117

GCA AGC CAC TGG AGG TTG CCA AGG CCC TGG AAC TGA GCG GCG TTC AAC CTG TAT CAT GCC CAG CCA CAT AAT AAA AAT AAG TGT AAC CCC             3456
 A   S   H   W   R   L   P   R   P   W   N   *

AGG AAG AGT CTG TCA AAA GTA TAT CAA ACA CAA AAA CAA ACA ATA TTT TAC CTA TAT ATG TTA ATT AAA CTA ATT TGT GCA TGT GTA ACA TAG AAT      3552
TC                                                                                                                                    3554
```

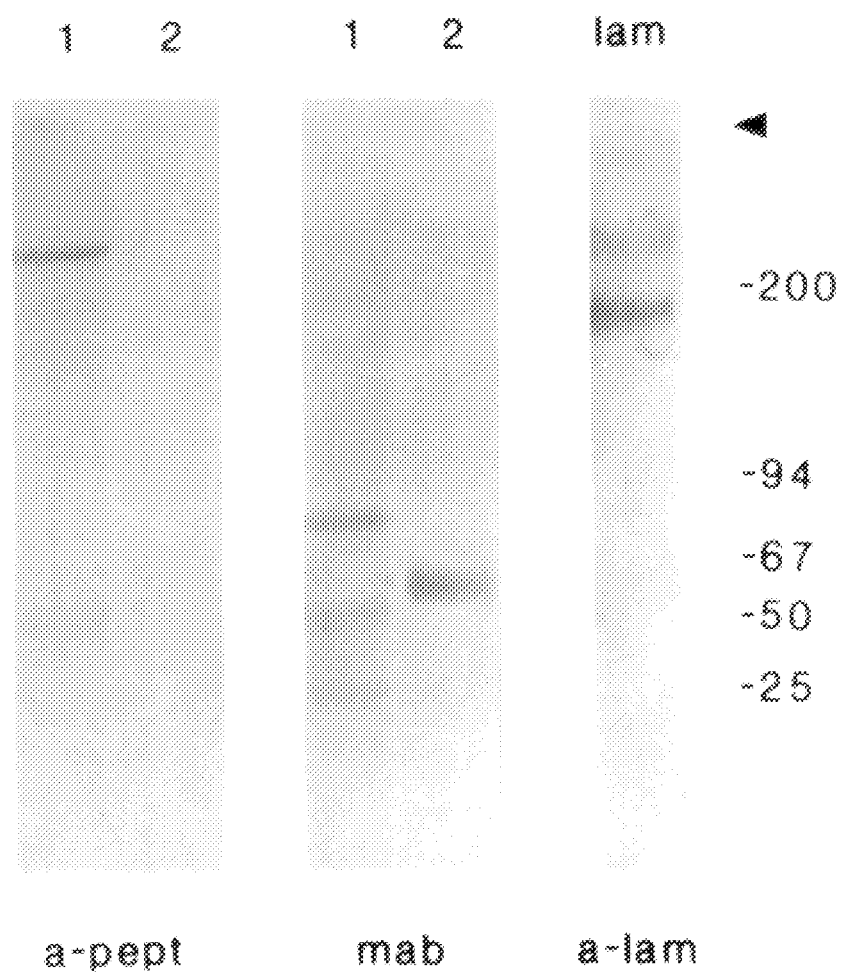

```
  1                                    CAGCGACTCCTCTGGCTCCCGAGAAGTGGATCCGGTCGCGGCCACTACG
 50  ATGCCGGGAGCCGCCGGGGTCCTCCTCCTTCTGCTGCTCTCCGGAGGCCTCGGGGGCGTACAGGCGCAGCGGCCG
  1   M  P  G  A  A  G  V  L  L  L  L  L  L  S  G  G  L  G  G  V  Q  A  Q  R  P
                                                                      △
     CAGCAGCAGCGGCAGTCACAGGCACATCAGCAAAGAGGTTTATTCCCTGCTGTCCTGAATCTTGCTTCTAATGCT
      Q  Q  Q  R  Q  S  Q  A  H  Q  Q  R  G  L  F  P  A  V  L  N  L  A  S  N  A
200  CTTATCACGACCAATGCAACATGTGGAGAAAAAGGACCTGAAATGTACTGCAAATTGGTAGAACATGTCCCTGGG
 51   L  I  T  T [N  A  T]ⓒ  G  E  K  G  P  E  M  Y ⓒ  K  L  V  E  H  V  P  G
     CAGCCTGTGAGGAACCCGCAGTGTCGAATCTGCAATCAAAACAGCAGCAATCCAAACCAGAGACACCCGATTACA
      Q  P  V  R  N  P  Qⓒ  R  I ⓒ  N  Q [N  S  S] N  P  N  Q  R  H  P  I  T
350  AATGCTATTGATGGAAAGAACACTTGGTGGCAGAGTCCCAGTATTAAGAATGGAATCGAATACCATTATGTGACA
101   N  A  I  D  G  K  N  T  W  W  Q  S  P  S  I  K  N  G  I  E  Y  H  Y  V  T
     ATTACACTGGATTTACAGCAGGTGTTCCAGATCGCGTATGTGATTGTGAAGGCAGCTAACTCCCCCCGGCCTGGA
      I  T  L  D  L  Q  Q  V  F  Q  I  A  Y  V  I  V  K  A  A  N  S  P  R  P  G
500  AACTGGATTTTGGAACGCTCTCTTGATGATGTTGAATACAAGCCCTGGCAGTATCATGCTGTGACAGACACGGAG
151   N  W  I  L  E  R  S  L  D  D  V  E  Y  K  P  W  Q  Y  H  A  V  T  D  T  E
     TGCCTAACGCTTTACAATATTTATCCCCGCACTGGGCCACCGTCATATGCCAAAGATGATGAGGTCATCTGCACT
     ⓒ  L  T  L  Y  N  I  Y  P  R  T  G  P  P  S  Y  A  K  D  D  E  V  I ⓒ  T
650  TCATTTTACTCCAAGATACACCCCTTAGAAAATGGAGAGATTCACATCTCTTTAATCAATGGGAGACCAAGTGCC
201   S  F  Y  S  K  I  H  P  L  E  N  G  E  I  H  I  S  L  I  N  G  R  P  S  A
     GATGATCCTTCTCCAGAACTGCTAGAATTTACCTCCGCTCGCTATATTCGCCTGAGATTTCAGAGGATCCGCACA
      D  D  P  S  P  E  L  L  E  F  T  S  A  R  Y  I  R  L  R  F  Q  R  I  R  T
800  CTGAATGCTGACTTGATGATGTTTGCTCACAAAGACCCAAGAGAAATTGACCCCATTGTCACCAGAAGATATTAC
251   L  N  A  D  L  M  M  F  A  H  K  D  P  R  E  I  D  P  I  V  T  R  R  Y  Y
     TACTCGGTCAAGGATATTTCAGTTGGAGGGATGTGCATCTGCTATGGTCATGCCAGGGCTTGTCCACTTGATCCA
      Y  S  V  K  D  I  S  V  G  G  Mⓒ  I ⓒ  Y  G  H  A  R  A ⓒ  P  L  D  P
950  GCGACAAATAAATCTCGCTGTGAGTGTGAGCATAACACATGTGGCGATAGCTGTGATCAGTGCTGTCCAGGATTC
301   A  T [N  K  S] R ⓒ  E ⓒ  E  H  N  T ⓒ  G  D  S ⓒ  D  Q ⓒⓒ  P  G  F
     CATCAGAAACCCTGGAGAGCTGGAACTTTTCTAACTAAAACTGAATGTGAAGCATGCAATTGTCATGGAAAAGCT
      H  Q  K  P  W  R  A  G  T  F  L  T  K  T  E ⓒ  E  A ⓒ  N ⓒ  H  G  K  A
1100 GAAGAATGCTATTATGATGAAAATGTTGCCAGAAGAAATCTGAGTTTGAATATACGTGGAAAGTACATTGGAGGG
351   E  E ⓒ  Y  Y  D  E  N  V  A  R  R [N  L  S] L  N  I  R  G  K  Y  I  G  G
     GGTGTCTGCATTAATTGTACCCAAAACACTGCTGGTATAAACTGCGAGACATGTACAGATGGCTTCTTCAGACCC
      G  V ⓒ  I [N ⓒ  T] Q  N  T  A  G  I  N ⓒ  E  T ⓒ  T  D  G  F  F  R  P
1250 AAAGGGGTATCTCCAAATTATCCAAGGCCATGCCAGCCATGTCATTGCGATCCAATTGGTTCCTTAAATGAAGTC
401   K  G  V  S  P  N  Y  P  R  P ⓒ  Q  P ⓒ  H ⓒ  D  P  I  G  S  L  N  E  V
     TGTGTCAAGGATGAGAAACATGCTCGACGAGGTTTGGCACCTGGATCCTGTCATTGCAAAACTGGTTTTGCAGGT
     ⓒ  V  K  D  E  K  H  A  R  R  G  L  A  P  G  S ⓒ  H ⓒ  K  T  G  F  G  G
1400 GTGAGCTGTGATCGGTGTGCCAGGGGCTACACTGGCTACCCGGACTGCAAAGCCTGTAACTGCAGTGGGTTAGGG
451   V  S ⓒ  D  R ⓒ  A  R  G  Y  T  G  Y  P  D ⓒ  K  A ⓒ [N ⓒ  S] G  L  G
     AGCAAAAATGAGGATCCTTGTTTTGGCCCCTGTATCTGCAAGGAAAATGTTGAAGGAGGAGACTGTAGTCGTTGC
      S  K  N  E  D  P ⓒ  F  G  P ⓒ  I ⓒ  K  E  N  V  E  G  G  D ⓒ  S  R ⓒ
1550 AAATCCGGCTTCTTCAATTTGCAAGAGGATAATTGGAAAGGCTGCGATGAGTGTTTCTGTTCAGGGGTTTCAAAC
501   K  S  G  F  F  N  L  Q  E  D  N  W  K  G ⓒ  D  E ⓒ  F ⓒ  S  G  V  S  N
     AGATGTCAGAGTTCCTACTGGACCTATGGCAAAATACAAGATATGAGTGGCTGGTATCTGACTGACCTTCCTGGC
      R ⓒ  Q  S  S  Y  W  T  Y  G  K  I  Q  D  M  S  G  W  Y  L  T  D  L  P  G
1700 CGCATTCGAGTGGCTCCCCAGCAGGACGACTTGGACTCACCTCAGCAGATCAGCATCAGTAACGCGGAGGCCCGG
551   R  I  R  V  A  P  Q  Q  D  D  L  D  S  P  Q  Q  I  S  I  S  N  A  E  A  R
     CAAGCCCTGCCGCACAGCTACTACTGGAGCGCGCCGGCTCCCTATCTGGGAAACAAACTCCCAGCAGTAGGAGGA
      Q  A  L  P  H  S  Y  Y  W  S  A  P  A  P  Y  L  G  N  K  L  P  A  V  G  G
```

FIG. 6A

```
1850  CAGTTGACATTTACCATATCATATGACCTTGAAGAAGAGGAAGAAGATACAGAACGTGTTCTCCAGCTTATGATT
 601    Q   L   T   F   T   I   S   Y   D   L   E   E   E   E   E   D   T   E   R   V   L   Q   L   M   I

ATCTTAGAGGGTAATGACTTGAGCATCAGCACAGCCCAAGATGAGGTGTACCTGCACCCATCTGAAGAACATACT
        I   L   E   G   N   D   L   S   I   S   T   A   Q   D   E   V   Y   L   H   P   S   E   E   H   T

2000  AATGTATTGTTACTTAAAGAAGAATCATTTACCATACATGGCACACATTTTCCAGTCCGTAGAAAGGAATTTATG
 651    N   V   L   L   L   K   E   E   S   F   T   I   H   G   T   H   F   P   V   R   R   K   E   F   M

ACAGTGCTTGCGAATTTGAAGAGAGTCCTCCTACAAATCACATACAGCTTTGGGATGGATGCCATCTTCAGGTTG
        T   V   L   A   N   L   K   R   V   L   L   Q   I   T   Y   S   F   G   M   D   A   I   F   R   L

2150  AGCTCTGTTAACCTTGAATCCGCTGTCTCCTATCCTACTGATGGAAGCATTGCAGCAGCTGTAGAAGTGTGTCAG
 701    S   S   V   N   L   E   S   A   V   S   Y   P   T   D   G   S   I   A   A   A   V   E   V  Ⓒ   Q

TGCCCACCAGGGTATACTGGCTCCTCTTGTGAATCTTGTTGGCCTAGGCACAGGCGAGTTAACGGCACTATTTTT
       Ⓒ   P   P   G   Y   T   G   S   S  Ⓒ   E   S  Ⓒ   W   P   R   H   R   R   V  [N   G   T]  I   F

2300  GGTGGCATCTGTGAGCCATGTCAGTGCTTTGGTCATGCGGAGTCCTGTGATGACGTCACTGGAGAATGCCTGAAC
 751    G   G   I  Ⓒ   E   P  Ⓒ   Q  Ⓒ   F   G   H   A   E   S  Ⓒ   D   D   V   T   G   E  Ⓒ   L   N

TGTAAGGATCACACAGGTGGCCCATATTGTGATAAATGTCTTCCTGGTTTCTATGGCGAGCCTACTAAAGGAACC
       Ⓒ   K   D   H   T   G   G   P   Y  Ⓒ   D   K  Ⓒ   L   P   G   F   Y   G   E   P   T   K   G   T

2450  TCTGAAGACTGTCAACCCTGTGCCTGTCCACTCAATATCCCATCCAATAACTTTAGCCCAACGTGCCATTTAGAC
 801    S   E   D  Ⓒ   Q   P  Ⓒ   A  Ⓒ   P   L   N   I   P   S   N   N   F   S   P   T  Ⓒ   H   L   D

CGGAGTCTTGGATTGATCTGTGATGGATGCCCTGTCGGGTACACAGGACCACGCTGTGAGAGGTGTGCAGAAGGC
        R   S   L   G   L   I  Ⓒ   D   G  Ⓒ   P   V   G   Y   T   G   P   R  Ⓒ   E   R  Ⓒ   A   E   G

2600  TATTTTGGACAACCCTCTGTACCTGGAGGATCATGTCAGCCATGCCAATGCAATGACAACCTTGACTTCTCCATC
 851    Y   F   G   Q   P   S   V   P   G   G   S  Ⓒ   Q   P  Ⓒ   Q  Ⓒ   N   D   N   L   D   F   S   I

CCTGGCAGCTGTGACAGCTTGTCTGGCTCCTGTCTGATATGTAAACCAGGTACAACAGGCCGGTACTGTGAGCTC
        P   G   S  Ⓒ   D   S   L   S   G   S  Ⓒ   L   I  Ⓒ   K   P   G   T   T   G   R   Y  Ⓒ   E   L

2750  TGTGCTGATGGATATTTTGGAGATGCAGTTGATGCGAAGAACTGTCAGCCCTGTCGCTGTAATGCCGGTGGCTCT
 901   Ⓒ   A   D   G   Y   F   G   D   A   V   D   A   K   N  Ⓒ   Q   P  Ⓒ   R  Ⓒ   N   A   G   G   S

TTCTCTGAGGTTTGCCACAGTCAAACTGGACAGTGTGAGTGCAGAGCCAACGTTCAGGGTCAGAGATGTGACAAA
        F   S   E   V  Ⓒ   H   S   Q   T   G   Q  Ⓒ   E  Ⓒ   R   A   N   V   Q   G   Q   R  Ⓒ   D   K

2900  TGCAAGGCTGGGACCTTTGGCCTACAATCAGCAAGGGGCTGTGTTCCCTGCAACTGCAATTCTTTTGGGTCTAAG
 951   Ⓒ   K   A   G   T   F   G   L   Q   S   A   R   G  Ⓒ   V   P  Ⓒ   N  Ⓒ   N   S   F   G   S   K

TCATTCGACTGTGAAGAGAGTGGACAATGTTGGTGCCAACCTGGAGTCACAGGGAAGAAATGTGACCGCTGTGCC
        S   F   D  Ⓒ   E   E   S   G   Q  Ⓒ   W  Ⓒ   Q   P   G   V   T   G   K   K  Ⓒ   D   R  Ⓒ   A

3050  CACGGCTATTTCAACTTCCAAGAAGGAGGCTGCACAGCTTGTGAATGTTCTCATCTGGGTAATAATTGTGACCCA
1001    H   G   Y   F   N   F   Q   E   G   G  Ⓒ   T   A  Ⓒ   E  Ⓒ   S   H   L   G   N   N  Ⓒ   D   P

AAGACTGGGCGATGCATTTGCCCACCCAATACCATTGGAGAGAAATGTTCTAAATGTGCACCCAATACCTGGGGC
        K   T   G   R  Ⓒ   I  Ⓒ   P   P   N   T   I   G   E   K  Ⓒ   S   K  Ⓒ   A   P   N   T   W   G

3200  CACAGCATTACCACTGGTTGTAAGGCTTGTAACTGCAGCACAGTGGGATCCTTGGATTTCCAATGCAATGTAAAT
1051    H   S   I   T   T   G  Ⓒ   K   A  Ⓒ  [N  Ⓒ   S]  T   V   G   S   L   D   F   Q  Ⓒ   N   V   N

ACAGGCCAATGCAACTGTCATCCAAAATTCTCTGGTGCAAAATGTACAGAGTGCAGTCGAGGTCACTGGAACTAC
        T   G   Q  Ⓒ   N  Ⓒ   H   P   K   F   S   G   A   K  Ⓒ   T   E  Ⓒ   S   R   G   H   W   N   Y

3350  CCTCGCTGCAATCTCTGTGACTGCTTCCTCCCTGGGACAGATGCCACAACCTGTGATTCAGAGACTAAAAAATGC
1101    P   R  Ⓒ   N   L  Ⓒ   D  Ⓒ   F   L   P   G   T   D   A   T   T  Ⓒ   D   S   E   T   K   K  Ⓒ

TCCTGTAGTGATCAAACTGGGCAGTGCACTTGTAAGGTGAATGTGGAAGGCATCCACTGTGACAGATGCCGGCCT
        S  Ⓒ   S   D   Q   T   G   Q  Ⓒ   T  Ⓒ   K   V   N   V   E   G   I   H  Ⓒ   D   R  Ⓒ   R   P

3500  GGCAAATTCGGACTCGATGCCAAGAATCCACTTGGCTGCAGCAGCTGCTATTGCTTCGGCACTACTACCCAGTGC
1151    G   K   F   G   L   D   A   K   N   P   L   G  Ⓒ   S   S  Ⓒ   Y  Ⓒ   F   G   T   T   T   Q  Ⓒ

TCTGAAGCAAAAGGACTGATCCGGACGTGGGTGACTCTGAAGGCTGAGCAGACCATTCTACCCCTGGTAGATGAG
        S   E   A   K   G   L   I   R   T   W   V   T   L   K   A   E   Q   T   I   L   P   L   V   D   E
```

FIG. 6B

```
3650 GCTCTGCAGCACACGACCACCAAGGGCATTGTTTTTCAACATCCAGAGATTGTTGCCCACATGGACCTGATGAGA
1201  A  L  Q  H  T  T  T  K  G  I  V  F  Q  H  P  E  I  V  A  H  M  D  L  M  R
      GAAGATCTCCATTTGGAACCTTTTTATTGGAAACTTCCAGAACAATTTGAAGGAAAGAAGTTGATGGCCTATGGG
       E  D  L  H  L  E  P  F  Y  W  K  L  P  E  Q  F  E  G  K  K  L  M  A  Y  G
3800  GGCAAACTCAAGTATGCAATCTATTTCGAGGCTCGGGAAGAAACAGGTTTCTCTACATATAATCCTCAAGTGATC
1251  G  K  L  K  Y  A  I  Y  F  E  A  R  E  E  T  G  F  S  T  Y  N  P  Q  V  I
      ATTCGAGGTGGGACACCTACTCATGCTAGAATTATCGTCAGGCATATGGCTGCTCCTCTGATTGGCCAATTGACA
       I  R  G  G  T  P  T  H  A  R  I  I  V  R  H  M  A  A  P  L  I  G  Q  L  T
3950  AGGCATGAAATTGAAATGACAGAGAAAGAATGGAAATATTATGGGGATGATCCTCGAGTCCATAGAACTGTGACC
1301  R  H  E  I  E  M  T  E  K  E  W  K  Y  Y  G  D  D  P  R  V  H  R  T  V  T
      CGAGAAGACTTCTTGGATATACTATATGATATTCATTACATTCTTATCAAAGCTACTTATGGAAATTTCATGCGA
       R  E  D  F  L  D  I  L  Y  D  I  H  Y  I  L  I  K  A  T  Y  G  N  F  M  R
4100  CAAAGCAGGATTTCTGAAATCTCAATGGAGGTAGCTGAACAAGGACGTGGAACAACAATGACTCCTCCAGCTGAC
1351  Q  S  R  I  S  E  I  S  M  E  V  A  E  Q  G  R  G  T  T  M  T  P  P  A  D
      TTGATTGAAAAATGTGATTGTCCCCTGGGCTATTCTGGCCTGTCCTGTGAGGCATGCTTGCCGGATTTTATCGA
       L  I  E  K (C) D (C) P  L  G  Y  S  G  L  S (C) E  A (C) L  P  G  F  Y  R
4250  CTGCGTTCTCAACCAGGTGGCCGCACCCCTGGACCAACCCTGGGCACCTGTGTTCCATGTCAATGTAATGGACAC
1401  L  R  S  Q  P  G  G  R  T  P  G  P  T  L  G  T (C) V  P (C) Q (C) N  G  H
      AGCAGCCTGTGTGACCCTGAAACATCGATATGCCAGAATTGTCAACATCACACTGCTGGTGACTTCTGTGAACGA
       S  S  L (C) D  P  E  T  S  I (C) Q  N (C) Q  H  H  T  A  G  D  F (C) E  R
4400  TGTGCTCTTGGATACTATGGAATTGTCAAGGGATTGCCAAATGACTGTCAGCAATGTGCCTGCCCTCTGATTTCT
1451 (C) A  L  G  Y  Y  G  I  V  K  G  L  P  N  D (C) Q  Q (C) A (C) P  L  I  S
      TCCAGTAACAATTTCAGCCCCTCTTGTGTCGCAGAAGGACTTGACGACTACCGCTGCACGGCTTGTCCACGGGGA
       S  S  N  N  F  S  P  S (C) V  A  E  G  L  D  D  Y  R (C) T  A (C) P  R  G
4550  TATGAAGGCCAGTACTGTGAAAGGTGTGCCCCTGGCTATACTGGCAGTCCAGGCAACCCTGGAGGCTCCTGCCAA
1501  Y  E  G  Q  Y (C) E  R (C) A  P  G  Y  T  G  S  P  G  N  P  G  G  S (C) Q
      GAATGTGAGTGTGATCCCTATGGCTCACTGCCTGTGCCCTGTGACCCTGTCACAGGATTCTGCACGTGCCGACCT
       E (C) E (C) D  P  Y  G  S  L  P  V  P (C) D  P  V  T  G  F (C) T (C) R  P
4700  GGAGCCACGGGAAGGAAGTGTGACGGCTGCAAGCACTGGCATGCACGCGAGGGCTGGGAGTGTGTTTTTTGTGGA
1551  G  A  T  G  R  K (C) D  G (C) K  H  W  H  A  R  E  G  W  E (C) V  F (C) G
      GATGAGTGCACTGGCCTTCTTCTCGGTGACTTGGCTCGCCTGGAGCAGATGGTCATGAGCATCAACCTCACTGGT
       D  E (C) T  G  L  L  L  G  D  L  A  R  L  E  Q  M  V  M  S  I [N  L  T] G
4850  CCGCTGCCTGCGCCATATAAAATGCTGTATGGTCTTGAAAATATGACTCAGGAGCTAAAGCACTTGCTGTCACCT
1601  P  L  P  A  P  Y  K  M  L  Y  G  L  E [N  M  T] Q  E  L  K  H  L  L  S  P
      CAGCGGGCCCCAGAGAGGCTTATTCAGCTGGCAGAGGGCAATCTGAATACACTCGTGACCGAAATGAACGAGCTG
       Q  R  A  P  E  R  L  I  Q  L  A  E  G  N  L  N  T  L  V  T  E  M  N  E  L
5000  CTGACCAGGGCTACCAAAGTGACAGCAGATGGCGAGCAGACCGGACAGGATGCTGAGAGGACCAACACAAGAGCA
1651  L  T  R  A  T  K  V  T  A  D  G  E  Q  T  G  Q  D  A  E  R  T  N  T  R  A
      AAGTCCCTGGGAGAATTCATTAAGGAGCTTGCCCGGGATGCAGAAGCTGTAAATGAAAAAGCTATAAAACTAAAT
       K  S  L  G  E  F  I  K  E  L  A  R  D  A  E  A  V  N  E  K  A  I  K  L [N
5150  GAAACTCTAGGAACTCGAGACGAGGCCTTTGAGAGAAATTTGGAAGGGCTTCAGAAAGAGATTGACCAGATGATT
1701   E  T] L  G  T  R  D  E  A  F  E  R  N  L  E  G  L  Q  K  E  I  D  Q  M  I
      AAAGAACTGAGGAGGAAAAATCTAGAGACACAAAAGGAAATTGCTGAAGATGAGTTGGTAGCTGCAGAAGCCCTT
       K  E  L  R  R  K  N  L  E  T  Q  K  E  I  A  E  D  E  L  V  A  A  E  A  L
5300  CTGAAAAAAGTGAAGAAGCTGTTTGGAGAGTCCCGGGGGGAAAATGAAGAAATGGAGAAGGATCTCCGGGAAAAA
1751  L  K  K  V  K  K  L  F  G  E  S  R  G  E  N  E  E  M  E  K  D  L  R  E  K
      CTGGCTGACTACAAAAACAAAGTTGATGATGCTTGGGACCTTTTGAGAGAAGCCACAGATAAAATCAGAGAAGCT
       L  A  D  Y  K  N  K  V  D  D  A  W  D  L  L  R  E  A  T  D  K  I  R  E  A
5450  AATCGCCTATTTGCAGTAAATCAGAAAAACATGACTGCATTGGAGAAAAAGAAGGAGGCTGTTGAGAGCGGCAAA
1801  N  R  L  F  A  V  N  Q  K [N  M  T] A  L  E  K  K  K  E  A  V  E  S  G  K
      CGACAAATTGAGAACACTTTAAAAGAAGGCAATGACATACTCGATGAAGCCAACCGTCTTGCAGATGAAATCAAC
       R  Q  I  E  N  T  L  K  E  G  N  D  I  L  D  E  A  N  R  L  A  D  E  I  N
```

FIG. 6C

```
5600  TCCATCATAGACTATGTTGAAGACATCCAAACTAAATTGCCACCTATGTCTGAGGAGCTTAATGATAAAATAGAT
1851    S  I  I  D  Y  V  E  D  I  Q  T  K  L  P  P  M  S  E  E  L  N  D  K  I  D
      GACCTCTCCCAAGAAATAAAGGACAGGAAGCTTGCTGAGAAGGTGTCCCAGGCTGAGAGCCACGCAGCTCAGTTG
        D  L  S  Q  E  I  K  D  R  K  L  A  E  K  V  S  Q  A  E  S  H  A  A  Q  L
5750  AATGACTCATCTGCTGTCCTTGATGGAATCCTTGATGAGGCTAAAAACATCTCCTTCAATGCCACTGCAGCCTTC
1901   [N  D  S] S  A  V  L  D  G  I  L  D  E  A  K [N  I  S] F [N  A  T] A  A  F
      AAAGCTTACAGCAATATTAAGGACTATATTGATGAAGCTGAGAAAGTTGCCAAAGAAGCCAAAGATCTTGCACAT
        K  A  Y  S  N  I  K  D  Y  I  D  E  A  E  K  V  A  K  E  A  K  D  L  A  H
5900  GAAGCTACAAAACTGGCAACAGGTCCTCGGGGTTTATTAAAGGAAGATGCCAAAGGCTGTCTTCAGAAAAGCTTC
1951    E  A  T  K  L  A  T  G  P  R  G  L  L  K  E  D  A  K  G (C) L  Q  K  S  F
      AGGATTCTTAACGAAGCCAAGAAGTTAGCAAATGATGTAAAAGAAAATGAAGACCATCTAAATGGCTTAAAAACC
        R  I  L  N  E  A  K  K  L  A  N  D  V  K  E  N  E  D  H  L  N  G  L  K  T
6050  AGGATAGAAAATGCTGATGCTAGAAATGGGGATCTCTTGAGAACTTTGAATGCACTTTGGGAAAGTTATCAGCT
2001    R  I  E  N  A  D  A  R  N  G  D  L  L  R  T  L [N  D  T] L  G  K  L  S  A
      ATTCCAAATGATACAGCTGCTAAACTGCAAGCTGTTAAGGACAAAGCCAGACAAGCCAACGACACAGCTAAAGAT
        I  P [N  D  T] A  A  K  L  Q  A  V  K  D  K  A  R  Q  A [N  D  T] A  K  D
6200  GTACTGGCACAGATTACAGAGCTCCACCAGAACCTCGATGGCCTGAAGAAGAATTACAATAAACTAGCAGACAGC
2051    V  L  A  Q  I  T  E  L  H  Q  N  L  D  G  L  K  K  N  Y  N  K  L  A  D  S
      GTCGCCAAAACGAATGCTGTGGTTAAAGATCCTTCCAAGAACAAAATCATTGCCGATGCAGATGCCACTGTCAAA
        V  A  K  T  N  A  V  V  K  D  P  S  K  N  K  I  I  A  D  A  D  A  T  V  K
6350  AATTTAGAACAGGAAGCTGACCGGCTAATAGATAAACTCAAACCCATCAAGGAACTTGAGGATAACCTAAAGAAA
2101    N  L  E  Q  E  A  D  R  L  I  D  K  L  K  P  I  K  E  L  E  D  N  L  K  K
      AACATCTCTGAGATAAAGGAATTGATAAACCAAGCTCGGAAACAAGCCAATTCTATCAAAGTATCTGTGTCTTCA
       [N  I  S] E  I  K  E  L  I  N  Q  A  R  K  Q  A  N  S  I  K  V  S  V  S  S
6500  GGAGGTGACTGCATTCGAACATACAAACCAGAAATCAAGAAAGGAAGTTACAATAATATTGTTGTCAACGTAAAG
2151    G  G  D (C) I  R  T  Y  K  P  E  I  K  K  G  S  Y  N  N  I  V  V  N  V  K
      ACAGCTGTTGCTGATAACCTCCTCTTTTATCTTGGAAGTGCCAAATTTATTGACTTTCTGGCTATAGAAATGCGT
        T  A  V  A  D  N  L  L  F  Y  L  G  S  A  K  F  I  D  F  L  A  I  E  M  R
6650  AAAGGCAAAGTCAGCTTCCTCTGGGATGTTGGATCTGGAGTTGGACGTGTAGAGTACCCAGATTTGACTATTGAT
2201    K  G  K  V  S  F  L  W  D  V  G  S  G  V  G  R  V  E  Y  P  D  L  T  I  D
      GACTCATATTGGTACCGTATCGTAGCATCAAGAACTGGGAGAAATGGAACTATTTCTGTGAGAGCCCTGGATGGA
        D  S  Y  W  Y  R  I  V  A  S  R  T  G  R [N  G  T] I  S  V  R  A  L  D  G
6800  CCCAAAGCCAGCATTGTGCCCAGCACACACCATTCGACGTCTCCTCCAGGGTACACGATTCTAGATGTGGATGCA
2251    P  K  A  S  I  V  P  S  T  H  H  S  T  S  P  P  G  Y  T  I  L  D  V  D  A
      AATGCAATGCTGTTTGTTGGTGGCCTGACTGGGAAATTAAAGAAGGCTGATGCTGTACGTGTGATTAC
        N  A  M  L  F  V  G  G  L  T  G  K  L  K  K  A  D  A  V  R  V  I  T  F  T
2301    G (C) M  G  E  T  Y  F  D  N  K  P  I  G  L  W  N  F  R  E  K  E  G  D (C)
        K  G (C) T  V  S  P  Q  V  E  D  S  E  G  T  I  Q  F  D  G  E  G  Y  A  L
2351    V  S  R  P  I  R  W  Y  P [N  I  S] T  V  M  F  K  F  R  T  F  S  S  S  A
        L  L  M  Y  L  A  T  R  D  L  R  D  F  M  S  V  E  L  T  D  G  H  I  K  V
2401    S  Y  D  L  G  S  G  M  A  S  V  V  S  N  Q  N  H  N  D  G  K  W  K  S  F
        T  L  S  R  I  Q  K  Q  A [N  I  S] I  V  D  I  D  T  N  Q  E  E  N  I  A
2451    T  S  S  S  G  N  N  F  G  L  D  L  K  A  D  D  K  I  Y  F  G  G  L  P  T
        L  R [N  L  S] M  K  A  R  P  E  V  N  L  K  K  Y  S  G (C) L  K  D  I  E
```

E G N D L S I S T A Q D E     V Y L H P S E E H T N V L L L K
     | |   | | |   : | |       | |       |   |     | |   | | :   |  IVb
     K G N G L T L S T     Q A E G L S L Q P Y E E Y L N V V R L V

W C Q P G V T G K K C D R C A H G Y F N F Q E G G C T A C E
       |     |   |   : | | : | | | | |   : :   : | : |   | | | |  IIIb
     H C V P G V A G K R C D R C A H G F Y A Y Q D G S C T P C D

```
      E D L H L E P F Y W K L P E Q F E G K K L M A Y G G K L Y
      : :     | | | | | : | |     | |   |     | | | | | | | | |  IVa
      Q H I R A E P F Y W R L P Q Q F Q G D Q L M A Y G G K L Y
```

```
1256  A I Y F E A R E E T G F S T Y N P Q V I I R G G T P T H A
      : :   |   : :       |   |   :   | | | : | : | |             :
1240  S V A F Y S L D G V G T S N F E P Q V L I K G G         R I
```

```
      R I I V R H M A A P L I G Q L T R H E I E     M T E K E W K Y
      |   |   | | |     :     |   | |         | |           | | |
      R K Q V I Y M D A P A P E N G V R Q E Q E V A M R E N F W K Y
                                                                  IVa
1314  Y G D D P R V H R T V T R E D F L D I L Y D I H Y I L I K
                :     | | | | | | |   :   : |     | |     | | | | | |
1297      F N S V S E K P V T R E D F M S V L S D I E Y I L I K
```

1432  E T S I C Q N C Q H H T A G D F C E R C A L G Y Y G I V K
            |   |   | |         | | | | : | :   | | | |   |
1415  N T G K C L N C G D N T A G D H C D V C T S G Y Y G K V T
                                                                  IIIa
      G L P N D C Q Q C A C P L I S S S N N F S P S C V A E G L D D
      |       | | |   | | |   |             : | |     | |       |
      G S A S D C A L C A C P   H S P P A S F S P T C V L E G D H D

```
B1   CFCYGHASECAPVDGFNEEVEQMVHGHCMCRHNTKGLNCELCMDP HDLPWKPAEGKNSNACKK
 S   CFCYGHASQCAPAPGAPAHAEGMVHGACICKHNTRGLNCEQCGDP GDLPWHPAEDGHTHACRK
 A   CICYGHASSCP    WDE    TTKKLQCQCEHNTCGESCNRCCPG HQQPWRPGTVSSGNTCEA
mA   CICYGHASSCP    WDE    EAKQLQCQCEHNTCGESCDRCCPG HQQPWRPGTISSGNECEE
 M   CICYGHARACP    LDP    ATNKSRCECEHNTCGDSCDQCCPG HQAPWRAGTFLTKTECEA
B2   CKCNGHASEC     MKN    EFDKLVCNCKHNTYGVDCEKCLPF NDRPWRRATAESASECLP
dA   CMCNGHADTCD    VKDPKSPVRILACRCQHRTCGIQCNECCPG EQKKWRQNTNARPFNCEP

B1   CNCNEHSISCH DMAVY        LATGNVSGGV DDCQHNTMGRHCEQCKPF QHPERDIRDPNFCER
 S   CECNGHSHSCH DMAVY        LASGNVSGGV CDCCQHNTAGRHCELCRPF RDPTKDMRDPAACRP
 A   CNCHNKAKDCY BESVAKQKKSLNTAGQFRGGG VCINCLQNTMGINCETCILG RPHKVSPYEDEPCRP
mA   CNCHNKAKDCY BSSVAKERRSLNTAGQYSGGG VCVNCSQNTTGINCETCIDQ RPHKVSPYDDHPCRP
 M   CNCHGKAEECY BENVARRNLSLNIRGKYIGGGVCINCTQNTAGINCETCTDG RPKGVSPNYPRPCQP
B2   CNCNGRSQECY DPELYRST       GNGGHCTNCQDNTDGAKCERCRENF RLG     NNEACSS
B2t  CDCNGRSRQCI DRELHRQT       GNGFRCLNCNDNTDGIHCERCKNGF RHR     ERDRCLP
dA   CNCHGHSNECK DEEVNRKGLSLDIHGHYDGGGVCQNCQHRTVGINCNKCKPK RPKGKHWNETDVCSP
```

FIG. 12-1

```
B1   CTCDPASSQNEC                              IXISYT   DPSTGLIAGG GRCELNVEGERCVCREDGYDLSSEDPPECKS
 S   CDCDPMGSQCCG                              HCHSHD   DPVLGLVSGQ GRCEEHVSTRCQGCRDSFGLSASNPPQCQR
 A   CNCDPVGSLS                                SVCIKDELBSDLENGKQPGG CPCKHSYTSEKCDRCQLS          KDYPT CVS
mA   CNCDPVGSLS                                SVCIKDDRHADLANGKWPGG CPCPNSYAGDKCDRCQPS          RGFPN CIF
 M   CHCDPIGSLN                                EVCVEDEKHAR  RGLAPGS CHCKTGPGPVSCDRCASG          TGYPD CKA
B2   CHCSPVGSLS                                TGC              DSYGR CSCRPGMGDKCDRCQPS BSLTEA       CERP
B2t  CHCNSKGSLS                                ARG              DHSGR CSCRPGPTGARCDRCLPG BHLTGA  GCTQDRELLDSN
dA   QCCRYFFSTGHCEEETGNCDCRAAPQFTSCQGCAYGYYGYPNCRECECHLMGTNGYBCG AESGQCPCKIHFAGAYCKQCABHYG     FP HCKA

B1   CACNPLGTIPGGNPCDSETGHCYCRRLYTGHCDQCLPEHWGLSHCLD       CDPP
 S   CQCNSRQTVPGGTPCDSSSGTCPCRRLVTGDSCDRCLEGHWGLSHCLL      CDPP
 A   CCGNPVGSA  SDEPCT      GPCVCKDNVEGFACDRCKPGFY        NLKEKNFRGCSE
mA   CDCPTVGSL  NEDPCI      SPCLCKKNVEGFNCDRCKPGFY        NLAEKNFEGCSE
 M   CNCEGLGSK  NEDPCF      GPCICKENVEGGDCERCKSGPP        NLQEDKWKGCPG
B2   CSCDPSGSI  DE          CNVETGRCVCRDKVEGFNCERCKPGFF   NLESSNPRGCTP
B2t  CDCDPAGIA  GP    CD    AGRCVCKPAVTGEPCDRCRSGYY       NLDGGNPEGETQ
dA   CECNRIGSITND           CNVTTGEGKGLTNFGGDNCERCRHCYF   NYP      TCSY

B1   CTCDLCGALHHGCFAESCQCSCRPHHIGRQCNEVEPGYY
 S   CTCDVGSALDPCCDEATGQCPCPHHIGRR
 A   CFC     PGV   SGVC
mA   CFC     PGV   SGVC
 M   CFC     SGV   SNRC
B2   CPC     FGH   SSVC
B2t  CFC     YGH   BASC
dA   CDCDWKGTESEIGNKOSGQCICREDPGGPRCDQCLPGPVDYRDCKP
```

FIG. 12-2

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
      ( A ) LENGTH: 3554 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 10..3400

( x i ) SEQUENCE DESCRIPTION: SEQ ID NO:1:

```
GAATTCGGG GTT AAG AAG TTA GCA AAT GAT GTA AAA GAA AAT GAA GAC        48
          Val Lys Lys Leu Ala Asn Asp Val Lys Glu Asn Glu Asp
           1               5                      10

CAT CTA AAT GGC TTA AAA ACC AGG ATA GAA AAT GCT GAT GCT AGA AAT     96
His Leu Asn Gly Leu Lys Thr Arg Ile Glu Asn Ala Asp Ala Arg Asn
         15                  20                  25

GGG GAT CTC TTG AGA ACT TTG AAT GAC ACT TTG GGA AAG TTA TCA GCT    144
Gly Asp Leu Leu Arg Thr Leu Asn Asp Thr Leu Gly Lys Leu Ser Ala
 30              35                  40                      45

ATT CCA AAT GAT ACA GCT GCT AAA CTG CAA GCT GTT AAG GAC AAA GCC    192
Ile Pro Asn Asp Thr Ala Ala Lys Leu Gln Ala Val Lys Asp Lys Ala
                 50                  55                  60

AGA CAA GCC AAC GAC ACA GCT AAA GAT GTA CTG GCA CAG ATT ACA GAG    240
Arg Gln Ala Asn Asp Thr Ala Lys Asp Val Leu Ala Gln Ile Thr Glu
             65                  70                  75

CTC CAC CAG AAC CTC GAT GGC CTG AAG AAG AAT TAC AAT AAA CTA GCA    288
Leu His Gln Asn Leu Asp Gly Leu Lys Lys Asn Tyr Asn Lys Leu Ala
         80                  85                  90

GAC AGC GTC GCC AAA ACG AAT GCT GTG GTT AAA GAT CCT TCC AAG AAC    336
Asp Ser Val Ala Lys Thr Asn Ala Val Val Lys Asp Pro Ser Lys Asn
     95                  100                 105

AAA ATC ATT GCC GAT GCA GAT GCC ACT GTC AAA AAT TTA GAA CAG GAA    384
Lys Ile Ile Ala Asp Ala Asp Ala Thr Val Lys Asn Leu Glu Gln Glu
110                 115                 120                 125

GCT GAC CGG CTA ATA GAT AAA CTC AAA CCC ATC AAG GAA CTT GAG GAT    432
Ala Asp Arg Leu Ile Asp Lys Leu Lys Pro Ile Lys Glu Leu Glu Asp
                130                 135                 140

AAC CTA AAG AAA AAC ATC TCT GAG ATA AAG GAA TTG ATA AAC CAA GCT    480
Asn Leu Lys Lys Asn Ile Ser Glu Ile Lys Glu Leu Ile Asn Gln Ala
            145                 150                 155

CGG AAA CAA GCC AAT TCT ATC AAA GTA TCT GTG TCT TCA GGA GGT GAC    528
Arg Lys Gln Ala Asn Ser Ile Lys Val Ser Val Ser Ser Gly Gly Asp
        160                 165                 170

TGC ATT CGA ACA TAC AAA CCA GAA ATC AAG AAA GGA AGT TAC AAT AAT    576
Cys Ile Arg Thr Tyr Lys Pro Glu Ile Lys Lys Gly Ser Tyr Asn Asn
    175                 180                 185

ATT GTT GTC AAC GTA AAG ACA GCT GTT GCT GAT AAC CTC CTC TTT TAT    624
Ile Val Val Asn Val Lys Thr Ala Val Ala Asp Asn Leu Leu Phe Tyr
190                 195                 200                 205

CTT GGA AGT GCC AAA TTT ATT GAC TTT CTG GCT ATA GAA ATG CGT AAA    672
Leu Gly Ser Ala Lys Phe Ile Asp Phe Leu Ala Ile Glu Met Arg Lys
                210                 215                 220

GGC AAA GTC AGC TTC CTC TGG GAT GTT GGA TCT GGA GTT GGA CGT GTA    720
Gly Lys Val Ser Phe Leu Trp Asp Val Gly Ser Gly Val Gly Arg Val
```

```
                            225                                    230                                    235
GAG  TAC  CCA  GAT  TTG  ACT  ATT  GAT  GAC  TCA  TAT  TGG  TAC  CGT  ATC  GTA      768
Glu  Tyr  Pro  Asp  Leu  Thr  Ile  Asp  Asp  Ser  Tyr  Trp  Tyr  Arg  Ile  Val
          240                      245                     250

GCA  TCA  AGA  ACT  GGG  AGA  AAT  GGA  ACT  ATT  TCT  GTG  AGA  GCC  CTG  GAT      816
Ala  Ser  Arg  Thr  Gly  Arg  Asn  Gly  Thr  Ile  Ser  Val  Arg  Ala  Leu  Asp
     255                           260                     265

GGA  CCC  AAA  GCC  AGC  ATT  GTG  CCC  AGC  ACA  CAC  CAT  TCG  ACG  TCT  CCT      864
Gly  Pro  Lys  Ala  Ser  Ile  Val  Pro  Ser  Thr  His  His  Ser  Thr  Ser  Pro
270                      275                     280                          285

CCA  GGG  TAC  ACG  ATT  CTA  GAT  GTG  GAT  GCA  AAT  GCA  ATG  CTG  TTT  GTT      912
Pro  Gly  Tyr  Thr  Ile  Leu  Asp  Val  Asp  Ala  Asn  Ala  Met  Leu  Phe  Val
                         290                     295                          300

GGT  GGC  CTG  ACT  GGG  AAA  TTA  AAG  AAG  GCT  GAT  GCT  GTA  CGT  GTG  ATT      960
Gly  Gly  Leu  Thr  Gly  Lys  Leu  Lys  Lys  Ala  Asp  Ala  Val  Arg  Val  Ile
               305                      310                     315

ACA  TTC  ACT  GGC  TGC  ATG  GGA  GAA  ACA  TAC  TTT  GAC  AAC  AAA  CCT  ATA     1008
Thr  Phe  Thr  Gly  Cys  Met  Gly  Glu  Thr  Tyr  Phe  Asp  Asn  Lys  Pro  Ile
          320                      325                     330

GGT  TTG  TGG  AAT  TTC  CGA  GAA  AAA  GAA  GGT  GAC  TGC  AAA  GGA  TGC  ACT     1056
Gly  Leu  Trp  Asn  Phe  Arg  Glu  Lys  Glu  Gly  Asp  Cys  Lys  Gly  Cys  Thr
335                      340                     345

GTC  AGT  CCT  CAG  GTG  GAA  GAT  AGT  GAG  GGG  ACT  ATT  CAA  TTT  GAT  GGA     1104
Val  Ser  Pro  Gln  Val  Glu  Asp  Ser  Glu  Gly  Thr  Ile  Gln  Phe  Asp  Gly
350                      355                     360                          365

GAA  GGT  TAT  GCA  TTG  GTC  AGC  CGT  CCC  ATT  CGC  TGG  TAC  CCC  AAC  ATC     1152
Glu  Gly  Tyr  Ala  Leu  Val  Ser  Arg  Pro  Ile  Arg  Trp  Tyr  Pro  Asn  Ile
                         370                     375                          380

TCC  ACT  GTC  ATG  TTC  AAG  TTC  AGA  ACA  TTT  TCT  TCG  AGT  GCT  CTT  CTG     1200
Ser  Thr  Val  Met  Phe  Lys  Phe  Arg  Thr  Phe  Ser  Ser  Ser  Ala  Leu  Leu
               385                      390                     395

ATG  TAT  CTT  GCC  ACA  CGA  GAC  CTG  AGA  GAT  TTC  ATG  AGT  GTG  GAG  CTC     1248
Met  Tyr  Leu  Ala  Thr  Arg  Asp  Leu  Arg  Asp  Phe  Met  Ser  Val  Glu  Leu
          400                      405                     410

ACT  GAT  GGG  CAC  ATA  AAA  GTC  AGT  TAC  GAT  CTG  GGC  TCA  GGA  ATG  GCT     1296
Thr  Asp  Gly  His  Ile  Lys  Val  Ser  Tyr  Asp  Leu  Gly  Ser  Gly  Met  Ala
     415                           420                     425

TCC  GTT  GTC  AGC  AAT  CAA  AAC  CAT  AAT  GAT  GGG  AAA  TGG  AAA  TCA  TTC     1344
Ser  Val  Val  Ser  Asn  Gln  Asn  His  Asn  Asp  Gly  Lys  Trp  Lys  Ser  Phe
430                      435                     440                          445

ACT  CTG  TCA  AGA  ATT  CAA  AAA  CAA  GCC  AAT  ATA  TCA  ATT  GTA  GAT  ATA     1392
Thr  Leu  Ser  Arg  Ile  Gln  Lys  Gln  Ala  Asn  Ile  Ser  Ile  Val  Asp  Ile
                         450                     455                          460

GAT  ACT  AAT  CAG  GAG  GAG  AAT  ATA  GCA  ACT  TCG  TCT  TCT  GGA  AAC  AAC     1440
Asp  Thr  Asn  Gln  Glu  Glu  Asn  Ile  Ala  Thr  Ser  Ser  Ser  Gly  Asn  Asn
               465                      470                     475

TTT  GGT  CTT  GAC  TTG  AAA  GCA  GAT  GAC  AAA  ATA  TAT  TTT  GGT  GGC  CTG     1488
Phe  Gly  Leu  Asp  Leu  Lys  Ala  Asp  Asp  Lys  Ile  Tyr  Phe  Gly  Gly  Leu
          480                      485                     490

CCA  ACG  CTG  AGA  AAC  TTG  AGT  ATG  AAA  GCA  AGG  CCA  GAA  GTA  AAT  CTG     1536
Pro  Thr  Leu  Arg  Asn  Leu  Ser  Met  Lys  Ala  Arg  Pro  Glu  Val  Asn  Leu
     495                           500                     505

AAG  AAA  TAT  TCC  GGC  TGC  CTC  AAA  GAT  ATT  GAA  ATT  TCA  AGA  ACT  CCG     1584
Lys  Lys  Tyr  Ser  Gly  Cys  Leu  Lys  Asp  Ile  Glu  Ile  Ser  Arg  Thr  Pro
510                      515                     520                          525

TAC  AAT  ATA  CTC  AGT  AGT  CCC  GAT  TAT  GTT  GGT  GTT  ACC  AAA  GGA  TGT     1632
Tyr  Asn  Ile  Leu  Ser  Ser  Pro  Asp  Tyr  Val  Gly  Val  Thr  Lys  Gly  Cys
                         530                     535                          540

TCC  CTG  GAG  AAT  GTT  TAC  ACA  GTT  AGC  TTT  CCT  AAG  CCT  GGT  TTT  GTG     1680
Ser  Leu  Glu  Asn  Val  Tyr  Thr  Val  Ser  Phe  Pro  Lys  Pro  Gly  Phe  Val
```

|     |     |     |     |     | 545 |     |     |     |     | 550 |     |     |     |     | 555 |     |     |      |
|-----|-----|-----|-----|-----|-----|-----|-----|-----|-----|-----|-----|-----|-----|-----|-----|-----|-----|------|
| GAG | CTC | TCC | CCT | GTG | CCA | ATT | GAT | GTA | GGA | ACA | GAA | ATC | AAC | CTG | TCA |     |     | 1728 |
| Glu | Leu | Ser | Pro | Val | Pro | Ile | Asp | Val | Gly | Thr | Glu | Ile | Asn | Leu | Ser |     |     |      |
|     |     | 560 |     |     |     | 565 |     |     |     | 570 |     |     |     |     |     |     |     |      |

| TTC | AGC | ACC | AAG | AAT | GAG | TCC | GGC | ATC | ATT | CTT | TTG | GGA | AGT | GGA | GGG | 1776 |
|-----|-----|-----|-----|-----|-----|-----|-----|-----|-----|-----|-----|-----|-----|-----|-----|------|
| Phe | Ser | Thr | Lys | Asn | Glu | Ser | Gly | Ile | Ile | Leu | Leu | Gly | Ser | Gly | Gly |      |
|     | 575 |     |     |     |     | 580 |     |     |     |     | 585 |     |     |     |     |      |

| ACA | CCA | GCA | CCA | CCT | AGG | AGA | AAA | CGA | AGG | CAG | ACT | GGA | CAG | GCC | TAT | 1824 |
| Thr | Pro | Ala | Pro | Pro | Arg | Arg | Lys | Arg | Arg | Gln | Thr | Gly | Gln | Ala | Tyr |      |
| 590 |     |     |     |     | 595 |     |     |     |     | 600 |     |     |     |     | 605 |      |

| TAT | GTA | ATA | CTC | CTC | AAC | AGG | GGC | CGT | CTG | GAA | GTG | CAT | CTC | TCC | ACA | 1872 |
| Tyr | Val | Ile | Leu | Leu | Asn | Arg | Gly | Arg | Leu | Glu | Val | His | Leu | Ser | Thr |      |
|     |     |     |     | 610 |     |     |     |     | 615 |     |     |     |     |     | 620 |      |

| GGG | GCA | CGA | ACA | ATG | AGG | AAA | ATT | GTC | ATC | AGA | CCA | GAG | CCG | AAT | CTG | 1920 |
| Gly | Ala | Arg | Thr | Met | Arg | Lys | Ile | Val | Ile | Arg | Pro | Glu | Pro | Asn | Leu |      |
|     |     |     | 625 |     |     |     |     | 630 |     |     |     |     | 635 |     |     |      |

| TTT | CAT | GAT | GGA | AGA | GAA | CAT | TCC | GTT | CAT | GTA | GAG | CGA | ACT | AGA | GGC | 1968 |
| Phe | His | Asp | Gly | Arg | Glu | His | Ser | Val | His | Val | Glu | Arg | Thr | Arg | Gly |      |
|     |     | 640 |     |     |     |     | 645 |     |     |     |     | 650 |     |     |     |      |

| ATC | TTT | ACA | GTT | CAA | GTG | GAT | GAA | AAC | AGA | AGA | TAC | ATG | CAA | AAC | CTG | 2016 |
| Ile | Phe | Thr | Val | Gln | Val | Asp | Glu | Asn | Arg | Arg | Tyr | Met | Gln | Asn | Leu |      |
|     | 655 |     |     |     |     | 660 |     |     |     |     | 665 |     |     |     |     |      |

| ACA | GTT | GAA | CAG | CCT | ATC | GAA | GTT | AAA | AAG | CTT | TTC | GTT | GGG | GGT | GCT | 2064 |
| Thr | Val | Glu | Gln | Pro | Ile | Glu | Val | Lys | Lys | Leu | Phe | Val | Gly | Gly | Ala |      |
| 670 |     |     |     |     | 675 |     |     |     |     | 680 |     |     |     |     | 685 |      |

| CCA | CCT | GAA | TTT | CAA | CCT | TCC | CCA | CTC | AGA | AAT | ATT | CCT | CCT | TTT | GAA | 2112 |
| Pro | Pro | Glu | Phe | Gln | Pro | Ser | Pro | Leu | Arg | Asn | Ile | Pro | Pro | Phe | Glu |      |
|     |     |     |     | 690 |     |     |     |     | 695 |     |     |     |     | 700 |     |      |

| GGC | TGC | ATA | TGG | AAT | CTT | GTT | ATT | AAC | TCT | GTC | CCC | ATG | GAC | TTT | GCA | 2160 |
| Gly | Cys | Ile | Trp | Asn | Leu | Val | Ile | Asn | Ser | Val | Pro | Met | Asp | Phe | Ala |      |
|     |     |     | 705 |     |     |     |     | 710 |     |     |     |     | 715 |     |     |      |

| AGG | CCT | GTG | TCC | TTC | AAA | AAT | GCT | GAC | ATT | GGT | CGC | TGT | GCC | CAT | CAG | 2208 |
| Arg | Pro | Val | Ser | Phe | Lys | Asn | Ala | Asp | Ile | Gly | Arg | Cys | Ala | His | Gln |      |
|     |     |     | 720 |     |     |     |     | 725 |     |     |     |     | 730 |     |     |      |

| AAA | CTC | CGT | GAA | GAT | GAA | GAT | GGA | GCA | GCT | CCA | GCT | GAA | ATA | GTT | ATC | 2256 |
| Lys | Leu | Arg | Glu | Asp | Glu | Asp | Gly | Ala | Ala | Pro | Ala | Glu | Ile | Val | Ile |      |
|     | 735 |     |     |     |     | 740 |     |     |     |     | 745 |     |     |     |     |      |

| CAG | CCT | GAG | CCA | GTT | CCC | ACC | CCA | GCC | TTT | CCT | ACG | CCC | ACC | CCA | GTT | 2304 |
| Gln | Pro | Glu | Pro | Val | Pro | Thr | Pro | Ala | Phe | Pro | Thr | Pro | Thr | Pro | Val |      |
| 750 |     |     |     |     | 755 |     |     |     |     | 760 |     |     |     |     | 765 |      |

| CTG | ACA | CAT | GGT | CCT | TGT | GCT | GCA | GAA | TCA | GAA | CCA | GCT | CTT | TTG | ATA | 2352 |
| Leu | Thr | His | Gly | Pro | Cys | Ala | Ala | Glu | Ser | Glu | Pro | Ala | Leu | Leu | Ile |      |
|     |     |     |     | 770 |     |     |     |     | 775 |     |     |     |     |     | 780 |      |

| GGG | AGC | AAG | CAG | TTC | GGG | CTT | TCA | AGA | AAC | AGT | CAC | ATT | GCA | ATT | GCA | 2400 |
| Gly | Ser | Lys | Gln | Phe | Gly | Leu | Ser | Arg | Asn | Ser | His | Ile | Ala | Ile | Ala |      |
|     |     |     | 785 |     |     |     |     | 790 |     |     |     |     | 795 |     |     |      |

| TTT | GAT | GAC | ACC | AAA | GTT | AAA | AAC | CGT | CTC | ACA | ATT | GAG | TTG | GAA | GTA | 2448 |
| Phe | Asp | Asp | Thr | Lys | Val | Lys | Asn | Arg | Leu | Thr | Ile | Glu | Leu | Glu | Val |      |
|     |     | 800 |     |     |     | 805 |     |     |     |     | 810 |     |     |     |     |      |

| AGA | ACC | GAA | GCT | GAA | TCC | GGC | TTG | CTT | TTT | TAC | ATG | GCT | GCG | ATC | AAT | 2496 |
| Arg | Thr | Glu | Ala | Glu | Ser | Gly | Leu | Leu | Phe | Tyr | Met | Ala | Ala | Ile | Asn |      |
|     |     | 815 |     |     |     |     | 820 |     |     |     |     | 825 |     |     |     |      |

| CAT | GCT | GAT | TTT | GCA | ACA | GTT | CAG | CTG | AGA | AAT | GGA | TTG | CCC | TAC | TTC | 2544 |
| His | Ala | Asp | Phe | Ala | Thr | Val | Gln | Leu | Arg | Asn | Gly | Leu | Pro | Tyr | Phe |      |
| 830 |     |     |     |     | 835 |     |     |     |     | 840 |     |     |     |     | 845 |      |

| AGC | TAT | GAC | TTG | GGG | AGT | GGG | GAC | ACC | CAC | ACC | ATG | ATC | CCC | ACC | AAA | 2592 |
| Ser | Tyr | Asp | Leu | Gly | Ser | Gly | Asp | Thr | His | Thr | Met | Ile | Pro | Thr | Lys |      |
|     |     |     |     | 850 |     |     |     |     | 855 |     |     |     |     | 860 |     |      |

| ATC | AAT | GAT | GGC | CAG | TGG | CAC | AAG | ATT | AAG | ATA | ATG | AGA | AGT | AAG | CAA | 2640 |
| Ile | Asn | Asp | Gly | Gln | Trp | His | Lys | Ile | Lys | Ile | Met | Arg | Ser | Lys | Gln |      |

```
                       865                          870                           875
GAA  GGA  ATT  CTT  TAT  GTA  GAT  GGG  GCT  TCC  AAC  AGA  ACC  ATC  AGT  CCC         2688
Glu  Gly  Ile  Leu  Tyr  Val  Asp  Gly  Ala  Ser  Asn  Arg  Thr  Ile  Ser  Pro
          880                    885                    890

AAA  AAA  GCC  GAC  ATC  CTG  GAT  GTC  GTG  GGA  ATG  CTG  TAT  GTT  GGT  GGG         2736
Lys  Lys  Ala  Asp  Ile  Leu  Asp  Val  Val  Gly  Met  Leu  Tyr  Val  Gly  Gly
     895                           900                    905

TTA  CCC  ATC  AAC  TAC  ACT  ACC  CGA  AGA  ATT  GGT  CCA  GTG  ACC  TAT  AGC         2784
Leu  Pro  Ile  Asn  Tyr  Thr  Thr  Arg  Arg  Ile  Gly  Pro  Val  Thr  Tyr  Ser
910                      915                    920                           925

ATT  GAT  GGC  TGC  GTC  AGG  AAT  CTC  CAC  ATG  GCA  GAG  GCC  CCT  GCC  GAT         2832
Ile  Asp  Gly  Cys  Val  Arg  Asn  Leu  His  Met  Ala  Glu  Ala  Pro  Ala  Asp
                    930                    935                           940

CTG  GAA  CAA  CCC  ACC  TCC  AGC  TTC  CAT  GTT  GGG  ACA  TGT  TTT  GCA  AAT         2880
Leu  Glu  Gln  Pro  Thr  Ser  Ser  Phe  His  Val  Gly  Thr  Cys  Phe  Ala  Asn
               945                    950                           955

GCT  CAG  AGG  GGA  ACA  TAT  TTT  GAC  GGA  ACC  GGT  TTT  GCC  AAA  GCA  GTT         2928
Ala  Gln  Arg  Gly  Thr  Tyr  Phe  Asp  Gly  Thr  Gly  Phe  Ala  Lys  Ala  Val
          960                    965                           970

GGT  GGA  TTC  AAA  GTG  GGA  TTG  GAC  CTT  CTT  GTA  GAA  TTT  GAA  TTC  GCG         2976
Gly  Gly  Phe  Lys  Val  Gly  Leu  Asp  Leu  Leu  Val  Glu  Phe  Glu  Phe  Ala
975                           980                    985

ACA  ACT  ACA  ACG  ACT  GGA  GTT  CTT  CTG  GGG  ATC  AGT  AGT  CAA  AAA  ATG         3024
Thr  Thr  Thr  Thr  Thr  Gly  Val  Leu  Leu  Gly  Ile  Ser  Ser  Gln  Lys  Met
990                      995                    1000                          1005

GAT  GGA  ATG  GGT  ATT  GAA  ATG  ATT  GAT  GAA  AAG  TTG  ATG  TTT  CAT  GTG         3072
Asp  Gly  Met  Gly  Ile  Glu  Met  Ile  Asp  Glu  Lys  Leu  Met  Phe  His  Val
                         1010                    1015                         1020

GAC  AAT  GGT  GCG  GGC  AGA  TTC  ACT  GCT  GTC  TAT  GAT  GCT  GGG  GTT  CCA         3120
Asp  Asn  Gly  Ala  Gly  Arg  Phe  Thr  Ala  Val  Tyr  Asp  Ala  Gly  Val  Pro
                    1025                    1030                         1035

GGG  CAT  TTG  TGT  GAT  GGA  CAA  TGG  CAT  AAA  GTC  ACT  GCC  AAC  AAG  ATC         3168
Gly  His  Leu  Cys  Asp  Gly  Gln  Trp  His  Lys  Val  Thr  Ala  Asn  Lys  Ile
               1040                    1045                         1050

AAA  CAC  CGC  ATT  GAG  CTC  ACA  GTC  GAT  GGG  AAC  CAG  GTG  GAA  GCC  CAA         3216
Lys  His  Arg  Ile  Glu  Leu  Thr  Val  Asp  Gly  Asn  Gln  Val  Glu  Ala  Gln
          1055                    1060                         1065

AGC  CCA  AAC  CCA  GCA  TCT  ACA  TCA  GCT  GAC  ACA  AAT  GAC  CCT  GTG  TTT         3264
Ser  Pro  Asn  Pro  Ala  Ser  Thr  Ser  Ala  Asp  Thr  Asn  Asp  Pro  Val  Phe
1070                     1075                    1080                         1085

GTT  GGA  GGC  TTC  CCA  GAT  GAC  CTC  AAG  CAG  TTT  GGC  CTA  ACA  ACC  AGT         3312
Val  Gly  Gly  Phe  Pro  Asp  Asp  Leu  Lys  Gln  Phe  Gly  Leu  Thr  Thr  Ser
                    1090                    1095                         1100

ATT  CCG  TTC  CGA  GGT  TGC  ATC  AGA  TCC  CTG  AAG  CTC  ACC  AAA  GGC  ACA         3360
Ile  Pro  Phe  Arg  Gly  Cys  Ile  Arg  Ser  Leu  Lys  Leu  Thr  Lys  Gly  Thr
               1105                    1110                         1115

GCA  AGC  CAC  TGG  AGG  TTA  ATT  TTG  CCA  AGG  CCC  TGG  AAC  T  GAGGGCGTT          3410
Ala  Ser  His  Trp  Arg  Leu  Ile  Leu  Pro  Arg  Pro  Trp  Asn
          1120                    1125                    113

CAACCTGTAT CATGCCCAGC CAACTAATAA AAATAAGTGT AACCCCAGGA AGAGTCTGTC                      3470

AAAACAAGTA TATCAAGTAA AACAAACAAA TATATTTTAC CTATATATGT TAATTAAACT                      3530

AATTTGTGCA TGTACATAGA ATTC                                                             3554
```

( 2 ) INFORMATION FOR SEQ ID NO:2:

( i ) SEQUENCE CHARACTERISTICS:
        ( A ) LENGTH: 1130 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val Lys Lys Leu Ala Asn Asp Val Lys Glu Asn Glu Asp His Leu Asn
  1               5                  10                  15

Gly Leu Lys Thr Arg Ile Glu Asn Ala Asp Ala Arg Asn Gly Asp Leu
              20                  25                  30

Leu Arg Thr Leu Asn Asp Thr Leu Gly Lys Leu Ser Ala Ile Pro Asn
          35                  40                  45

Asp Thr Ala Ala Lys Leu Gln Ala Val Lys Asp Lys Ala Arg Gln Ala
      50                  55                  60

Asn Asp Thr Ala Lys Asp Val Leu Ala Gln Ile Thr Glu Leu His Gln
 65                  70                  75                  80

Asn Leu Asp Gly Leu Lys Lys Asn Tyr Asn Lys Leu Ala Asp Ser Val
                  85                  90                  95

Ala Lys Thr Asn Ala Val Val Lys Asp Pro Ser Lys Asn Lys Ile Ile
              100                 105                 110

Ala Asp Ala Asp Ala Thr Val Lys Asn Leu Glu Gln Glu Ala Asp Arg
          115                 120                 125

Leu Ile Asp Lys Leu Lys Pro Ile Lys Glu Leu Glu Asp Asn Leu Lys
      130                 135                 140

Lys Asn Ile Ser Glu Ile Lys Glu Leu Ile Asn Gln Ala Arg Lys Gln
145                 150                 155                 160

Ala Asn Ser Ile Lys Val Ser Val Ser Ser Gly Gly Asp Cys Ile Arg
              165                 170                 175

Thr Tyr Lys Pro Glu Ile Lys Lys Gly Ser Tyr Asn Asn Ile Val Val
              180                 185                 190

Asn Val Lys Thr Ala Val Ala Asp Asn Leu Leu Phe Tyr Leu Gly Ser
          195                 200                 205

Ala Lys Phe Ile Asp Phe Leu Ala Ile Glu Met Arg Lys Gly Lys Val
      210                 215                 220

Ser Phe Leu Trp Asp Val Gly Ser Gly Val Gly Arg Val Glu Tyr Pro
225                 230                 235                 240

Asp Leu Thr Ile Asp Asp Ser Tyr Trp Tyr Arg Ile Val Ala Ser Arg
              245                 250                 255

Thr Gly Arg Asn Gly Thr Ile Ser Val Arg Ala Leu Asp Gly Pro Lys
              260                 265                 270

Ala Ser Ile Val Pro Ser Thr His His Ser Thr Ser Pro Pro Gly Tyr
          275                 280                 285

Thr Ile Leu Asp Val Asp Ala Asn Ala Met Leu Phe Val Gly Gly Leu
      290                 295                 300

Thr Gly Lys Leu Lys Lys Ala Asp Ala Val Arg Val Ile Thr Phe Thr
305                 310                 315                 320

Gly Cys Met Gly Glu Thr Tyr Phe Asp Asn Lys Pro Ile Gly Leu Trp
              325                 330                 335

Asn Phe Arg Glu Lys Glu Gly Asp Cys Lys Gly Cys Thr Val Ser Pro
              340                 345                 350

Gln Val Glu Asp Ser Glu Gly Thr Ile Gln Phe Asp Gly Glu Gly Tyr
          355                 360                 365

Ala Leu Val Ser Arg Pro Ile Arg Trp Tyr Pro Asn Ile Ser Thr Val
      370                 375                 380

Met Phe Lys Phe Arg Thr Phe Ser Ser Ser Ala Leu Leu Met Tyr Leu
385                 390                 395                 400

Ala Thr Arg Asp Leu Arg Asp Phe Met Ser Val Glu Leu Thr Asp Gly
```

-continued

```
                       405                         410                         415
    His  Ile  Lys  Val  Ser  Tyr  Asp  Leu  Ser  Gly  Met  Ala  Ser  Val  Val
                   420                      425                      430

Ser  Asn  Gln  Asn  His  Asn  Asp  Gly  Lys  Trp  Lys  Ser  Phe  Thr  Leu  Ser
              435                      440                      445

Arg  Ile  Gln  Lys  Gln  Ala  Asn  Ile  Ser  Ile  Val  Asp  Ile  Asp  Thr  Asn
         450                      455                      460

Gln  Glu  Glu  Asn  Ile  Ala  Thr  Ser  Ser  Ser  Gly  Asn  Asn  Phe  Gly  Leu
    465                      470                      475                      480

Asp  Leu  Lys  Ala  Asp  Asp  Lys  Ile  Tyr  Phe  Gly  Gly  Leu  Pro  Thr  Leu
                        485                      490                      495

Arg  Asn  Leu  Ser  Met  Lys  Ala  Arg  Pro  Glu  Val  Asn  Leu  Lys  Lys  Tyr
                   500                      505                      510

Ser  Gly  Cys  Leu  Lys  Asp  Ile  Glu  Ile  Ser  Arg  Thr  Pro  Tyr  Asn  Ile
              515                      520                      525

Leu  Ser  Ser  Pro  Asp  Tyr  Val  Gly  Val  Thr  Lys  Gly  Cys  Ser  Leu  Glu
         530                      535                      540

Asn  Val  Tyr  Thr  Val  Ser  Phe  Pro  Lys  Pro  Gly  Phe  Val  Glu  Leu  Ser
    545                      550                      555                      560

Pro  Val  Pro  Ile  Asp  Val  Gly  Thr  Glu  Ile  Asn  Leu  Ser  Phe  Ser  Thr
                        565                      570                      575

Lys  Asn  Glu  Ser  Gly  Ile  Ile  Leu  Leu  Gly  Ser  Gly  Gly  Thr  Pro  Ala
                   580                      585                      590

Pro  Pro  Arg  Arg  Lys  Arg  Arg  Gln  Thr  Gly  Gln  Ala  Tyr  Tyr  Val  Ile
              595                      600                      605

Leu  Leu  Asn  Arg  Gly  Arg  Leu  Glu  Val  His  Leu  Ser  Thr  Gly  Ala  Arg
         610                      615                      620

Thr  Met  Arg  Lys  Ile  Val  Ile  Arg  Pro  Glu  Pro  Asn  Leu  Phe  His  Asp
    625                      630                      635                      640

Gly  Arg  Glu  His  Ser  Val  His  Val  Glu  Arg  Thr  Arg  Gly  Ile  Phe  Thr
                        645                      650                      655

Val  Gln  Val  Asp  Glu  Asn  Arg  Arg  Tyr  Met  Gln  Asn  Leu  Thr  Val  Glu
                   660                      665                      670

Gln  Pro  Ile  Glu  Val  Lys  Lys  Leu  Phe  Val  Gly  Gly  Ala  Pro  Pro  Glu
              675                      680                      685

Phe  Gln  Pro  Ser  Pro  Leu  Arg  Asn  Ile  Pro  Pro  Phe  Glu  Gly  Cys  Ile
         690                      695                      700

Trp  Asn  Leu  Val  Ile  Asn  Ser  Val  Pro  Met  Asp  Phe  Ala  Arg  Pro  Val
    705                      710                      715                      720

Ser  Phe  Lys  Asn  Ala  Asp  Ile  Gly  Arg  Cys  Ala  His  Gln  Lys  Leu  Arg
                        725                      730                      735

Glu  Asp  Glu  Asp  Gly  Ala  Ala  Pro  Ala  Glu  Ile  Val  Ile  Gln  Pro  Glu
                   740                      745                      750

Pro  Val  Pro  Thr  Pro  Ala  Phe  Pro  Thr  Pro  Thr  Pro  Val  Leu  Thr  His
              755                      760                      765

Gly  Pro  Cys  Ala  Ala  Glu  Ser  Glu  Pro  Ala  Leu  Leu  Ile  Gly  Ser  Lys
         770                      775                      780

Gln  Phe  Gly  Leu  Ser  Arg  Asn  Ser  His  Ile  Ala  Ile  Ala  Phe  Asp  Asp
    785                      790                      795                      800

Thr  Lys  Val  Lys  Asn  Arg  Leu  Thr  Ile  Glu  Leu  Glu  Val  Arg  Thr  Glu
                        805                      810                      815

Ala  Glu  Ser  Gly  Leu  Leu  Phe  Tyr  Met  Ala  Ala  Ile  Asn  His  Ala  Asp
                   820                      825                      830
```

```
            Phe  Ala  Thr  Val  Gln  Leu  Arg  Asn  Gly  Leu  Pro  Tyr  Phe  Ser  Tyr  Asp
                      835                     840                     845

Leu  Gly  Ser  Gly  Asp  Thr  His  Thr  Met  Ile  Pro  Thr  Lys  Ile  Asn  Asp
                      850                     855                     860

Gly  Gln  Trp  His  Lys  Lys  Ile  Met  Arg  Ser  Lys  Gln  Glu  Gly  Ile
            865                 870                     875                          880

Leu  Tyr  Val  Asp  Gly  Ala  Ser  Asn  Arg  Thr  Ile  Ser  Pro  Lys  Lys  Ala
                           885                          890                     895

Asp  Ile  Leu  Asp  Val  Val  Gly  Met  Leu  Tyr  Val  Gly  Gly  Leu  Pro  Ile
                           900                     905                     910

Asn  Tyr  Thr  Thr  Arg  Arg  Ile  Gly  Pro  Val  Thr  Tyr  Ser  Ile  Asp  Gly
                      915                     920                     925

Cys  Val  Arg  Asn  Leu  His  Met  Ala  Glu  Ala  Pro  Ala  Asp  Leu  Glu  Gln
                      930                     935                     940

Pro  Thr  Ser  Ser  Phe  His  Val  Gly  Thr  Cys  Phe  Ala  Asn  Ala  Gln  Arg
            945                      950                     955                          960

Gly  Thr  Tyr  Phe  Asp  Gly  Thr  Gly  Phe  Ala  Lys  Ala  Val  Gly  Gly  Phe
                           965                     970                          975

Lys  Val  Gly  Leu  Asp  Leu  Leu  Val  Glu  Phe  Glu  Phe  Ala  Thr  Thr  Thr
                           980                     985                     990

Thr  Thr  Gly  Val  Leu  Leu  Gly  Ile  Ser  Ser  Gln  Lys  Met  Asp  Gly  Met
                      995                     1000                    1005

Gly  Ile  Glu  Met  Ile  Asp  Glu  Lys  Leu  Met  Phe  His  Val  Asp  Asn  Gly
                      1010                    1015                    1020

Ala  Gly  Arg  Phe  Thr  Ala  Val  Tyr  Asp  Ala  Gly  Val  Pro  Gly  His  Leu
            1025                     1030                    1035                         1040

Cys  Asp  Gly  Gln  Trp  His  Lys  Val  Thr  Ala  Asn  Lys  Ile  Lys  His  Arg
                                1045                    1050                    1055

Ile  Glu  Leu  Thr  Val  Asp  Gly  Asn  Gln  Val  Glu  Ala  Gln  Ser  Pro  Asn
                           1060                    1065                    1070

Pro  Ala  Ser  Thr  Ser  Ala  Asp  Thr  Asn  Asp  Pro  Val  Phe  Val  Gly  Gly
                      1075                    1080                    1085

Phe  Pro  Asp  Asp  Leu  Lys  Gln  Phe  Gly  Leu  Thr  Thr  Ser  Ile  Pro  Phe
                      1090                    1095                    1100

Arg  Gly  Cys  Ile  Arg  Ser  Leu  Lys  Leu  Thr  Lys  Gly  Thr  Ala  Ser  His
            1105                     1110                    1115                         1120

Trp  Arg  Leu  Ile  Leu  Pro  Arg  Pro  Trp  Asn
                           1125                    1130

( 2 ) INFORMATION FOR SEQ ID NO:3:

( i ) SEQUENCE CHARACTERISTICS:
              ( A ) LENGTH: 6942 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:3:

CAGCGACTCC  TCTGGCTCCC  GAGAAGTGGA  TCCGGTCGCG  GCCACTACGA  TGCCGGGAGC        60

CGCCGGGGTC  CTCCTCCTTC  TGCTGCTCTC  CGGAGGCCTC  GGGGGCGTAC  AGGCGCAGCG       120

GCCGCAGCAG  CAGCGGCAGT  CACAGGCACA  TCAGCAAAGA  GGTTTATTCC  CTGCTGTCCT       180

GAATCTTGCT  TCTAATGCTC  TTATCACGAC  CAATGCAACA  TGTGGAGAAA  AAGGACCTGA       240

AATGTACTGC  AAATTGGTAG  AACATGTCCC  TGGGCAGCCT  GTGAGGAACC  CGCAGTGTCG       300

AATCTGCAAT  CAAAACAGCA  GCAATCCAAA  CCAGAGACAC  CCGATTACAA  ATGCTATTGA       360
```

| | | | | | | |
|---|---|---|---|---|---|---|
| TGGAAAGAAC | ACTTGGTGGC | AGAGTCCCAG | TATTAAGAAT | GGAATCGAAT | ACCATTATGT | 420 |
| GACAATTACA | CTGGATTTAC | AGCAGGTGTT | CCAGATCGCG | TATGTGATTG | TGAAGGCAGC | 480 |
| TAACTCCCCC | CGGCCTGGAA | ACTGGATTTT | GGAACGCTCT | CTTGATGATG | TTGAATACAA | 540 |
| GCCCTGGCAG | TATCATGCTG | TGACAGACAC | GGAGTGCCTA | ACGCTTTACA | ATATTTATCC | 600 |
| CCGCACTGGG | CCACCGTCAT | ATGCCAAAGA | TGATGAGGTC | ATCTGCACTT | CATTTACTC | 660 |
| CAAGATACAC | CCCTTAGAAA | ATGGAGAGAT | TCACATCTCT | TTAATCAATG | GGAGACCAAG | 720 |
| TGCCGATGAT | CCTTCTCCAG | AACTGCTAGA | ATTTACCTCC | GCTCGCTATA | TTCGCCTGAG | 780 |
| ATTTCAGAGG | ATCCGCACAC | TGAATGCTGA | CTTGATGATG | TTTGCTCACA | AAGACCCAAG | 840 |
| AGAAATTGAC | CCCATTGTCA | CCAGAAGATA | TTACTACTCG | GTCAAGGATA | TTTCAGTTGG | 900 |
| AGGGATGTGC | ATCTGCTATG | GTCATGCCAG | GGCTTGTCCA | CTTGATCCAG | CGACAAATAA | 960 |
| ATCTCGCTGT | GAGTGTGAGC | ATAACACATG | TGGCGATAGC | TGTGATCAGT | GCTGTCCAGG | 1020 |
| ATTCCATCAG | AAACCCTGGA | GAGCTGGAAC | TTTTCTAACT | AAAACTGAAT | GTGAAGCATG | 1080 |
| CAATTGTCAT | GGAAAAGCTG | AAGAATGCTA | TTATGATGAA | AATGTTGCCA | GAAGAAATCT | 1140 |
| GAGTTTGAAT | ATACGTGGAA | AGTACATTGG | AGGGGGTGTC | TGCATTAATT | GTACCCAAAA | 1200 |
| CACTGCTGGT | ATAAACTGCG | AGACATGTAC | AGATGGCTTC | TTCAGACCCA | AGGGGTATC | 1260 |
| TCCAAATTAT | CCAAGGCCAT | GCCAGCCATG | TCATTGCGAT | CCAATTGGTT | CCTTAAATGA | 1320 |
| AGTCTGTGTC | AAGGATGAGA | AACATGCTCG | ACGAGGTTTG | GCACCTGGAT | CCTGTCATTG | 1380 |
| CAAAACTGGT | TTTGGAGGTG | TGAGCTGTGA | TCGGTGTGCC | AGGGGCTACA | CTGGCTACCC | 1440 |
| GGACTGCAAA | GCCTGTAACT | GCAGTGGGTT | AGGGAGCAAA | AATGAGGATC | CTTGTTTTGG | 1500 |
| CCCCTGTATC | TGCAAGGAAA | ATGTTGAAGG | AGGAGACTGT | AGTCGTTGCA | AATCCGGCTT | 1560 |
| CTTCAATTTG | CAAGAGGATA | ATTGGAAAGG | CTGCGATGAG | TGTTTCTGTT | CAGGGGTTTC | 1620 |
| AAACAGATGT | CAGAGTTCCT | ACTGGACCTA | TGGCAAAATA | CAAGATATGA | GTGGCTGGTA | 1680 |
| TCTGACTGAC | CTTCCTGGCC | GCATTCGAGT | GGCTCCCCAG | CAGGACGACT | TGGACTCACC | 1740 |
| TCAGCAGATC | AGCATCAGTA | ACGCGGAGGC | CCGGCAAGCC | CTGCCGCACA | GCTACTACTG | 1800 |
| GAGCGCGCCG | GCTCCCTATC | TGGGAAACAA | ACTCCCAGCA | GTAGGAGGAC | AGTTGACATT | 1860 |
| TACCATATCA | TATGACCTTG | AAGAAGAGGA | AGAAGATACA | GAACGTGTTC | TCCAGCTTAT | 1920 |
| GATTATCTTA | GAGGGTAATG | ACTTGAGCAT | CAGCACAGCC | CAAGATGAGG | TGTACCTGCA | 1980 |
| CCCATCTGAA | GAACATACTA | ATGTATTGTT | ACTTAAAGAA | GAATCATTTA | CCATACATGG | 2040 |
| CACACATTTT | CCAGTCCGTA | GAAAGGAATT | TATGACAGTG | CTTGCGAATT | TGAAGAGAGT | 2100 |
| CCTCCTACAA | ATCACATACA | GCTTTGGGAT | GGATGCCATC | TTCAGGTTGA | GCTCTGTTAA | 2160 |
| CCTTGAATCC | GCTGTCTCCT | ATCCTACTGA | TGGAAGCATT | GCAGCAGCTG | TAGAAGTGTG | 2220 |
| TCAGTGCCCA | CCAGGGTATA | CTGGCTCCTC | TTGTGAATCT | TGTTGGCCTA | GGCACAGGCG | 2280 |
| AGTTAACGGC | ACTATTTTTG | GTGGCATCTG | TGAGCCATGT | CAGTGCTTTG | GTCATGCGGA | 2340 |
| GTCCTGTGAT | GACGTCACTG | GAGAATGCCT | GAACTGTAAG | GATCACACAG | GTGGCCCATA | 2400 |
| TTGTGATAAA | TGTCTTCCTG | GTTTCTATGG | CGAGCCTACT | AAAGGAACCT | CTGAAGACTG | 2460 |
| TCAACCCTGT | GCCTGTCCAC | TCAATATCCC | ATCCAATAAC | TTTAGCCCAA | CGTGCCATTT | 2520 |
| AGACCGGAGT | CTTGGATTGA | TCTGTGATGG | ATGCCCTGTC | GGGTACACAG | GACCACGCTG | 2580 |
| TGAGAGGTGT | GCAGAAGGCT | ATTTTGGACA | ACCCTCTGTA | CCTGGAGGAT | CATGTCAGCC | 2640 |
| ATGCCAATGC | AATGACAACC | TTGACTTCTC | CATCCCTGGC | AGCTGTGACA | GCTTGTCTGG | 2700 |
| CTCCTGTCTG | ATATGTAAAC | CAGGTACAAC | AGGCCGGTAC | TGTGAGCTCT | GTGCTGATGG | 2760 |

-continued

| | | | | | |
|---|---|---|---|---|---|
| ATATTTTGGA | GATGCAGTTG | ATGCGAAGAA | CTGTCAGCCC | TGTCGCTGTA | ATGCCGGTGG | 2820
| CTCTTTCTCT | GAGGTTTGCC | ACAGTCAAAC | TGGACAGTGT | GAGTGCAGAG | CCAACGTTCA | 2880
| GGGTCAGAGA | TGTGACAAAT | GCAAGGCTGG | GACCTTTGGC | CTACAATCAG | CAAGGGGCTG | 2940
| TGTTCCCTGC | AACTGCAATT | CTTTTGGGTC | TAAGTCATTC | GACTGTGAAG | AGAGTGGACA | 3000
| ATGTTGGTGC | CAACCTGGAG | TCACAGGGAA | GAAATGTGAC | CGCTGTGCCC | ACGGCTATTT | 3060
| CAACTTCCAA | GAAGGAGGCT | GCACAGCTTG | TGAATGTTCT | CATCTGGGTA | ATAATTGTGA | 3120
| CCCAAAGACT | GGGCGATGCA | TTTGCCCACC | CAATACCATT | GGAGAGAAAT | GTTCTAAATG | 3180
| TGCACCCAAT | ACCTGGGGCC | ACAGCATTAC | CACTGGTTGT | AAGGCTTGTA | ACTGCAGCAC | 3240
| AGTGGGATCC | TTGGATTTCC | AATGCAATGT | AAATACAGGC | CAATGCAACT | GTCATCCAAA | 3300
| ATTCTCTGGT | GCAAAATGTA | CAGAGTGCAG | TCGAGGTCAC | TGGAACTACC | CTCGCTGCAA | 3360
| TCTCTGTGAC | TGCTTCCTCC | CTGGGACAGA | TGCCACAACC | TGTGATTCAG | AGACTAAAAA | 3420
| ATGCTCCTGT | AGTGATCAAA | CTGGGCAGTG | CACTTGTAAG | GTGAATGTGG | AAGGCATCCA | 3480
| CTGTGACAGA | TGCCGGCCTG | GCAAATTCGG | ACTCGATGCC | AAGAATCCAC | TTGGCTGCAG | 3540
| CAGCTGCTAT | TGCTTCGGCA | CTACTACCCA | GTGCTCTGAA | GCAAAAGGAC | TGATCCGGAC | 3600
| GTGGGTGACT | CTGAAGGCTG | AGCAGACCAT | TCTACCCCTG | GTAGATGAGG | CTCTGCAGCA | 3660
| CACGACCACC | AAGGGCATTG | TTTTTCAACA | TCCAGAGATT | GTTGCCCACA | TGGACCTGAT | 3720
| GAGAGAAGAT | CTCCATTTGG | AACCTTTTTA | TTGGAAACTT | CCAGAACAAT | TTGAAGGAAA | 3780
| GAAGTTGATG | GCCTATGGGG | GCAAACTCAA | GTATGCAATC | TATTTCGAGG | CTCGGGAAGA | 3840
| AACAGGTTTC | TCTACATATA | ATCCTCAAGT | GATCATTCGA | GGTGGGACAC | CTACTCATGC | 3900
| TAGAATTATC | GTCAGGCATA | TGGCTGCTCC | TCTGATTGGC | CAATTGACAA | GGCATGAAAT | 3960
| TGAAATGACA | GAGAAAGAAT | GGAAATATTA | TGGGGATGAT | CCTCGAGTCC | ATAGAACTGT | 4020
| GACCCGAGAA | GACTTCTTGG | ATATACTATA | TGATATTCAT | TACATTCTTA | TCAAAGCTAC | 4080
| TTATGGAAAT | TTCATGCGAC | AAAGCAGGAT | TTCTGAAATC | TCAATGGAGG | TAGCTGAACA | 4140
| AGGACGTGGA | ACAACAATGA | CTCCTCCAGC | TGACTTGATT | GAAAATGTG | ATTGTCCCCT | 4200
| GGGCTATTCT | GGCCTGTCCT | GTGAGGCATG | CTTGCCGGGA | TTTTATCGAC | TGCGTTCTCA | 4260
| ACCAGGTGGC | CGCACCCCTG | GACCAACCCT | GGGCACCTGT | GTTCCATGTC | AATGTAATGG | 4320
| ACACAGCAGC | CTGTGTGACC | CTGAAACATC | GATATGCCAG | AATTGTCAAC | ATCACACTGC | 4380
| TGGTGACTTC | TGTGAACGAT | GTGCTCTTGG | ATACTATGGA | ATTGTCAAGG | GATTGCCAAA | 4440
| TGACTGTCAG | CAATGTGCCT | GCCCTCTGAT | TTCTTCCAGT | AACAATTTCA | GCCCCTCTTG | 4500
| TGTCGCAGAA | GGACTTGACG | ACTACCGCTG | CACGGCTTGT | CCACGGGGAT | ATGAAGGCCA | 4560
| GTACTGTGAA | AGGTGTGCCC | CTGGCTATAC | TGGCAGTCCA | GGCAACCCTG | GAGGCTCCTG | 4620
| CCAAGAATGT | GAGTGTGATC | CCTATGGCTC | ACTGCCTGTG | CCCTGTGACC | CTGTCACAGG | 4680
| ATTCTGCACG | TGCCGACCTG | GAGCCACGGG | AAGGAAGTGT | GACGGCTGCA | AGCACTGGCA | 4740
| TGCACGCGAG | GGCTGGGAGT | GTGTTTTTTG | TGGAGATGAG | TGCACTGGCC | TTCTTCTCGG | 4800
| TGACTTGGCT | CGCCTGGAGC | AGATGGTCAT | GAGCATCAAC | CTCACTGGTC | CGCTGCCTGC | 4860
| GCCATATAAA | ATGCTGTATG | GTCTTGAAAA | TATGACTCAG | GAGCTAAAGC | ACTTGCTGTC | 4920
| ACCTCAGCGG | GCCCCAGAGA | GGCTTATTCA | GCTGGCAGAG | GGCAATCTGA | ATACACTCGT | 4980
| GACCGAAATG | AACGAGCTGC | TGACCAGGGC | TACCAAAGTG | ACAGCAGATG | GCGAGCAGAC | 5040
| CGGACAGGAT | GCTGAGAGGA | CCAACACAAG | AGCAAAGTCC | CTGGGAGAAT | TCATTAAGGA | 5100
| GCTTGCCCGG | GATGCAGAAG | CTGTAAATGA | AAAAGCTATA | AAACTAAATG | AAACTCTAGG | 5160

| | | | | | |
|---|---|---|---|---|---|
| AACTCGAGAC | GAGGCCTTTG | AGAGAAATTT | GGAAGGGCTT | CAGAAAGAGA | TTGACCAGAT | 5220 |
| GATTAAAGAA | CTGAGGAGGA | AAAATCTAGA | GACACAAAAG | GAAATTGCTG | AAGATGAGTT | 5280 |
| GGTAGCTGCA | GAAGCCCTTC | TGAAAAAGT | GAAGAAGCTG | TTTGGAGAGT | CCCGGGGGGA | 5340 |
| AAATGAAGAA | ATGGAGAAGG | ATCTCCGGGA | AAAACTGGCT | GACTACAAAA | ACAAAGTTGA | 5400 |
| TGATGCTTGG | GACCTTTTGA | GAGAAGCCAC | AGATAAAATC | AGAGAAGCTA | ATCGCCTATT | 5460 |
| TGCAGTAAAT | CAGAAAAACA | TGACTGCATT | GGAGAAAAAG | AAGGAGGCTG | TTGAGAGCGG | 5520 |
| CAAACGACAA | ATTGAGAACA | CTTTAAAAGA | AGGCAATGAC | ATACTCGATG | AAGCCAACCG | 5580 |
| TCTTGCAGAT | GAAATCAACT | CCATCATAGA | CTATGTTGAA | GACATCCAAA | CTAAATTGCC | 5640 |
| ACCTATGTCT | GAGGAGCTTA | ATGATAAAAT | AGATGACCTC | TCCCAAGAAA | TAAAGGACAG | 5700 |
| GAAGCTTGCT | GAGAAGGTGT | CCCAGGCTGA | GAGCCACGCA | GCTCAGTTGA | ATGACTCATC | 5760 |
| TGCTGTCCTT | GATGGAATCC | TTGATGAGGC | TAAAAACATC | TCCTTCAATG | CCACTGCAGC | 5820 |
| CTTCAAAGCT | TACAGCAATA | TTAAGGACTA | TATTGATGAA | GCTGAGAAAG | TTGCCAAAGA | 5880 |
| AGCCAAAGAT | CTTGCACATG | AAGCTACAAA | ACTGGCAACA | GGTCCTCGGG | GTTTATTAAA | 5940 |
| GGAAGATGCC | AAAGGCTGTC | TTCAGAAAAG | CTTCAGGATT | CTTAACGAAG | CCAAGAAGTT | 6000 |
| AGCAAATGAT | GTAAAAGAAA | ATGAAGACCA | TCTAAATGGC | TTAAAAACCA | GGATAGAAAA | 6060 |
| TGCTGATGCT | AGAAATGGGG | ATCTCTTGAG | AACTTTGAAT | GACACTTTGG | GAAAGTTATC | 6120 |
| AGCTATTCCA | AATGATACAG | CTGCTAAACT | GCAAGCTGTT | AAGGACAAAG | CCAGACAAGC | 6180 |
| CAACGACACA | GCTAAAGATG | TACTGGCACA | GATTACAGAG | CTCCACCAGA | ACCTCGATGG | 6240 |
| CCTGAAGAAG | AATTACAATA | AACTAGCAGA | CAGCGTCGCC | AAAACGAATG | CTGTGGTTAA | 6300 |
| AGATCCTTCC | AAGAACAAAA | TCATTGCCGA | TGCAGATGCC | ACTGTCAAAA | ATTTAGAACA | 6360 |
| GGAAGCTGAC | CGGCTAATAG | ATAAACTCAA | ACCCATCAAG | GAACTTGAGG | ATAACCTAAA | 6420 |
| GAAAACATC | TCTGAGATAA | AGGAATTGAT | AAACCAAGCT | CGGAAACAAG | CCAATTCTAT | 6480 |
| CAAAGTATCT | GTGTCTTCAG | GAGGTGACTG | CATTCGAACA | TACAAACCAG | AAATCAAGAA | 6540 |
| AGGAAGTTAC | AATAATATTG | TTGTCAACGT | AAAGACAGCT | GTTGCTGATA | ACCTCCTCTT | 6600 |
| TTATCTTGGA | AGTGCCAAAT | TTATTGACTT | TCTGGCTATA | GAAATGCGTA | AAGGCAAAGT | 6660 |
| CAGCTTCCTC | TGGGATGTTG | GATCTGGAGT | TGGACGTGTA | GAGTACCCAG | ATTTGACTAT | 6720 |
| TGATGACTCA | TATTGGTACC | GTATCGTAGC | ATCAAGAACT | GGGAGAAATG | GAACTATTTC | 6780 |
| TGTGAGAGCC | CTGGATGGAC | CCAAAGCCAG | CATTGTGCCC | AGCACACACC | ATTCGACGTC | 6840 |
| TCCTCCAGGG | TACACGATTC | TAGATGTGGA | TGCAAATGCA | ATGCTGTTTG | TTGGTGGCCT | 6900 |
| GACTGGGAAA | TTAAAGAAGG | CTGATGCTGT | ACGTGTGATT | AC | | 6942 |

( 2 ) INFORMATION FOR SEQ ID NO:4:

( i ) SEQUENCE CHARACTERISTICS:
        ( A ) LENGTH: 3111 amino acids
        ( B ) TYPE: amino acid
        ( D ) TOPOLOGY: linear ( x i ) SEQUENCE DESCRIPTION: SEQ ID NO:4:

```
Met  Pro  Gly  Ala  Ala  Gly  Val  Leu  Leu  Leu  Leu  Leu  Ser  Gly  Gly
 1                    5                   10                   15

Leu  Gly  Gly  Val  Gln  Ala  Gln  Arg  Pro  Gln  Gln  Gln  Arg  Ser  Gln
                20                   25                   30

Ala  His  Gln  Gln  Arg  Gly  Leu  Phe  Pro  Ala  Val  Leu  Asn  Leu  Ala  Ser
                35                   40                   45

Asn  Ala  Leu  Ile  Thr  Thr  Asn  Ala  Thr  Cys  Gly  Glu  Lys  Gly  Pro  Glu
```

|  |  |  |  |  | 50 |  |  |  |  | 55 |  |  |  |  | 60 |  |  |
|---|---|---|---|---|---|---|---|---|---|---|---|---|---|---|---|---|---|
| Met 65 | Tyr | Cys | Lys | Leu | Val 70 | Glu | His | Val | Pro | Gly 75 | Gln | Pro | Val | Arg | Asn 80 |
| Pro | Gln | Cys | Arg | Ile 85 | Cys | Asn | Gln | Asn | Ser 90 | Ser | Asn | Pro | Asn | Gln 95 | Arg |
| His | Pro | Ile | Thr 100 | Asn | Ala | Ile | Asp | Gly 105 | Lys | Asn | Thr | Trp | Trp 110 | Gln | Ser |
| Pro | Ser | Ile 115 | Lys | Asn | Gly | Ile | Glu 120 | Tyr | His | Tyr | Val | Thr 125 | Ile | Thr | Leu |
| Asp | Leu 130 | Gln | Gln | Val | Phe | Gln 135 | Ile | Ala | Tyr | Val | Ile 140 | Val | Lys | Ala | Ala |
| Asn 145 | Ser | Pro | Arg | Pro | Gly 150 | Asn | Trp | Ile | Leu | Glu 155 | Arg | Ser | Leu | Asp | Asp 160 |
| Val | Glu | Tyr | Lys | Pro 165 | Trp | Gln | Tyr | His | Ala 170 | Val | Thr | Asp | Thr | Glu 175 | Cys |
| Leu | Thr | Leu | Tyr 180 | Asn | Ile | Tyr | Pro | Arg 185 | Thr | Gly | Pro | Pro | Ser 190 | Tyr | Ala |
| Lys | Asp | Asp 195 | Glu | Val | Ile | Cys | Thr 200 | Ser | Phe | Tyr | Ser | Lys 205 | Ile | His | Pro |
| Leu | Glu 210 | Asn | Gly | Glu | Ile | His 215 | Ile | Ser | Leu | Ile | Asn 220 | Gly | Arg | Pro | Ser |
| Ala 225 | Asp | Asp | Pro | Ser | Pro 230 | Glu | Leu | Leu | Glu | Phe 235 | Thr | Ser | Ala | Arg | Tyr 240 |
| Ile | Arg | Leu | Arg | Phe 245 | Gln | Arg | Ile | Arg | Thr 250 | Leu | Asn | Ala | Asp | Leu 255 | Met |
| Met | Phe | Ala | His 260 | Lys | Asp | Pro | Arg | Glu 265 | Ile | Asp | Pro | Ile | Val 270 | Thr | Arg |
| Arg | Tyr | Tyr 275 | Tyr | Ser | Val | Lys | Asp 280 | Ile | Ser | Val | Gly | Gly 285 | Met | Cys | Ile |
| Cys | Tyr 290 | Gly | His | Ala | Arg | Ala 295 | Cys | Pro | Leu | Asp | Pro 300 | Ala | Thr | Asn | Lys |
| Ser 305 | Arg | Cys | Glu | Cys | Glu 310 | His | Asn | Thr | Cys | Gly 315 | Asp | Ser | Cys | Asp | Gln 320 |
| Cys | Cys | Pro | Gly | Phe 325 | His | Gln | Lys | Pro | Trp 330 | Arg | Ala | Gly | Thr | Phe 335 | Leu |
| Thr | Lys | Thr | Glu 340 | Cys | Glu | Ala | Cys | Asn 345 | Cys | His | Gly | Lys | Ala 350 | Glu | Glu |
| Cys | Tyr | Tyr 355 | Asp | Glu | Asn | Val | Ala 360 | Arg | Arg | Asn | Leu | Ser 365 | Leu | Asn | Ile |
| Arg | Gly 370 | Lys | Tyr | Ile | Gly | Gly 375 | Gly | Val | Cys | Ile | Asn 380 | Cys | Thr | Gln | Asn |
| Thr 385 | Ala | Gly | Ile | Asn | Cys 390 | Glu | Thr | Cys | Thr | Asp 395 | Gly | Phe | Phe | Arg | Pro |
| Lys 400 | Gly | Val | Ser | Pro | Asn 405 | Tyr | Pro | Arg | Pro | Cys 410 | Gln | Pro | Cys | His | Cys 415 |
| Asp | Pro | Ile | Gly | Ser 420 | Leu | Asn | Glu | Val | Cys 425 | Val | Lys | Asp | Glu | Lys 430 | His |
| Ala | Arg | Arg | Gly 435 | Leu | Ala | Pro | Gly | Ser 440 | Cys | His | Cys | Lys | Thr 445 | Gly | Phe |
| Gly | Gly | Val 450 | Ser | Cys | Asp | Arg | Cys 455 | Ala | Arg | Gly | Tyr | Thr 460 | Gly | Tyr | Pro |
| Asp | Cys 465 | Lys | Ala | Cys | Asn | Cys 470 | Ser | Gly | Leu | Gly | Ser 475 | Lys | Asn | Glu | Asp |

```
Pro  Cys  Phe  Gly  Pro  Cys  Ile  Cys  Lys  Glu  Asn  Val  Glu  Gly  Gly  Asp
480            485                 490                 495
Cys  Ser  Arg  Cys  Lys  Ser  Gly  Phe  Phe  Asn  Leu  Gln  Glu  Asp  Asn  Trp
               500                 505                           510
Lys  Gly  Cys  Asp  Glu  Cys  Phe  Cys  Ser  Gly  Val  Ser  Asn  Arg  Cys  Gln
     515                 520                      525
Ser  Ser  Tyr  Trp  Thr  Tyr  Gly  Lys  Ile  Gln  Asp  Met  Ser  Gly  Trp  Tyr
530                 535                 540                           545
Leu  Thr  Asp  Leu  Pro  Gly  Arg  Ile  Arg  Val  Ala  Pro  Gln  Gln  Asp  Asp
               550                 555                      560
Leu  Asp  Ser  Pro  Gln  Gln  Ile  Ser  Ile  Ser  Asn  Ala  Glu  Ala  Arg  Gln
               565                 570                      575
Ala  Leu  Pro  His  Ser  Tyr  Tyr  Trp  Ser  Ala  Pro  Ala  Pro  Tyr  Leu  Gly
          580                 585                      590
Asn  Lys  Leu  Pro  Ala  Val  Gly  Gly  Gln  Leu  Thr  Phe  Thr  Ile  Ser  Tyr
     595                 600                 605
Asp  Leu  Glu  Glu  Glu  Glu  Glu  Asp  Thr  Glu  Arg  Val  Leu  Gln  Leu  Met
610                      615                 620                      625
Ile  Ile  Leu  Glu  Gly  Asn  Asp  Leu  Ser  Ile  Ser  Thr  Ala  Gln  Asp  Glu
                    630                      635                      640
Val  Tyr  Leu  His  Pro  Ser  Glu  Glu  His  Thr  Asn  Val  Leu  Leu  Leu  Lys
               645                 650                           655
Glu  Glu  Ser  Phe  Thr  Ile  His  Gly  Thr  His  Phe  Pro  Val  Arg  Arg  Lys
          660                 665                      670
Glu  Phe  Met  Thr  Val  Leu  Ala  Asn  Leu  Lys  Arg  Val  Leu  Leu  Gln  Ile
     675                 680                      685
Thr  Tyr  Ser  Phe  Gly  Met  Asp  Ala  Ile  Phe  Arg  Leu  Ser  Ser  Val  Asn
690                      695                 700                      705
Leu  Glu  Ser  Ala  Val  Ser  Tyr  Pro  Thr  Asp  Gly  Ser  Ile  Ala  Ala  Ala
                    710                 715                      720
Val  Glu  Val  Cys  Gln  Cys  Pro  Pro  Gly  Tyr  Thr  Gly  Ser  Ser  Cys  Glu
               725                 730                      735
Ser  Cys  Trp  Pro  Arg  His  Arg  Arg  Val  Asn  Gly  Thr  Ile  Phe  Gly  Gly
          740                 745                      750
Ile  Cys  Glu  Pro  Cys  Gln  Cys  Phe  Gly  His  Ala  Glu  Ser  Cys  Asp  Asp
755                      760                      765
Val  Thr  Gly  Glu  Cys  Leu  Asn  Cys  Lys  Asp  His  Thr  Gly  Gly  Pro  Tyr
770                 775                 780                      785
Cys  Asp  Lys  Cys  Leu  Pro  Gly  Phe  Tyr  Gly  Glu  Pro  Thr  Lys  Gly  Thr
               790                 795                      800
Ser  Glu  Asp  Cys  Gln  Pro  Cys  Ala  Cys  Pro  Leu  Asn  Ile  Pro  Ser  Asn
               805                 810                      815
Asn  Phe  Ser  Pro  Thr  Cys  His  Leu  Asp  Arg  Ser  Leu  Gly  Leu  Ile  Cys
               820                 825                      830
Asp  Gly  Cys  Pro  Val  Gly  Tyr  Thr  Gly  Pro  Arg  Cys  Glu  Arg  Cys  Ala
     835                 840                 845
Glu  Gly  Tyr  Phe  Gly  Gln  Pro  Ser  Val  Pro  Gly  Gly  Ser  Cys  Gln  Pro
850                 855                 860                           865
Cys  Gln  Cys  Asn  Asp  Asn  Leu  Asp  Phe  Ser  Ile  Pro  Gly  Ser  Cys  Asp
               870                 875                      880
Ser  Leu  Ser  Gly  Ser  Cys  Leu  Ile  Cys  Lys  Pro  Gly  Thr  Thr  Gly  Arg
               885                 890                      895
Tyr  Cys  Glu  Leu  Cys  Ala  Asp  Gly  Tyr  Phe  Gly  Asp  Ala  Val  Asp  Ala
     900                 905                 910
```

```
Lys  Asn  Cys  Gln  Pro  Cys  Arg  Cys  Asn  Ala  Gly  Gly  Ser  Phe  Ser  Glu
     915                 920                      925

Val  Cys  His  Ser  Gln  Thr  Gly  Gln  Cys  Glu  Cys  Arg  Ala  Asn  Val  Gln
930                      935                      940

Gly  Gln  Arg  Cys  Asp  Lys  Cys  Lys  Ala  Gly  Thr  Phe  Gly  Leu  Gln  Ser
945                      950                      955                      960

Ala  Arg  Gly  Cys  Val  Pro  Cys  Asn  Cys  Ser  Phe  Gly  Ser  Lys  Ser
                    965                      970                      975

Phe  Asp  Cys  Glu  Glu  Ser  Gly  Gln  Cys  Trp  Cys  Gln  Pro  Gly  Val  Thr
               980                      985                      990

Gly  Lys  Lys  Cys  Asp  Arg  Cys  Ala  His  Gly  Tyr  Phe  Asn  Phe  Gln  Glu
               995                     1000                     1005

Gly  Gly  Cys  Thr  Ala  Cys  Glu  Cys  Ser  His  Leu  Gly  Asn  Asn  Cys  Asp
     1010                     1015                     1020

Pro  Lys  Thr  Gly  Arg  Cys  Ile  Cys  Pro  Pro  Asn  Thr  Ile  Gly  Glu  Lys
1025                     1030                     1035                     1040

Cys  Ser  Lys  Cys  Ala  Pro  Asn  Thr  Trp  Gly  His  Ser  Ile  Thr  Thr  Gly
                    1045                     1050                     1055

Cys  Lys  Ala  Cys  Asn  Cys  Ser  Thr  Val  Gly  Ser  Leu  Asp  Phe  Gln  Cys
                    1060                     1065                     1070

Asn  Val  Asn  Thr  Gly  Gln  Cys  Asn  Cys  His  Pro  Lys  Phe  Ser  Gly  Ala
          1075                     1080                     1085

Lys  Cys  Thr  Glu  Cys  Ser  Arg  Gly  His  Trp  Asn  Tyr  Pro  Arg  Cys  Asn
     1090                     1095                     1100

Leu  Cys  Asp  Cys  Phe  Leu  Pro  Gly  Thr  Asp  Ala  Thr  Thr  Cys  Asp  Ser
1105                     1110                     1115                     1120

Glu  Thr  Lys  Lys  Cys  Ser  Cys  Ser  Asp  Gln  Thr  Thr  Gly  Gln  Cys  Thr
               1125                     1130                     1135

Cys  Lys  Val  Asn  Val  Glu  Gly  Ile  His  Cys  Asp  Arg  Cys  Arg  Pro  Gly
                    1140                     1145                     1150

Lys  Phe  Gly  Leu  Asp  Ala  Lys  Asn  Pro  Leu  Gly  Cys  Ser  Ser  Cys  Tyr
               1155                     1160                     1165

Cys  Phe  Gly  Thr  Thr  Thr  Gln  Cys  Ser  Glu  Ala  Lys  Gly  Leu  Ile  Arg
     1170                     1175                     1180

Thr  Trp  Val  Thr  Leu  Lys  Ala  Glu  Gln  Thr  Ile  Leu  Pro  Leu  Val  Asp
1185                     1190                     1195                     1200

Glu  Ala  Leu  Gln  His  Thr  Thr  Thr  Lys  Gly  Ile  Val  Phe  Gln  His  Pro
               1205                     1210                     1215

Glu  Ile  Val  Ala  His  Met  Asp  Leu  Met  Arg  Glu  Asp  Leu  His  Leu  Glu
                    1220                     1225                     1230

Pro  Phe  Tyr  Trp  Lys  Leu  Pro  Glu  Gln  Phe  Glu  Gly  Lys  Lys  Leu  Met
               1235                     1240                     1245

Ala  Tyr  Gly  Gly  Lys  Leu  Lys  Tyr  Ala  Ile  Tyr  Phe  Glu  Ala  Arg  Glu
     1250                     1255                     1260

Glu  Thr  Gly  Phe  Ser  Thr  Tyr  Asn  Pro  Gln  Val  Ile  Ile  Arg  Gly  Gly
1265                     1270                     1275                     1280

Thr  Pro  Thr  His  Ala  Arg  Ile  Ile  Val  Arg  His  Met  Ala  Ala  Pro  Leu
               1285                     1290                     1295

Ile  Gly  Gln  Leu  Thr  Arg  His  Glu  Ile  Glu  Met  Thr  Glu  Lys  Glu  Trp
                    1300                     1305                     1310

Lys  Tyr  Tyr  Gly  Asp  Asp  Pro  Arg  Val  His  Arg  Thr  Val  Thr  Arg  Glu
     1315                     1320                     1325

Asp  Phe  Leu  Asp  Ile  Leu  Tyr  Asp  Ile  His  Tyr  Ile  Leu  Ile  Lys  Ala
```

-continued

```
                 1330                    1335                         1340
Thr Tyr Gly Asn Phe Met Arg Gln Ser Arg Ile Ser Glu Ile Ser Met
1345                     1350                    1355                    1360
Glu Val Ala Glu Gln Gly Arg Gly Thr Thr Met Thr Pro Pro Ala Asp
                     1365                    1370                    1375
Leu Ile Glu Lys Cys Asp Cys Pro Leu Gly Tyr Ser Gly Leu Ser Cys
                 1380                    1385                    1390
Glu Ala Cys Leu Pro Gly Phe Tyr Arg Leu Arg Ser Gln Pro Gly Gly
                 1395                    1400                    1405
Arg Thr Pro Gly Pro Thr Leu Gly Thr Cys Val Pro Cys Gln Cys Asn
                 1410                    1415                    1420
Gly His Ser Ser Leu Cys Asp Pro Glu Thr Ser Ile Cys Gln Asn Cys
1425                     1430                    1435                    1440
Gln His His Thr Ala Gly Asp Phe Cys Glu Arg Cys Ala Leu Gly Tyr
                     1445                    1450                    1455
Tyr Gly Ile Val Lys Gly Leu Pro Asn Asp Cys Gln Gln Cys Ala Cys
                 1460                    1465                    1470
Pro Leu Ile Ser Ser Ser Asn Asn Phe Ser Pro Ser Cys Val Ala Glu
                 1475                    1480                    1485
Gly Leu Asp Asp Tyr Arg Cys Thr Ala Cys Pro Arg Gly Tyr Glu Gly
                 1490                    1495                    1500
Gln Tyr Cys Glu Arg Cys Ala Pro Gly Tyr Thr Gly Ser Pro Gly Asn
1505                     1510                    1515                    1520
Pro Gly Gly Ser Cys Gln Glu Cys Glu Cys Asp Pro Tyr Gly Ser Leu
                 1525                    1530                    1535
Pro Val Pro Cys Asp Pro Val Thr Gly Phe Cys Thr Cys Arg Pro Gly
                 1540                    1545                    1550
Ala Thr Gly Arg Lys Cys Asp Gly Cys Lys His Trp His Ala Arg Glu
                 1555                    1560                    1565
Gly Trp Glu Cys Val Phe Cys Gly Asp Glu Cys Thr Gly Leu Leu Leu
                 1570                    1575                    1580
Gly Asp Leu Ala Arg Leu Glu Gln Met Val Met Ser Ile Asn Leu Thr
1585                     1590                    1595                    1600
Gly Pro Leu Pro Ala Pro Tyr Lys Met Leu Tyr Gly Leu Glu Asn Met
                     1605                    1610                    1615
Thr Gln Glu Leu Lys His Leu Leu Ser Pro Gln Arg Ala Pro Glu Arg
                     1620                    1625                    1630
Leu Ile Gln Leu Ala Glu Gly Asn Leu Asn Thr Leu Val Thr Glu Met
                     1635                    1640                    1645
Asn Glu Leu Leu Thr Arg Ala Thr Lys Val Thr Ala Asp Gly Glu Gln
1650                     1655                    1660
Thr Gly Gln Asp Ala Glu Arg Thr Asn Thr Arg Ala Lys Ser Leu Gly
1665                     1670                    1675                    1680
Glu Phe Ile Lys Glu Leu Ala Arg Asp Ala Glu Ala Val Asn Glu Lys
                     1685                    1690                    1695
Ala Ile Lys Leu Asn Glu Thr Leu Gly Thr Arg Asp Glu Ala Phe Glu
                     1700                    1705                    1710
Arg Asn Leu Glu Gly Leu Gln Lys Glu Ile Asp Gln Met Ile Lys Glu
                     1715                    1720                    1725
Leu Arg Arg Lys Asn Leu Glu Thr Gln Lys Glu Ile Ala Glu Asp Glu
                 1730                    1735                    1740
Leu Val Ala Ala Glu Ala Leu Leu Lys Lys Val Lys Lys Leu Phe Gly
1745                     1750                    1755                    1760
```

Glu Ser Arg Gly Glu Asn Glu Glu Met Glu Lys Asp Leu Arg Glu Lys
            1765                1770                1775

Leu Ala Asp Tyr Lys Asn Lys Val Asp Asp Ala Trp Asp Leu Leu Arg
            1780                1785                1790

Glu Ala Thr Asp Lys Ile Arg Glu Ala Asn Arg Leu Phe Ala Val Asn
            1795                1800                1805

Gln Lys Asn Met Thr Ala Leu Glu Lys Lys Lys Glu Ala Val Glu Ser
            1810                1815                1820

Gly Lys Arg Gln Ile Glu Asn Thr Leu Lys Glu Gly Asn Asp Ile Leu
1825                1830                1835                1840

Asp Glu Ala Asn Arg Leu Ala Asp Glu Ile Asn Ser Ile Ile Asp Tyr
                1845                1850                1855

Val Glu Asp Ile Gln Thr Lys Leu Pro Pro Met Ser Glu Glu Leu Asn
            1860                1865                1870

Asp Lys Ile Asp Asp Leu Ser Gln Glu Ile Lys Asp Arg Lys Leu Ala
            1875                1880                1885

Glu Lys Val Ser Gln Ala Glu Ser His Ala Ala Gln Leu Asn Asp Ser
            1890                1895                1900

Ser Ala Val Leu Asp Gly Ile Leu Asp Glu Ala Lys Asn Ile Ser Phe
1905                1910                1915                1920

Asn Ala Thr Ala Ala Phe Lys Ala Tyr Ser Asn Ile Lys Asp Tyr Ile
            1925                1930                1935

Asp Glu Ala Glu Lys Val Ala Lys Glu Ala Lys Asp Leu Ala His Glu
            1940                1945                1950

Ala Thr Lys Leu Ala Thr Gly Pro Arg Gly Leu Leu Lys Glu Asp Ala
            1955                1960                1965

Lys Gly Cys Leu Gln Lys Ser Phe Arg Ile Leu Asn Glu Ala Lys Lys
            1970                1975                1980

Leu Ala Asn Asp Val Lys Glu Asn Glu Asp His Leu Asn Gly Leu Lys
1985                1990                1995                2000

Thr Arg Ile Glu Asn Ala Asp Ala Arg Asn Gly Asp Leu Leu Arg Thr
            2005                2010                2015

Leu Asn Asp Thr Leu Gly Lys Leu Ser Ala Ile Pro Asn Asp Thr Ala
            2020                2025                2030

Ala Lys Leu Gln Ala Val Lys Asp Lys Ala Arg Gln Ala Asn Asp Thr
            2035                2040                2045

Ala Lys Asp Val Leu Ala Gln Ile Thr Glu Leu His Gln Asn Leu Asp
            2050                2055                2060

Gly Leu Lys Lys Asn Tyr Asn Lys Leu Ala Asp Ser Val Ala Lys Thr
2065                2070                2075                2080

Asn Ala Val Val Lys Asp Pro Ser Lys Asn Lys Ile Ile Ala Asp Ala
            2085                2090                2095

Asp Ala Thr Val Lys Asn Leu Glu Gln Glu Ala Asp Arg Leu Ile Asp
            2100                2105                2110

Lys Leu Lys Pro Ile Lys Glu Leu Glu Asp Asn Leu Lys Lys Asn Ile
            2115                2120                2125

Ser Glu Ile Lys Glu Leu Ile Asn Gln Ala Arg Lys Gln Ala Asn Ser
            2130                2135                2140

Ile Lys Val Ser Val Ser Ser Gly Gly Asp Cys Ile Arg Thr Tyr Lys
2145                2150                2155                2160

Pro Glu Ile Lys Lys Gly Ser Tyr Asn Asn Ile Val Val Asn Val Lys
            2165                2170                2175

Thr Ala Val Ala Asp Asn Leu Leu Phe Tyr Leu Gly Ser Ala Lys Phe
            2180                2185                2190

Ile Asp Phe Leu Ala Ile Glu Met Arg Lys Gly Lys Val Ser Phe Leu
            2195                2200                2205

Trp Asp Val Gly Ser Gly Val Gly Arg Val Glu Tyr Pro Asp Leu Thr
            2210                2215                2220

Ile Asp Asp Ser Tyr Trp Tyr Arg Ile Val Ala Ser Arg Thr Gly Arg
2225                2230                2235                2240

Asn Gly Thr Ile Ser Val Arg Ala Leu Asp Gly Pro Lys Ala Ser Ile
            2245                2250                2255

Val Pro Ser Thr His His Ser Thr Ser Pro Pro Gly Tyr Thr Ile Leu
            2260                2265                2270

Asp Val Asp Ala Asn Ala Met Leu Phe Val Gly Gly Leu Thr Gly Lys
            2275                2280                2285

Leu Lys Lys Ala Asp Ala Val Arg Val Ile Thr Phe Thr Gly Cys Met
            2290                2295                2300

Gly Glu Thr Tyr Phe Asp Asn Lys Pro Ile Gly Leu Trp Asn Phe Arg
2305                2310                2315                2320

Glu Lys Glu Gly Asp Cys Lys Gly Cys Thr Val Ser Pro Gln Val Glu
            2325                2330                2335

Asp Ser Glu Gly Thr Ile Gln Phe Asp Gly Glu Gly Tyr Ala Leu Val
            2340                2345                2350

Ser Arg Pro Ile Arg Trp Tyr Pro Asn Ile Ser Thr Val Met Phe Lys
            2355                2360                2365

Phe Arg Thr Phe Ser Ser Ser Ala Leu Leu Met Tyr Leu Ala Thr Arg
            2370                2375                2380

Asp Leu Arg Asp Phe Met Ser Val Glu Leu Thr Asp Gly His Ile Lys
2385                2390                2395                2400

Val Ser Tyr Asp Leu Gly Ser Gly Met Ala Ser Val Val Ser Asn Gln
            2405                2410                2415

Asn His Asn Asp Gly Lys Trp Lys Ser Phe Thr Leu Ser Arg Ile Gln
            2420                2425                2430

Lys Gln Ala Asn Ile Ser Ile Val Asp Ile Asp Thr Asn Gln Glu Glu
            2435                2440                2445

Asn Ile Ala Thr Ser Ser Ser Gly Asn Asn Phe Gly Leu Asp Leu Lys
2450                2455                2460

Ala Asp Asp Lys Ile Tyr Phe Gly Gly Leu Pro Thr Leu Arg Asn Leu
2465                2470                2475                2480

Ser Met Lys Ala Arg Pro Glu Val Asn Leu Lys Lys Tyr Ser Gly Cys
            2485                2490                2495

Leu Lys Asp Ile Glu Ile Ser Arg Thr Pro Tyr Asn Ile Leu Ser Ser
            2500                2505                2510

Pro Asp Tyr Val Gly Val Thr Lys Gly Cys Ser Leu Glu Asn Val Tyr
            2515                2520                2525

Thr Val Ser Phe Pro Lys Pro Gly Phe Val Glu Leu Ser Pro Val Pro
            2530                2535                2540

Ile Asp Val Gly Thr Glu Ile Asn Leu Ser Phe Ser Thr Lys Asn Glu
2545                2550                2555                2560

Ser Gly Ile Ile Leu Leu Gly Ser Gly Gly Thr Pro Ala Pro Pro Arg
            2565                2570                2575

Arg Lys Arg Arg Gln Thr Gly Gln Ala Tyr Tyr Val Ile Leu Leu Asn
            2580                2585                2590

Arg Gly Arg Leu Glu Val His Leu Ser Thr Gly Ala Arg Thr Met Arg
            2595                2600                2605

Lys Ile Val Ile Arg Pro Glu Pro Asn Leu Phe His Asp Gly Arg Glu

```
                    2610                   2615                      2620
His  Ser  Val  His  Val  Glu  Arg  Thr  Arg  Gly  Ile  Phe  Thr  Val  Gln  Val
2625                2630                  2635                      2640

Asp  Glu  Asn  Arg  Arg  Tyr  Met  Gln  Asn  Leu  Thr  Val  Glu  Gln  Pro  Ile
                    2645                  2650                      2655

Glu  Val  Lys  Lys  Leu  Phe  Val  Gly  Gly  Ala  Pro  Pro  Glu  Phe  Gln  Pro
                    2660                  2665                      2670

Ser  Pro  Leu  Arg  Asn  Ile  Pro  Pro  Phe  Glu  Gly  Cys  Ile  Trp  Asn  Leu
                    2675                  2680                      2685

Val  Ile  Asn  Ser  Val  Pro  Met  Asp  Phe  Ala  Arg  Pro  Val  Ser  Phe  Lys
                    2690                  2695                      2700

Asn  Ala  Asp  Ile  Gly  Arg  Cys  Ala  His  Gln  Lys  Leu  Arg  Glu  Asp  Glu
2705                2710                  2715                      2720

Asp  Gly  Ala  Ala  Pro  Ala  Glu  Ile  Val  Ile  Gln  Pro  Glu  Pro  Val  Pro
                    2725                  2730                      2735

Thr  Pro  Ala  Phe  Pro  Thr  Pro  Thr  Pro  Val  Leu  Thr  His  Gly  Pro  Cys
                    2740                  2745                      2750

Ala  Ala  Glu  Ser  Glu  Pro  Ala  Leu  Leu  Ile  Gly  Ser  Lys  Gln  Phe  Gly
                    2755                  2760                      2765

Leu  Ser  Arg  Asn  Ser  His  Ile  Ala  Ile  Ala  Phe  Asp  Asp  Thr  Lys  Val
                    2770                  2775                      2780

Lys  Asn  Arg  Leu  Thr  Ile  Glu  Leu  Glu  Val  Arg  Thr  Glu  Ala  Glu  Ser
2785                2790                  2795                      2800

Gly  Leu  Leu  Phe  Tyr  Met  Ala  Ala  Ile  Asn  His  Ala  Asp  Phe  Ala  Thr
                    2805                  2810                      2815

Val  Gln  Leu  Arg  Asn  Gly  Leu  Pro  Tyr  Phe  Ser  Tyr  Asp  Leu  Gly  Ser
                    2820                  2825                      2830

Gly  Asp  Thr  His  Thr  Met  Ile  Pro  Thr  Lys  Ile  Asn  Asp  Gly  Gln  Trp
                    2835                  2840                      2845

His  Lys  Ile  Lys  Ile  Met  Arg  Ser  Lys  Gln  Glu  Gly  Ile  Leu  Tyr  Val
                    2850                  2855                      2860

Asp  Gly  Ala  Ser  Asn  Arg  Thr  Ile  Ser  Pro  Lys  Lys  Ala  Asp  Ile  Leu
2865                2870                  2875                      2880

Asp  Val  Val  Gly  Met  Leu  Tyr  Val  Gly  Gly  Leu  Pro  Ile  Asn  Tyr  Thr
                    2885                  2890                      2895

Thr  Arg  Arg  Ile  Gly  Pro  Val  Thr  Tyr  Ser  Ile  Asp  Gly  Cys  Val  Arg
                    2900                  2905                      2910

Asn  Leu  His  Met  Ala  Glu  Ala  Pro  Ala  Asp  Leu  Glu  Gln  Pro  Thr  Ser
                    2915                  2920                      2925

Ser  Phe  His  Val  Gly  Thr  Cys  Phe  Ala  Asn  Ala  Gln  Arg  Gly  Thr  Tyr
                    2930                  2935                      2940

Phe  Asp  Gly  Thr  Gly  Phe  Ala  Lys  Ala  Val  Gly  Gly  Phe  Lys  Val  Gly
2945                2950                  2955                      2960

Leu  Asp  Leu  Leu  Val  Glu  Phe  Glu  Phe  Ala  Thr  Thr  Thr  Thr  Thr  Gly
                    2965                  2970                      2975

Val  Leu  Leu  Gly  Ile  Ser  Ser  Gln  Lys  Met  Asp  Gly  Met  Gly  Ile  Glu
                    2980                  2985                      2990

Met  Ile  Asp  Glu  Lys  Leu  Met  Phe  His  Val  Asp  Asn  Gly  Ala  Gly  Arg
                    2995                  3000                      3005

Phe  Thr  Ala  Val  Tyr  Asp  Ala  Gly  Val  Pro  Gly  His  Leu  Cys  Asp  Gly
                    3010                  3015                      3020

Gln  Trp  His  Lys  Val  Thr  Ala  Asn  Lys  Ile  Lys  His  Arg  Ile  Glu  Leu
3025                3030                  3035                      3040
```

-continued

```
Thr  Val  Asp  Gly  Asn  Gln  Val  Glu  Ala  Gln  Ser  Pro  Asn  Pro  Ala  Ser
               3045                3050                3055

Thr  Ser  Ala  Asp  Thr  Asn  Asp  Pro  Val  Phe  Val  Gly  Gly  Phe  Pro  Asp
               3060                3065                3070

Asp  Leu  Lys  Gln  Phe  Gly  Leu  Thr  Thr  Ser  Ile  Pro  Phe  Arg  Gly  Cys
               3075                3080                3085

Ile  Arg  Ser  Leu  Lys  Leu  Thr  Lys  Gly  Thr  Ala  Ser  His  Trp  Arg  Leu
               3090                3095                3100

Ile  Leu  Pro  Arg  Pro  Trp  Asn
3105                3110
```

( 2 ) INFORMATION FOR SEQ ID NO:5:

( i ) SEQUENCE CHARACTERISTICS:
( A ) LENGTH: 3075 amino acids
( B ) TYPE: amino acid
( D ) TOPOLOGY: linear ( x i ) SEQUENCE DESCRIPTION: SEQ ID NO:5:

```
Met  Arg  Gly  Gly  Val  Leu  Leu  Val  Leu  Leu  Cys  Val  Ala  Ala  Gln
1                   5                    10                   15

Cys  Arg  Gln  Arg  Gly  Leu  Phe  Pro  Ala  Ile  Leu  Asn  Leu  Ala  Ser  Asn
               20                  25                  30

Ala  His  Ile  Ser  Thr  Asn  Ala  Thr  Cys  Gly  Glu  Lys  Gly  Pro  Glu  Met
          35                  40                  45

Phe  Cys  Lys  Leu  Val  Glu  His  Val  Pro  Gly  Arg  Pro  Val  Arg  Asn  Pro
     50                  55                  60

Gln  Cys  Arg  Ile  Cys  Asp  Gly  Asn  Ser  Ala  Asn  Pro  Arg  Glu  Arg  His
65                  70                  75                       80

Pro  Ile  Ser  His  Ala  Ile  Asp  Gly  Thr  Asn  Asn  Trp  Trp  Gln  Ser  Pro
               85                  90                       95

Ser  Ile  Gln  Asn  Gly  Arg  Glu  Tyr  His  Trp  Val  Thr  Ile  Thr  Leu  Asp
               100                 105                 110

Leu  Arg  Gln  Val  Phe  Gln  Val  Ala  Tyr  Val  Ile  Ile  Lys  Ala  Ala  Asn
               115                 120                 125

Ala  Pro  Arg  Pro  Gly  Asn  Trp  Ile  Leu  Glu  Arg  Ser  Leu  Asp  Gly  Thr
     130                 135                 140

Thr  Phe  Ser  Pro  Trp  Gln  Tyr  Tyr  Ala  Val  Ser  Asp  Ser  Glu  Cys  Leu
145                 150                 155                      160

Ser  Arg  Tyr  Asn  Ile  Thr  Pro  Arg  Arg  Gly  Pro  Pro  Thr  Tyr  Arg  Ala
               165                 170                 175

Asp  Asp  Glu  Val  Ile  Cys  Thr  Ser  Tyr  Tyr  Ser  Arg  Leu  Val  Pro  Leu
               180                 185                 190

Glu  His  Gly  Glu  Ile  His  Thr  Ser  Leu  Ile  Asn  Gly  Arg  Pro  Ser  Ala
               195                 200                 205

Asp  Asp  Leu  Ser  Pro  Lys  Leu  Leu  Glu  Phe  Thr  Ser  Ala  Arg  Tyr  Ile
     210                 215                 220

Arg  Leu  Arg  Phe  Glu  Arg  Ile  Arg  Thr  Leu  Asn  Ala  Asp  Leu  Met  Thr
225                 230                 235                      240

Leu  Ser  His  Arg  Glu  Pro  Lys  Glu  Leu  Asp  Pro  Met  Leu  Pro  Arg  Arg
               245                 250                 255

Tyr  Tyr  Tyr  Ser  Ile  Lys  Asp  Ile  Ser  Val  Gly  Gly  Met  Cys  Ile  Cys
               260                 265                 270

Tyr  Gly  His  Ala  Ser  Ser  Cys  Pro  Trp  Asp  Glu  Thr  Thr  Lys  Lys  Leu
               275                 280                 285

Gln  Cys  Gln  Cys  Glu  His  Asn  Thr  Cys  Gly  Glu  Ser  Cys  Asn  Arg  Cys
```

|     |     |     |     |     | 290 |     |     |     |     | 295 |     |     |     |     | 300 |     |     |     |     |
|-----|-----|-----|-----|-----|-----|-----|-----|-----|-----|-----|-----|-----|-----|-----|-----|-----|-----|-----|-----|
| Cys 305 | Pro | Gly | Tyr | His | Gln 310 | Gln | Pro | Trp | Arg | Pro 315 | Gly | Thr | Val | Ser | Ser 320 |
| Gly | Asn | Thr | Cys | Glu 325 | Ala | Cys | Asn | Cys | His 330 | Asn | Lys | Ala | Lys | Asp 335 | Cys |
| Tyr | Tyr | Asp | Glu 340 | Ser | Val | Ala | Lys | Gln 345 | Lys | Lys | Ser | Leu | Asn 350 | Thr | Ala |
| Gly | Gln | Phe 355 | Arg | Gly | Gly | Gly | Val 360 | Cys | Ile | Asn | Cys | Leu 365 | Gln | Asn | Thr |
| Met | Gly 370 | Ile | Asn | Cys | Glu | Thr 375 | Cys | Ile | Asp | Gly | Tyr 380 | Tyr | Arg | Pro | His |
| Lys 385 | Val | Ser | Pro | Tyr | Glu 390 | Asp | Glu | Pro | Cys | Arg 395 | Pro | Cys | Asn | Cys | Asp 400 |
| Pro | Val | Gly | Ser | Leu 405 | Ser | Ser | Val | Cys | Ile 410 | Lys | Asp | Asp | Leu | His 415 | Ser |
| Asp | Leu | Glu | Asn 420 | Gly | Lys | Gln | Pro | Gly 425 | Gln | Cys | Pro | Cys | Lys 430 | Glu | Gly |
| Tyr | Thr | Gly 435 | Glu | Lys | Cys | Asp | Arg 440 | Cys | Gln | Leu | Gly | Tyr 445 | Lys | Asp | Tyr |
| Pro | Thr 450 | Cys | Val | Ser | Cys 455 | Gly | Cys | Asn | Pro | Val 460 | Gly | Ser | Ala | Ser | Asp |
| Glu 465 | Pro | Cys | Thr | Gly | Pro 470 | Cys | Val | Cys | Lys | Glu 475 | Asn | Val | Glu | Gly | Lys 480 |
| Ala | Cys | Asp | Arg | Cys 485 | Lys | Pro | Gly | Phe | Tyr 490 | Asn | Leu | Lys | Glu | Lys 495 | Asn |
| Pro | Arg | Gly | Cys 500 | Ser | Glu | Cys | Phe | Cys 505 | Phe | Gly | Val | Ser | Asp 510 | Val | Cys |
| Ser | Ser | Leu 515 | Ser | Trp | Pro | Leu | Gly 520 | Gln | Val | Asn | Ser | Met 525 | Ser | Gly | Trp |
| Leu | Val 530 | Thr | Asp | Leu | Ile | Ser 535 | Pro | Arg | Lys | Ile | Pro 540 | Ser | Gln | Gln | Asp |
| Ala 545 | Leu | Gly | Gly | Arg | His 550 | Gln | Val | Ser | Ile | Asn 555 | Asn | Thr | Ala | Val | Met 560 |
| Gln | Arg | Leu | Ala | Pro 565 | Lys | Tyr | Tyr | Trp | Ala 570 | Ala | Pro | Glu | Ala | Tyr 575 | Leu |
| Gly | Asn | Lys | Leu 580 | Thr | Ala | Phe | Gly | Gly 585 | Phe | Leu | Lys | Tyr | Thr 590 | Val | Ser |
| Tyr | Asp | Ile 595 | Pro | Val | Glu | Thr | Val 600 | Asp | Ser | Asn | Leu | Met 605 | Ser | His | Ala |
| Asp | Val 610 | Ile | Ile | Lys | Gly | Asn 615 | Gly | Leu | Thr | Leu | Ser 620 | Thr | Gln | Ala | Glu |
| Gly 625 | Leu | Ser | Leu | Gln | Pro 630 | Tyr | Glu | Glu | Tyr | Leu 635 | Asn | Val | Val | Arg | Leu 640 |
| Val | Pro | Glu | Asn | Phe 645 | Gln | Asp | Phe | His | Ser 650 | Lys | Arg | Gln | Ile | Asp 655 | Arg |
| Asp | Gln | Leu | Met 660 | Thr | Val | Leu | Ala | Asn 665 | Val | Thr | His | Leu | Leu 670 | Ile | Arg |
| Ala | Thr | Tyr 675 | Asn | Ser | Ala | Lys | Met 680 | Ala | Leu | Tyr | Arg | Leu 685 | Glu | Ser | Val |
| Ser | Leu 690 | Asp | Ile | Ala | Ser | Ser 695 | Asn | Ala | Ile | Asp | Leu 700 | Val | Val | Ala | Ala |
| Asp 705 | Val | Glu | His | Cys | Glu 710 | Cys | Pro | Gln | Gly | Tyr 715 | Thr | Gly | Thr | Ser | Cys 720 |

```
Glu  Ser  Cys  Leu  Ser  Gly  Tyr  Tyr  Arg  Val  Asp  Gly  Ile  Leu  Phe  Gly
               725                      730                      735

Gly  Ile  Cys  Gln  Pro  Cys  Glu  Cys  His  Gly  His  Ala  Ala  Glu  Cys  Asn
               740                      745                      750

Val  His  Gly  Val  Cys  Ile  Ala  Cys  Ala  His  Asn  Thr  Thr  Gly  Val  His
          755                      760                      765

Cys  Glu  Gln  Cys  Leu  Pro  Gly  Phe  Tyr  Gly  Glu  Pro  Ser  Arg  Gly  Thr
770                      775                      780

Pro  Gly  Asp  Cys  Gln  Pro  Cys  Ala  Cys  Pro  Leu  Thr  Ile  Ala  Ser  Asn
785                      790                      795                      800

Asn  Phe  Ser  Pro  Thr  Cys  His  Leu  Asn  Asp  Gly  Asp  Glu  Val  Val  Cys
                    805                      810                           815

Asp  Trp  Cys  Ala  Pro  Gly  Tyr  Ser  Gly  Ala  Trp  Cys  Glu  Arg  Cys  Ala
               820                      825                      830

Asp  Gly  Tyr  Tyr  Gly  Asn  Pro  Thr  Val  Pro  Gly  Glu  Ser  Cys  Val  Pro
          835                      840                      845

Cys  Asp  Cys  Ser  Gly  Asn  Val  Asp  Pro  Ser  Glu  Ala  Gly  His  Cys  Asp
850                      855                      860

Ser  Val  Thr  Gly  Glu  Cys  Leu  Lys  Cys  Leu  Gly  Asn  Thr  Asp  Gly  Ala
865                      870                      875                      880

His  Cys  Glu  Arg  Cys  Ala  Asp  Gly  Phe  Tyr  Gly  Asp  Ala  Val  Thr  Ala
               885                      890                      895

Lys  Asn  Cys  Arg  Ala  Cys  Glu  Cys  His  Val  Lys  Gly  Ser  His  Ser  Ala
               900                      905                      910

Val  Cys  His  Leu  Glu  Thr  Gly  Leu  Cys  Asp  Cys  Lys  Pro  Asn  Val  Thr
          915                      920                      925

Gly  Gln  Gln  Cys  Asp  Gln  Cys  Leu  His  Gly  Tyr  Tyr  Gly  Leu  Asp  Ser
930                      935                      940

Gly  His  Gly  Cys  Arg  Pro  Cys  Asn  Cys  Ser  Val  Ala  Gly  Ser  Val  Ser
945                      950                      955                      960

Asp  Gly  Cys  Thr  Asp  Glu  Gly  Gln  Cys  His  Cys  Val  Pro  Gly  Val  Ala
               965                      970                      975

Gly  Lys  Arg  Cys  Asp  Arg  Cys  Ala  His  Gly  Phe  Tyr  Ala  Tyr  Gln  Asp
               980                      985                      990

Gly  Ser  Cys  Thr  Pro  Cys  Asp  Cys  Pro  His  Thr  Gln  Asn  Thr  Cys  Asp
          995                      1000                     1005

Pro  Glu  Thr  Gly  Glu  Cys  Val  Cys  Pro  Pro  His  Thr  Gln  Gly  Val  Lys
1010                     1015                     1020

Cys  Glu  Glu  Cys  Glu  Asp  Gly  His  Trp  Gly  Tyr  Asp  Ala  Glu  Val  Gly
1025                     1030                     1035                     1040

Cys  Gln  Ala  Cys  Asn  Cys  Ser  Leu  Val  Gly  Ser  Thr  His  His  Arg  Cys
                    1045                     1050                     1055

Asp  Val  Val  Thr  Gly  His  Cys  Gln  Cys  Lys  Ser  Lys  Phe  Gly  Gly  Arg
               1060                     1065                     1070

Ala  Cys  Val  Gln  Cys  Ser  Leu  Gly  Tyr  Arg  Asp  Phe  Pro  Asp  Cys  Val
          1075                     1080                     1085

Pro  Cys  Asp  Cys  Asp  Leu  Arg  Gly  Thr  Ser  Gly  Asp  Ala  Cys  Asn  Leu
     1090                     1095                     1100

Glu  Gln  Gly  Leu  Cys  Gly  Cys  Val  Glu  Glu  Thr  Gly  Ala  Cys  Pro  Cys
1105                     1110                     1115                     1120

Lys  Glu  Asn  Val  Phe  Gly  Pro  Gln  Cys  Asn  Glu  Cys  Arg  Glu  Gly  Thr
               1125                     1130                     1135

Phe  Ala  Leu  Arg  Ala  Asp  Asn  Pro  Leu  Gly  Cys  Ser  Pro  Cys  Phe  Cys
               1140                     1145                     1150
```

Ser Gly Leu Ser His Leu Cys Ser Glu Leu Glu Asp Tyr Val Arg Thr
          1155                1160                1165

Pro Val Thr Leu Gly Ser Asp Gln Pro Leu Leu Arg Val Val Ser Gln
     1170                1175                1180

Ser Asn Leu Arg Gly Thr Thr Glu Gly Val Tyr Tyr Gln Ala Pro Asp
1185                1190                1195                1200

Phe Leu Leu Asp Ala Ala Thr Val Arg Gln His Ile Arg Ala Glu Pro
               1205                1210                1215

Phe Tyr Trp Arg Leu Pro Gln Gln Phe Gln Gly Asp Gln Leu Met Ala
          1220                1225                1230

Tyr Gly Gly Lys Leu Lys Tyr Ser Val Ala Phe Tyr Ser Leu Asp Gly
          1235                1240                1245

Val Gly Thr Ser Asn Phe Glu Pro Gln Val Leu Ile Lys Gly Gly Arg
          1250                1255                1260

Ile Arg Lys Gln Val Ile Tyr Met Asp Ala Pro Ala Pro Glu Asn Gly
1265                1270                1275                1280

Val Arg Gln Glu Gln Glu Val Ala Met Arg Glu Asn Phe Trp Lys Tyr
               1285                1290                1295

Phe Asn Ser Val Ser Glu Lys Pro Val Thr Arg Glu Asp Phe Met Ser
               1300                1305                1310

Val Leu Ser Asp Ile Glu Tyr Ile Leu Ile Lys Ala Ser Tyr Gly Gln
               1315                1320                1325

Gly Leu Gln Gln Ser Arg Ile Ser Asp Ile Ser Met Glu Val Gly Arg
          1330                1335                1340

Lys Ala Glu Lys Leu His Pro Glu Glu Glu Val Ala Ser Leu Leu Glu
1345                1350                1355                1360

Asn Cys Val Cys Pro Pro Gly Thr Val Gly Phe Ser Cys Gln Asp Cys
               1365                1370                1375

Ala Pro Gly Tyr His Arg Gly Lys Leu Pro Ala Gly Ser Asp Arg Gly
          1380                1385                1390

Pro Arg Pro Leu Val Ala Pro Cys Val Pro Cys Ser Cys Asn Asn His
          1395                1400                1405

Ser Asp Thr Cys Asp Pro Asn Thr Gly Lys Cys Leu Asn Cys Gly Asp
     1410                1415                1420

Asn Thr Ala Gly Asp His Cys Asp Val Cys Thr Ser Gly Tyr Tyr Gly
1425                1430                1435                1440

Lys Val Thr Gly Ser Ala Ser Asp Cys Ala Leu Cys Ala Cys Pro His
               1445                1450                1455

Ser Pro Pro Ala Ser Phe Ser Pro Thr Cys Val Leu Glu Gly Asp His
               1460                1465                1470

Asp Phe Arg Cys Asp Ala Cys Leu Leu Gly Tyr Glu Gly Lys His Cys
          1475                1480                1485

Glu Arg Cys Ser Ser Ser Tyr Tyr Gly Asn Pro Gln Thr Pro Gly Gly
     1490                1495                1500

Ser Cys Gln Lys Cys Asp Cys Asn Pro His Gly Ser Val His Gly Asp
1505                1510                1515                1520

Cys Asp Arg Thr Ser Gly Gln Cys Val Cys Arg Leu Gly Ala Ser Gly
               1525                1530                1535

Leu Arg Cys Asp Glu Cys Glu Pro Arg His Ile Leu Met Glu Thr Asp
               1540                1545                1550

Cys Val Ser Cys Asp Asp Glu Cys Val Gly Val Leu Leu Asn Asp Leu
          1555                1560                1565

Asp Glu Ile Gly Asp Ala Val Leu Ser Leu Asn Leu Thr Gly Ile Ile

```
                         1570                    1575                   1580
Pro  Val  Pro  Tyr  Gly  Ile  Leu  Ser  Asn  Leu  Glu  Asn  Thr  Thr  Lys  Tyr
1585                     1590                   1595                    1600

Leu  Gln  Glu  Ser  Leu  Leu  Lys  Glu  Asn  Met  Gln  Lys  Asp  Leu  Gly  Lys
                         1605                   1610                    1615

Ile  Lys  Leu  Glu  Gly  Val  Ala  Glu  Thr  Asp  Asn  Leu  Gln  Lys  Lys
                         1620                   1625                    1630

Leu  Thr  Arg  Met  Leu  Ala  Ser  Thr  Gln  Lys  Val  Asn  Arg  Ala  Thr  Glu
                  1635                   1640                   1645

Arg  Ile  Phe  Lys  Glu  Ser  Gln  Asp  Leu  Ala  Val  Ala  Ile  Glu  Arg  Leu
                  1650                   1655                   1660

Gln  Met  Ser  Ile  Thr  Glu  Ile  Met  Glu  Lys  Thr  Thr  Leu  Asn  Gln  Thr
1665                     1670                   1675                    1680

Leu  Asp  Glu  Asp  Phe  Leu  Leu  Pro  Asn  Ser  Thr  Leu  Gln  Asn  Met  Gln
                  1685                   1690                   1695

Gln  Asn  Gly  Thr  Ser  Leu  Leu  Glu  Ile  Met  Gln  Ile  Arg  Asp  Phe  Thr
                  1700                   1705                   1710

Gln  Leu  His  Gln  Asn  Ala  Thr  Leu  Glu  Leu  Lys  Ala  Ala  Glu  Asp  Leu
                  1715                   1720                   1725

Leu  Ser  Gln  Ile  Gln  Glu  Asn  Tyr  Gln  Lys  Pro  Leu  Glu  Glu  Leu  Glu
                  1730                   1735                   1740

Val  Leu  Lys  Glu  Ala  Ala  Ser  His  Val  Leu  Ser  Lys  His  Asn  Asn  Glu
1745                     1750                   1755                    1760

Leu  Lys  Ala  Ala  Glu  Ala  Leu  Val  Arg  Glu  Ala  Glu  Ala  Lys  Met  Gln
                         1765                   1770                    1775

Glu  Ser  Asn  His  Leu  Leu  Leu  Met  Val  Asn  Ala  Asn  Leu  Arg  Glu  Phe
                  1780                   1785                   1790

Ser  Asp  Lys  Lys  Leu  His  Val  Gln  Glu  Gln  Asn  Leu  Thr  Ser  Glu
                  1795                   1800                   1805

Leu  Ile  Val  Gln  Gly  Arg  Gly  Leu  Ile  Asp  Ala  Ala  Ala  Gln  Thr
                  1810                   1815                   1820

Asp  Ala  Val  Gln  Asp  Ala  Leu  Glu  His  Leu  Glu  Asp  His  Gln  Asp  Lys
1825                     1830                   1835                    1840

Leu  Leu  Leu  Trp  Ser  Ala  Lys  Ile  Arg  His  His  Ile  Asp  Asp  Leu  Val
                  1845                   1850                   1855

Met  His  Met  Ser  Gln  Arg  Asn  Ala  Val  Asp  Leu  Val  Tyr  Arg  Ala  Glu
                  1860                   1865                   1870

Asp  His  Ala  Thr  Glu  Phe  Gln  Arg  Leu  Ala  Asp  Val  Leu  Tyr  Ser  Gly
                  1875                   1880                   1885

Leu  Glu  Asn  Ile  Arg  Asn  Val  Ser  Leu  Asn  Ala  Thr  Ser  Ala  Ala  Tyr
                  1890                   1895                   1900

Val  His  Tyr  Asn  Ile  Gln  Ser  Leu  Ile  Glu  Glu  Ser  Glu  Glu  Leu  Ala
1905                     1910                   1915                    1920

Arg  Asp  Ala  His  Arg  Thr  Val  Thr  Glu  Thr  Ser  Leu  Leu  Ser  Glu  Ser
                  1925                   1930                   1935

Leu  Val  Ser  Asn  Gly  Lys  Ala  Ala  Val  Gln  Arg  Ser  Ser  Arg  Phe  Leu
                  1940                   1945                   1950

Lys  Glu  Gly  Asn  Asn  Leu  Ser  Arg  Lys  Leu  Pro  Gly  Ile  Ala  Leu  Glu
                  1955                   1960                   1965

Leu  Ser  Glu  Leu  Arg  Asn  Lys  Thr  Asn  Arg  Phe  Gln  Glu  Asn  Ala  Val
                  1970                   1975                   1980

Glu  Ile  Thr  Arg  Gln  Thr  Asn  Glu  Ser  Leu  Leu  Ile  Leu  Arg  Ala  Ile
1985                     1990                   1995                    2000
```

-continued

```
Pro Glu Gly Ile Arg Asp Lys Gly Ala Lys Thr Lys Glu Leu Ala Thr
                2005                2010                2015
Ser Ala Ser Gln Ser Ala Val Ser Thr Leu Arg Asp Val Ala Gly Leu
                2020                2025                2030
Ser Gln Glu Leu Leu Asn Thr Ser Ala Ser Leu Ser Arg Val Asn Thr
                2035                2040                2045
Thr Leu Arg Glu Thr His Gln Leu Leu Gln Asp Ser Thr Met Ala Thr
                2050                2055                2060
Leu Leu Ala Gly Arg Lys Val Lys Asp Val Glu Ile Gln Ala Lys Val
2065                2070                2075                2080
Leu Phe Asp Arg Leu Lys Pro Leu Lys Met Leu Glu Glu Asn Leu Ser
                2085                2090                2095
Arg Asn Leu Ser Glu Ile Lys Leu Leu Ile Ser Gln Ala Arg Lys Gln
                2100                2105                2110
Ala Ala Ser Ile Lys Val Ala Val Ser Ala Asp Arg Asp Cys Ile Arg
                2115                2120                2125
Ala Tyr Gln Pro Gln Ile Ser Ser Thr Asn Tyr Asn Thr Leu Thr Leu
                2130                2135                2140
Asn Val Lys Thr Gln Glu Pro Asp Asn Leu Leu Phe Tyr Leu Gly Ser
2145                2150                2155                2160
Ser Thr Ala Ser Asp Phe Leu Ala Val Glu Met Arg Arg Gly Arg Val
                2165                2170                2175
Ala Phe Leu Trp Asp Leu Gly Ser Gly Ser Thr Arg Leu Glu Phe Pro
                2180                2185                2190
Asp Phe Pro Ile Asp Asp Asn Arg Trp His Ser Ile His Val Ala Arg
                2195                2200                2205
Phe Gly Asn Ile Gly Ser Leu Ser Val Lys Glu Met Ser Ser Asn Gln
                2210                2215                2220
Lys Ser Pro Thr Lys Thr Ser Lys Ser Pro Gly Thr Ala Asn Val Leu
2225                2230                2235                2240
Asp Val Asn Asn Ser Thr Leu Met Phe Val Gly Gly Leu Gly Gly Gln
                2245                2250                2255
Ile Lys Lys Ser Pro Ala Val Lys Val Thr His Phe Lys Gly Cys Leu
                2260                2265                2270
Gly Glu Ala Phe Leu Asn Gly Lys Ser Ile Gly Leu Trp Asn Tyr Ile
                2275                2280                2285
Glu Arg Glu Gly Lys Cys Arg Gly Cys Phe Gly Ser Ser Gln Asn Glu
                2290                2295                2300
Asp Pro Ser Phe His Phe Asp Gly Ser Gly Tyr Ser Val Val Glu Lys
2305                2310                2315                2320
Ser Leu Pro Ala Thr Val Thr Gln Ile Ile Met Leu Phe Asn Thr Phe
                2325                2330                2335
Ser Pro Asn Gly Leu Leu Leu Tyr Leu Gly Ser Tyr Gly Thr Lys Asp
                2340                2345                2350
Phe Leu Ser Ile Glu Leu Phe Arg Gly Arg Val Lys Val Met Thr Asp
                2355                2360                2365
Leu Gly Ser Gly Pro Ile Thr Leu Leu Thr Asp Arg Arg Tyr Asn Asn
                2370                2375                2380
Gly Thr Trp Tyr Lys Ile Ala Phe Gln Arg Asn Arg Lys Gln Gly Val
2385                2390                2395                2400
Leu Ala Val Ile Asp Ala Tyr Asn Thr Ser Asn Lys Glu Thr Lys Gln
                2405                2410                2415
Gly Glu Thr Pro Gly Ala Ser Ser Asp Leu Asn Arg Leu Asp Lys Asp
                2420                2425                2430
```

```
Pro Ile Tyr Val Gly Gly Leu Pro Arg Ser Arg Val Val Arg Arg Gly
        2435                2440                    2445

Val Thr Thr Lys Ser Phe Val Gly Cys Ile Lys Asn Leu Glu Ile Ser
2450                2455                2460

Arg Ser Thr Phe Asp Leu Leu Arg Asn Ser Tyr Gly Val Arg Lys Gly
2465            2470                2475                    2480

Cys Leu Leu Glu Pro Ile Arg Ser Val Ser Phe Leu Lys Gly Gly Tyr
            2485                2490                    2495

Ile Glu Leu Pro Pro Lys Ser Leu Ser Pro Glu Ser Glu Trp Leu Val
            2500                2505                2510

Thr Phe Ala Thr Thr Asn Ser Ser Gly Ile Ile Leu Ala Ala Leu Gly
        2515                2520                2525

Gly Asp Val Glu Lys Arg Gly Asp Arg Glu Glu Ala His Val Pro Phe
    2530                2535                2540

Phe Ser Val Met Leu Ile Gly Gly Asn Ile Glu Val His Val Asn Pro
2545                2550                2555                2560

Gly Asp Gly Thr Gly Leu Arg Lys Ala Leu Leu His Ala Pro Thr Gly
                2565                2570                2575

Thr Cys Ser Asp Gly Gln Ala His Ser Ile Ser Leu Val Arg Asn Arg
            2580                2585                2590

Arg Ile Ile Thr Val Gln Leu Asp Glu Asn Asn Pro Val Glu Met Lys
        2595                2600                    2605

Leu Gly Thr Leu Val Glu Ser Arg Thr Ile Asn Val Ser Asn Leu Tyr
            2610                2615                2620

Val Gly Gly Ile Pro Glu Gly Glu Gly Thr Ser Leu Leu Thr Met Arg
2625                2630                2635                2640

Arg Ser Phe His Gly Cys Ile Lys Asn Leu Ile Phe Asn Leu Glu Leu
                2645                2650                    2655

Leu Asp Phe Asn Ser Ala Val Gly His Glu Gln Val Asp Leu Asp Thr
            2660                2665                2670

Cys Trp Leu Ser Glu Arg Pro Lys Leu Ala Pro Asp Ala Glu Asp Ser
            2675                2680                2685

Lys Leu Leu Arg Glu Pro Arg Ala Phe Pro Glu Gln Cys Val Val Asp
2690                2695                2700

Ala Ala Leu Glu Tyr Val Pro Gly Ala His Gln Phe Gly Leu Thr Gln
2705                2710                2715                    2720

Asn Ser His Phe Ile Leu Pro Phe Asn Gln Ser Ala Val Arg Lys Lys
                2725                2730                    2735

Leu Ser Val Glu Leu Ser Ile Arg Thr Leu Ala Ser Ser Gly Leu Ile
            2740                2745                2750

Tyr Tyr Met Ala His Gln Asn Gln Ala Asp Tyr Ala Val Leu Gln Leu
            2755                2760                2765

His Gly Gly Arg Leu His Phe Met Phe Asp Leu Gly Lys Gly Arg Thr
        2770                2775                2780

Lys Val Ser His Pro Ala Leu Leu Ser Asp Gly Lys Trp His Thr Val
2785                2790                2795                2800

Lys Thr Asp Tyr Val Lys Arg Lys Gly Phe Ile Thr Val Asp Gly Arg
            2805                2810                    2815

Glu Ser Pro Met Val Thr Val Val Gly Asp Gly Thr Met Leu Asp Val
            2820                2825                2830

Glu Gly Leu Phe Tyr Leu Gly Gly Leu Pro Ser Gln Tyr Gln Ala Arg
        2835                2840                2845

Lys Ile Gly Asn Ile Thr His Ser Ile Pro Ala Cys Ile Gly Asp Val
```

|   |   |   | 2850 |   |   |   |   | 2855 |   |   |   |   | 2860 |   |
|---|---|---|------|---|---|---|---|------|---|---|---|---|------|---|

Thr Val Asn Ser Lys Gln Leu Asp Lys Asp Ser Pro Val Ser Ala Phe
2865                2870            2875              2880

Thr Val Asn Arg Cys Tyr Ala Val Ala Gln Glu Gly Thr Tyr Phe Asp
                2885            2890            2895

Gly Ser Gly Tyr Ala Ala Leu Val Lys Glu Gly Tyr Lys Val Gln Ser
            2900            2905            2910

Asp Val Asn Ile Thr Leu Glu Phe Arg Thr Ser Ser Gln Asn Gly Val
            2915            2920            2925

Leu Leu Gly Ile Ser Thr Ala Lys Val Asp Ala Ile Gly Leu Glu Leu
            2930            2935            2940

Val Asp Gly Lys Val Leu Phe His Val Asn Asn Gly Ala Gly Arg Ile
2945                2950            2955                2960

Thr Pro Ala Tyr Glu Pro Lys Thr Ala Thr Val Leu Cys Asp Gly Lys
                2965            2970            2975

Trp His Thr Leu Gln Ala Asn Lys Ser Lys His Arg Ile Thr Leu Ile
            2980            2985            2990

Val Asp Gly Asn Ala Val Gly Ala Glu Ser Pro His Thr Gln Ser Thr
            2995            3000            3005

Ser Val Asp Thr Asn Asn Pro Ile Tyr Val Gly Gly Tyr Pro Ala Gly
3010                3015            3020

Val Lys Gln Lys Cys Leu Arg Ser Gln Thr Ser Phe Arg Gly Cys Leu
3025            3030            3035            3040

Arg Lys Leu Ala Leu Ile Lys Ser Pro Gln Val Gln Ser Leu Asp Phe
                3045            3050            3055

Ser Arg Ala Phe Glu Leu His Gly Val Phe Leu His Ser Cys Pro Gly
                3060            3065            3070

Pro Ser Pro
        3075

(2) INFORMATION FOR SEQ ID NO:6:

(i) SEQUENCE CHARACTERISTICS:
        (A) LENGTH: 249 amino acids
        (B) TYPE: amino acid
        (D) TOPOLOGY: linear (xi) SEQUENCE DESCRIPTION: SEQ ID NO:6:

Gln Glu Pro Glu Phe Ser Tyr Gly Cys Ala Glu Gly Ser Cys Tyr Pro
1               5                   10                  15

Ala Thr Gly Asp Leu Leu Ile Gly Arg Ala Gln Lys Leu Ser Val Thr
            20              25                  30

Ser Thr Cys Gly Leu His Lys Pro Glu Pro Tyr Cys Ile Val Ser His
        35              40                  45

Leu Gln Glu Asp Lys Lys Cys Phe Ile Cys Asn Ser Gln Asp Pro Tyr
    50              55                  60

His Glu Thr Leu Asn Pro Asp Ser His Leu Ile Glu Asn Val Val Thr
65              70                  75                  80

Thr Phe Ala Pro Asn Arg Leu Lys Ile Trp Trp Gln Ser Glu Asn Gly
                85                  90                  95

Val Glu Asn Val Thr Ile Gln Leu Asp Leu Glu Ala Glu Phe His Phe
            100                 105                 110

Thr His Leu Ile Met Thr Phe Lys Thr Phe Arg Pro Ala Ala Met Leu
        115                 120                 125

Ile Glu Arg Ser Ser Asp Phe Gly Lys Thr Trp Gly Val Tyr Arg Tyr
        130                 135                 140

|     |     |     |     |     |     |     |     |     |     |     |     |     |     |     |     |
| --- | --- | --- | --- | --- | --- | --- | --- | --- | --- | --- | --- | --- | --- | --- | --- |
| Phe 145 | Ala | Tyr | Asp | Cys 150 | Glu | Ala | Ser | Phe | Pro 155 | Ile | Ser | Thr | Gly | Pro 160 |  |
| Met | Lys | Lys | Val | Asp 165 | Asp | Ile | Ile | Cys | Asp 170 | Ser | Arg | Tyr | Ser | Asp 175 | Ile |
| Glu | Pro | Ser | Thr 180 | Glu | Gly | Glu | Val | Ile 185 | Phe | Arg | Ala | Leu | Asp 190 | Pro | Ala |
| Phe | Lys | Ile 195 | Glu | Asp | Pro | Tyr | Ser 200 | Pro | Arg | Ile | Gln | Asn 205 | Leu | Leu | Lys |
| Ile | Thr 210 | Asn | Leu | Arg | Ile | Lys 215 | Phe | Val | Lys | Leu | His 220 | Thr | Leu | Gly | Asp |
| Asn 225 | Leu | Leu | Asp | Ser | Arg 230 | Met | Glu | Ile | Arg | Glu 235 | Lys | Tyr | Tyr | Tyr | Ala 240 |
| Val | Tyr | Asp | Met | Val 245 | Val | Arg | Gly | Asn |  |  |  |  |  |  |  |

(2) INFORMATION FOR SEQ ID NO:7:

(i) SEQUENCE CHARACTERISTICS:
        (A) LENGTH: 250 amino acids
        (B) TYPE: amino acid
        (D) TOPOLOGY: linear (xi) SEQUENCE DESCRIPTION: SEQ ID NO:7:

|     |     |     |     |     |     |     |     |     |     |     |     |     |     |     |     |
| --- | --- | --- | --- | --- | --- | --- | --- | --- | --- | --- | --- | --- | --- | --- | --- |
| Gln 1 | Val | Pro | Ser | Leu 5 | Asp | Val | Pro | Gly | Cys 10 | Ser | Arg | Gly | Ser | Cys 15 | Tyr |
| Pro | Ala | Thr | Gly 20 | Asp | Leu | Leu | Val | Gly 25 | Arg | Ala | Asp | Arg | Leu 30 | Thr | Ala |
| Ser | Ser | Thr 35 | Cys | Gly | Leu | His | Ser 40 | Pro | Gln | Pro | Tyr | Cys 45 | Ile | Val | Ser |
| His | Leu 50 | Gln | Asp | Glu | Lys | Lys 55 | Cys | Phe | Leu | Cys | Asp 60 | Ser | Arg | Arg | Pro |
| Phe 65 | Ser | Ala | Arg | Asp | Asn 70 | Pro | Asn | Ser | His | Arg 75 | Ile | Gln | Asn | Val | Val 80 |
| Thr | Ser | Phe | Ala | Pro 85 | Gln | Arg | Arg | Thr | Ala 90 | Trp | Trp | Gln | Ser | Glu 95 | Asn |
| Gly | Val | Pro | Met 100 | Val | Thr | Ile | Gln | Leu 105 | Asp | Leu | Glu | Ala | Glu 110 | Phe | His |
| Phe | Thr | His 115 | Leu | Ile | Met | Thr | Phe 120 | Lys | Thr | Phe | Arg | Pro 125 | Ala | Ala | Met |
| Leu | Val 130 | Glu | Arg | Ser | Ala | Asp 135 | Phe | Gly | Arg | Thr | Trp 140 | Arg | Val | Tyr | Arg |
| Tyr 145 | Phe | Ser | Tyr | Asp | Cys 150 | Gly | Ala | Asp | Phe | Pro 155 | Gly | Ile | Pro | Leu | Ala 160 |
| Pro | Pro | Arg | Arg | Trp 165 | Asp | Asp | Val | Val | Cys 170 | Glu | Ser | Arg | Tyr | Ser 175 | Glu |
| Ile | Glu | Pro | Ser 180 | Thr | Glu | Gly | Glu | Val 185 | Ile | Tyr | Arg | Val | Leu 190 | Asp | Pro |
| Ala | Ile | Pro 195 | Ile | Pro | Asp | Pro | Tyr 200 | Ser | Ser | Arg | Ile | Gln 205 | Asn | Leu | Leu |
| Lys | Ile 210 | Thr | Asn | Leu | Arg | Val 215 | Asn | Leu | Thr | Arg | Leu 220 | His | Thr | Leu | Gly |
| Asp 225 | Asn | Leu | Leu | Asp | Pro 230 | Arg | Arg | Glu | Ile | Arg 235 | Glu | Lys | Tyr | Tyr | Tyr 240 |
| Ala | Leu | Tyr | Glu | Leu 245 | Val | Ile | Arg | Gly | Asn 250 |  |  |  |  |  |  |

( 2 ) INFORMATION FOR SEQ ID NO:8:

( i ) SEQUENCE CHARACTERISTICS:
        ( A ) LENGTH: 252 amino acids
        ( B ) TYPE: amino acid
        ( D ) TOPOLOGY: linear ( x i ) SEQUENCE DESCRIPTION: SEQ ID NO:8:

```
Arg Gln Arg Gly Leu Phe Pro Ala Ile Leu Asn Leu Ala Ser Asn Ala
 1               5                   10                  15

His Ile Ser Thr Asn Ala Thr Cys Gly Glu Lys Gly Pro Glu Met Phe
            20                  25                  30

Cys Lys Leu Val Glu His Val Pro Gly Arg Pro Val Arg Asn Pro Gln
        35                  40                  45

Cys Arg Ile Cys Asp Gly Asn Ser Ala Asn Pro Arg Glu Arg His Pro
    50              55                  60

Ile Ser His Ala Ile Asp Gly Thr Asn Asn Trp Trp Gln Ser Pro Ser
65                  70                  75                  80

Ile Gln Asn Gly Arg Glu Tyr His Trp Val Thr Ile Thr Leu Asp Leu
                85                  90                  95

Arg Gln Val Phe Gln Val Ala Tyr Val Ile Ile Lys Ala Ala Asn Ala
                100             105                 110

Pro Arg Pro Gly Asn Trp Ile Leu Glu Arg Ser Leu Asp Gly Thr Thr
            115                 120                 125

Phe Ser Pro Trp Gln Tyr Tyr Ala Val Ser Asp Ser Glu Cys Leu Ser
        130                 135                 140

Arg Tyr Asn Ile Thr Pro Arg Arg Gly Pro Pro Thr Tyr Arg Ala Asp
145                 150                 155                 160

Asp Glu Val Ile Cys Thr Ser Tyr Tyr Ser Arg Leu Val Pro Leu Glu
                165                 170                 175

His Gly Glu Ile His Thr Ser Leu Ile Asn Gly Arg Pro Ser Ala Asp
            180                 185                 190

Asp Leu Ser Pro Lys Leu Leu Glu Phe Thr Ser Ala Arg Tyr Ile Arg
        195                 200                 205

Leu Arg Phe Glu Arg Ile Arg Thr Leu Asn Ala Asp Leu Met Thr Leu
    210                 215                 220

Ser His Arg Glu Pro Lys Glu Leu Asp Pro Met Leu Pro Arg Arg Tyr
225                 230                 235                 240

Tyr Tyr Ser Ile Lys Asp Ile Ser Val Gly Gly Met
                245                 250
```

( 2 ) INFORMATION FOR SEQ ID NO:9:

( i ) SEQUENCE CHARACTERISTICS:
        ( A ) LENGTH: 252 amino acids
        ( B ) TYPE: amino acid
        ( D ) TOPOLOGY: linear ( x i ) SEQUENCE DESCRIPTION: SEQ ID NO:9:

```
Gln Gln Arg Gly Leu Phe Pro Ala Ile Leu Asn Leu Ala Thr Asn Ala
 1               5                   10                  15

His Ile Ser Ala Asn Ala Thr Cys Gly Glu Lys Gly Pro Glu Met Phe
            20                  25                  30

Cys Lys Leu Val Glu His Val Pro Gly Arg Pro Val Arg His Ala Gln
        35                  40                  45

Cys Arg Val Cys Asp Gly Asn Ser Thr Asn Pro Arg Glu Arg His Pro
    50              55                  60
```

| Ile | Ser | His | Ala | Ile | Asp | Gly | Thr | Asn | Asn | Trp | Trp | Gln | Ser | Pro | Ser |
|65|||||70|||||75|||||80|
| Ile | Gln | Asn | Gly | Arg | Glu | Tyr | His | Trp | Val | Thr | Val | Thr | Leu | Asp | Leu |
|||||85|||||90|||||95||
| Arg | Gln | Val | Phe | Gln | Val | Ala | Tyr | Ile | Ile | Ile | Lys | Ala | Ala | Asn | Ala |
||||100|||||105|||||110||
| Pro | Arg | Pro | Gly | Asn | Trp | Ile | Leu | Glu | Arg | Ser | Val | Asp | Gly | Val | Lys |
|||115|||||120|||||125|||
| Phe | Lys | Pro | Trp | Gln | Tyr | Tyr | Ala | Val | Ser | Asp | Thr | Glu | Cys | Leu | Thr |
||130|||||135|||||140||||
| Arg | Tyr | Lys | Ile | Thr | Pro | Arg | Arg | Gly | Pro | Pro | Thr | Tyr | Arg | Ala | Asp |
|145|||||150|||||155|||||160|
| Asn | Glu | Val | Ile | Cys | Thr | Ser | Tyr | Tyr | Ser | Lys | Leu | Val | Pro | Leu | Glu |
|||||165|||||170|||||175||
| His | Gly | Glu | Ile | His | Thr | Ser | Leu | Ile | Asn | Gly | Arg | Pro | Ser | Ala | Asp |
||||180|||||185|||||190||
| Asp | Pro | Ser | Pro | Gln | Leu | Leu | Glu | Phe | Thr | Ser | Ala | Arg | Tyr | Ile | Arg |
|||195|||||200|||||205|||
| Leu | Arg | Leu | Gln | Arg | Ile | Arg | Thr | Leu | Asn | Ala | Asp | Leu | Met | Thr | Leu |
||210|||||215|||||220||||
| Ser | His | Arg | Asp | Leu | Arg | Asp | Leu | Asp | Pro | Ile | Val | Thr | Arg | Arg | Tyr |
|225|||||230|||||235|||||240|
| Tyr | Tyr | Ser | Ile | Lys | Asp | Ile | Ser | Val | Gly | Gly | Met |
|||||245|||||250||||

( 2 ) INFORMATION FOR SEQ ID NO:10:

( i ) SEQUENCE CHARACTERISTICS:
        ( A ) LENGTH: 264 amino acids
        ( B ) TYPE: amino acid
        ( D ) TOPOLOGY: linear ( x i ) SEQUENCE DESCRIPTION: SEQ ID NO:10:

| Gln | Arg | Pro | Gln | Gln | Gln | Arg | Gln | Ser | Gln | Ala | His | Gln | Gln | Arg | Gly |
|1||||5|||||10|||||15||
| Leu | Phe | Pro | Ala | Val | Leu | Asn | Leu | Ala | Ser | Asn | Ala | Leu | Ile | Thr | Thr |
||||20|||||25|||||30||
| Asn | Ala | Thr | Cys | Gly | Glu | Lys | Gly | Pro | Glu | Met | Tyr | Cys | Lys | Leu | Val |
|||35|||||40|||||45|||
| Glu | His | Val | Pro | Gly | Gln | Pro | Val | Arg | Asn | Pro | Gln | Cys | Arg | Ile | Cys |
||50|||||55|||||60||||
| Asn | Gln | Asn | Ser | Ser | Asn | Pro | Asn | Gln | Arg | His | Pro | Ile | Thr | Asn | Ala |
|65|||||70|||||75|||||80|
| Ile | Asp | Gly | Lys | Asn | Thr | Trp | Trp | Gln | Ser | Pro | Ser | Ile | Lys | Asn | Gly |
|||||85|||||90|||||95||
| Ile | Glu | Tyr | His | Tyr | Val | Thr | Ile | Thr | Leu | Asp | Leu | Gln | Gln | Val | Phe |
||||100|||||105|||||110||
| Gln | Ile | Ala | Tyr | Val | Ile | Val | Lys | Ala | Ala | Asn | Ser | Pro | Arg | Pro | Gly |
|||115|||||120|||||125|||
| Asn | Trp | Ile | Leu | Glu | Arg | Ser | Leu | Asp | Asp | Val | Glu | Tyr | Lys | Pro | Trp |
||130|||||135|||||140||||
| Gln | Tyr | His | Ala | Val | Thr | Asp | Thr | Glu | Cys | Leu | Thr | Leu | Tyr | Asn | Ile |
|145|||||150|||||155|||||160|
| Tyr | Pro | Arg | Thr | Gly | Pro | Pro | Ser | Tyr | Ala | Lys | Asp | Asp | Glu | Val | Ile |
|||||165|||||170|||||175||
| Cys | Thr | Ser | Phe | Tyr | Ser | Lys | Ile | His | Pro | Leu | Glu | Asn | Gly | Glu | Ile |

|   |   |   |   |   | 180 |   |   |   |   | 185 |   |   |   |   | 190 |   |
|---|---|---|---|---|---|---|---|---|---|---|---|---|---|---|---|---|
| His | Ile | Ser | Leu | Ile | Asn | Gly | Arg | Pro | Ser | Ala | Asp | Asp | Pro | Ser | Pro |   |
|   |   | 195 |   |   |   |   | 200 |   |   |   |   | 205 |   |   |   |   |
| Glu | Leu | Leu | Glu | Phe | Thr | Ser | Ala | Arg | Tyr | Ile | Arg | Leu | Arg | Phe | Gln |   |
|   |   | 210 |   |   |   |   | 215 |   |   |   |   | 220 |   |   |   |   |
| Arg | Ile | Arg | Thr | Leu | Asn | Ala | Asp | Leu | Met | Met | Phe | Ala | His | Lys | Asp |   |
| 225 |   |   |   |   | 230 |   |   |   |   | 235 |   |   |   |   | 240 |   |
| Pro | Arg | Glu | Ile | Asp | Pro | Ile | Val | Thr | Arg | Tyr | Tyr | Tyr | Ser | Val |   |   |
|   |   |   |   | 245 |   |   |   |   | 250 |   |   |   |   | 255 |   |   |
| Lys | Asp | Ile | Ser | Val | Gly | Gly | Met |   |   |   |   |   |   |   |   |   |
|   |   |   | 260 |   |   |   |   |   |   |   |   |   |   |   |   |   |

( 2 ) INFORMATION FOR SEQ ID NO:11:

( i ) SEQUENCE CHARACTERISTICS:
        ( A ) LENGTH: 250 amino acids
        ( B ) TYPE: amino acid
        ( D ) TOPOLOGY: linear ( x i ) SEQUENCE DESCRIPTION: SEQ ID NO:11:

| Glu | Leu | Thr | Pro | Pro | Tyr | Phe | Asn | Leu | Ala | Thr | Gly | Arg | Lys | Ile | Tyr |
|---|---|---|---|---|---|---|---|---|---|---|---|---|---|---|---|
| 1 |   |   |   | 5 |   |   |   |   | 10 |   |   |   |   | 15 |   |
| Ala | Thr | Ala | Thr | Cys | Gly | Pro | Asp | Thr | Asp | Gly | Pro | Glu | Leu | Tyr | Cys |
|   |   |   | 20 |   |   |   |   | 25 |   |   |   |   | 30 |   |   |
| Lys | Leu | Val | Gly | Ala | Asn | Thr | Glu | His | Asp | His | Ile | Asp | Tyr | Ser | Val |
|   |   |   | 35 |   |   |   |   | 40 |   |   |   |   | 45 |   |   |
| Ile | Gln | Gly | Gln | Val | Cys | Asp | Tyr | Cys | Asp | Pro | Thr | Val | Pro | Glu | Arg |
|   | 50 |   |   |   |   | 55 |   |   |   |   | 60 |   |   |   |   |
| Asn | His | Pro | Pro | Glu | Asn | Ala | Ile | Asp | Gly | Thr | Glu | Ala | Trp | Trp | Gln |
| 65 |   |   |   |   | 70 |   |   |   |   | 75 |   |   |   |   | 80 |
| Ser | Pro | Pro | Leu | Ser | Arg | Gly | Met | Lys | Phe | Asn | Glu | Val | Asn | Leu | Thr |
|   |   |   |   | 85 |   |   |   |   | 90 |   |   |   |   | 95 |   |
| Ile | Asn | Phe | Glu | Gln | Glu | Phe | His | Val | Ala | Tyr | Leu | Phe | Ile | Arg | Met |
|   |   |   |   | 100 |   |   |   |   | 105 |   |   |   |   | 110 |   |
| Gly | Asn | Ser | Pro | Arg | Pro | Gly | Leu | Trp | Thr | Leu | Glu | Lys | Ser | Thr | Asp |
|   |   |   | 115 |   |   |   |   | 120 |   |   |   |   | 125 |   |   |
| Tyr | Gly | Lys | Thr | Trp | Thr | Pro | Trp | Gln | His | Phe | Ser | Asp | Thr | Pro | Ala |
|   |   | 130 |   |   |   |   | 135 |   |   |   |   | 140 |   |   |   |
| Asp | Cys | Glu | Thr | Tyr | Phe | Gly | Lys | Asp | Thr | Tyr | Lys | Pro | Ile | Thr | Arg |
| 145 |   |   |   |   | 150 |   |   |   |   | 155 |   |   |   |   | 160 |
| Asp | Asp | Asp | Val | Ile | Cys | Thr | Thr | Glu | Tyr | Ser | Lys | Ile | Val | Pro | Leu |
|   |   |   |   | 165 |   |   |   |   | 170 |   |   |   |   | 175 |   |
| Glu | Asn | Gly | Glu | Ile | Pro | Val | Met | Leu | Leu | Asn | Glu | Arg | Pro | Ser | Ser |
|   |   |   | 180 |   |   |   |   | 185 |   |   |   |   | 190 |   |   |
| Thr | Asn | Tyr | Phe | Asn | Ser | Thr | Val | Leu | Gln | Glu | Trp | Thr | Arg | Ala | Thr |
|   |   | 195 |   |   |   |   | 200 |   |   |   |   | 205 |   |   |   |
| Asn | Val | Arg | Ile | Arg | Leu | Leu | Arg | Thr | Lys | Asn | Leu | Leu | Gly | His | Leu |
|   |   | 210 |   |   |   |   | 215 |   |   |   |   | 220 |   |   |   |
| Met | Ser | Val | Ala | Arg | Gln | Asp | Pro | Thr | Val | Thr | Arg | Arg | Tyr | Phe | Tyr |
| 225 |   |   |   |   | 230 |   |   |   |   | 235 |   |   |   |   | 240 |
| Ser | Ile | Lys | Asp | Ile | Ser | Ile | Gly | Gly | Arg |   |   |   |   |   |   |
|   |   |   |   | 245 |   |   |   |   | 250 |   |   |   |   |   |   |

( 2 ) INFORMATION FOR SEQ ID NO:12:

( i ) SEQUENCE CHARACTERISTICS:
        ( A ) LENGTH: 252 amino acids (B) TYPE: amino acid
(D) TOPOLOGY: linear (xi) SEQUENCE DESCRIPTION: SEQ ID NO:12:

| Gln | Ala | Ala | Met | Asp | Glu | Cys | Thr | Asp | Glu | Gly | Gly | Arg | Pro | Gln | Arg |
|---|---|---|---|---|---|---|---|---|---|---|---|---|---|---|---|
| 1 | | | | 5 | | | | | 10 | | | | | 15 | |
| Cys | Met | Pro | Glu | Phe | Val | Asn | Ala | Ala | Phe | Asn | Val | Thr | Val | Val | Ala |
| | | | 20 | | | | | 25 | | | | | 30 | | |
| Thr | Asn | Thr | Cys | Gly | Thr | Pro | Pro | Glu | Glu | Tyr | Cys | Val | Gln | Thr | Gly |
| | | 35 | | | | | 40 | | | | | 45 | | | |
| Val | Thr | Gly | Val | Thr | Lys | Ser | Cys | His | Leu | Cys | Asp | Ala | Gly | Gln | Pro |
| | 50 | | | | | 55 | | | | | 60 | | | | |
| His | Leu | Gln | His | Gly | Ala | Ala | Phe | Leu | Thr | Asp | Tyr | Asn | Asn | Gln | Ala |
| 65 | | | | | 70 | | | | | 75 | | | | | 80 |
| Asp | Thr | Thr | Trp | Trp | Gln | Ser | Gln | Thr | Met | Leu | Ala | Gly | Val | Gln | Tyr |
| | | | | 85 | | | | | 90 | | | | | 95 | |
| Pro | Ser | Ser | Ile | Asn | Leu | Thr | Leu | His | Leu | Gly | Lys | Ala | Phe | Asp | Ile |
| | | | | 100 | | | | | 105 | | | | | 110 | |
| Thr | Tyr | Val | Arg | Leu | Lys | Phe | His | Thr | Ser | Arg | Pro | Glu | Ser | Phe | Ala |
| | | | 115 | | | | | 120 | | | | | 125 | | |
| Ile | Tyr | Lys | Arg | Thr | Arg | Glu | Asp | Gly | Pro | Trp | Ile | Pro | Tyr | Gln | Tyr |
| | | 130 | | | | | 135 | | | | | 140 | | | |
| Tyr | Ser | Gly | Ser | Cys | Glu | Asn | Thr | Tyr | Ser | Lys | Ala | Asn | Arg | Gly | Phe |
| 145 | | | | | 150 | | | | | 155 | | | | | 160 |
| Ile | Arg | Thr | Gly | Gly | Asp | Glu | Gln | Gln | Ala | Leu | Cys | Thr | Asp | Glu | Phe |
| | | | | 165 | | | | | 170 | | | | | 175 | |
| Ser | Asp | Ile | Ser | Pro | Leu | Thr | Gly | Gly | Asn | Val | Ala | Phe | Ser | Thr | Leu |
| | | | 180 | | | | | 185 | | | | | 190 | | |
| Glu | Gly | Arg | Pro | Ser | Ala | Tyr | Asn | Phe | Asp | Asn | Ser | Pro | Val | Leu | Gln |
| | | 195 | | | | | 200 | | | | | 205 | | | |
| Glu | Trp | Val | Thr | Ala | Thr | Asp | Ile | Arg | Val | Thr | Leu | Asn | Arg | Leu | Asn |
| | 210 | | | | | 215 | | | | | 220 | | | | |
| Thr | Phe | Gly | Asp | Glu | Val | Phe | Asn | Asp | Pro | Lys | Val | Leu | Lys | Ser | Tyr |
| 225 | | | | | 230 | | | | | 235 | | | | | 240 |
| Tyr | Tyr | Ala | Ile | Ser | Asp | Phe | Ala | Val | Gly | Gly | Arg | | | | |
| | | | | 245 | | | | | 250 | | | | | | |

(2) INFORMATION FOR SEQ ID NO:13:

(i) SEQUENCE CHARACTERISTICS:
(A) LENGTH: 278 amino acids
(B) TYPE: amino acid
(D) TOPOLOGY: linear (xi) SEQUENCE DESCRIPTION: SEQ ID NO:13:

| Cys | Phe | Cys | Tyr | Gly | His | Ala | Ser | Glu | Cys | Ala | Pro | Val | Asp | Gly | Phe |
|---|---|---|---|---|---|---|---|---|---|---|---|---|---|---|---|
| 1 | | | | 5 | | | | | 10 | | | | | 15 | |
| Asn | Glu | Glu | Val | Glu | Gly | Met | Val | His | Gly | His | Cys | Met | Cys | Arg | His |
| | | | 20 | | | | | 25 | | | | | 30 | | |
| Asn | Thr | Lys | Gly | Leu | Asn | Cys | Glu | Leu | Cys | Met | Asp | Phe | Tyr | His | Asp |
| | | 35 | | | | | 40 | | | | | 45 | | | |
| Leu | Pro | Trp | Arg | Pro | Ala | Glu | Gly | Arg | Asn | Ser | Asn | Ala | Cys | Lys | Lys |
| | 50 | | | | | 55 | | | | | 60 | | | | |
| Cys | Asn | Cys | Asn | Glu | His | Ser | Ile | Ser | Cys | His | Phe | Asp | Met | Ala | Val |
| 65 | | | | | 70 | | | | | 75 | | | | | 80 |
| Tyr | Leu | Ala | Thr | Gly | Asn | Val | Ser | Gly | Gly | Val | Cys | Asp | Asp | Cys | Gln |
| | | | | 85 | | | | | 90 | | | | | 95 | |

```
His  Asn  Thr  Met  Gly  Arg  Asn  Cys  Glu  Gln  Cys  Lys  Pro  Phe  Tyr  Tyr
               100                      105                      110

Gln  His  Pro  Glu  Arg  Asp  Ile  Arg  Asp  Pro  Asn  Phe  Cys  Glu  Arg  Cys
          115                      120                      125

Thr  Cys  Asp  Pro  Ala  Gly  Ser  Gln  Asn  Glu  Gly  Ile  Cys  Asp  Ser  Tyr
     130                      135                      140

Thr  Asp  Phe  Ser  Thr  Gly  Leu  Ile  Ala  Gly  Gln  Cys  Arg  Cys  Lys  Leu
145                      150                      155                      160

Asn  Val  Glu  Gly  Glu  His  Cys  Asp  Val  Cys  Lys  Glu  Gly  Phe  Tyr  Asp
                    165                      170                      175

Leu  Ser  Ser  Glu  Asp  Pro  Phe  Gly  Cys  Lys  Ser  Cys  Ala  Cys  Asn  Pro
               180                      185                      190

Leu  Gly  Thr  Ile  Pro  Gly  Gly  Asn  Pro  Cys  Asp  Ser  Glu  Thr  Gly  His
          195                      200                      205

Cys  Tyr  Cys  Lys  Arg  Leu  Val  Thr  Gly  Gln  His  Cys  Asp  Gln  Cys  Leu
     210                      215                      220

Pro  Glu  His  Trp  Gly  Leu  Ser  Asn  Asp  Leu  Asp  Gly  Cys  Arg  Pro  Cys
225                      230                      235                      240

Asp  Cys  Asp  Leu  Gly  Gly  Ala  Leu  Asn  Asn  Ser  Cys  Phe  Ala  Glu  Ser
               245                      250                      255

Gly  Gln  Cys  Ser  Cys  Arg  Pro  His  Met  Ile  Gly  Arg  Gln  Cys  Asn  Glu
               260                      265                      270

Val  Glu  Pro  Gly  Tyr  Tyr
               275
```

(2) INFORMATION FOR SEQ ID NO:14:

(i) SEQUENCE CHARACTERISTICS:
        (A) LENGTH: 269 amino acids
        (B) TYPE: amino acid
        (D) TOPOLOGY: linear (xi) SEQUENCE DESCRIPTION: SEQ ID NO:14:

```
Cys  Phe  Cys  Tyr  Gly  His  Ala  Ser  Gln  Cys  Ala  Pro  Ala  Pro  Gly  Ala
1              5                        10                       15

Pro  Ala  His  Ala  Glu  Gly  Met  Val  His  Gly  Ala  Cys  Ile  Cys  Lys  His
               20                       25                       30

Asn  Thr  Arg  Gly  Leu  Asn  Cys  Glu  Gln  Cys  Gln  Asp  Phe  Tyr  Gln  Asp
          35                       40                       45

Leu  Pro  Trp  His  Pro  Ala  Glu  Asp  Gly  His  Thr  His  Ala  Cys  Arg  Lys
     50                       55                       60

Cys  Glu  Cys  Asn  Gly  His  Ser  His  Ser  Cys  His  Phe  Asp  Met  Ala  Val
65                       70                       75                       80

Tyr  Leu  Ala  Ser  Gly  Asn  Val  Ser  Gly  Gly  Val  Cys  Asp  Gly  Cys  Gln
                    85                       90                       95

His  Asn  Thr  Ala  Gly  Arg  His  Cys  Glu  Leu  Cys  Arg  Pro  Phe  Phe  Tyr
               100                      105                      110

Arg  Asp  Pro  Thr  Lys  Asp  Met  Arg  Asp  Pro  Ala  Ala  Cys  Arg  Pro  Cys
               115                      120                      125

Asp  Cys  Asp  Pro  Met  Gly  Ser  Gln  Asp  Gly  Gly  Arg  Cys  Asp  Ser  His
     130                      135                      140

Asp  Asp  Pro  Val  Leu  Gly  Leu  Val  Ser  Gly  Gln  Cys  Arg  Cys  Lys  Glu
145                      150                      155                      160

His  Val  Val  Gly  Thr  Arg  Cys  Gln  Gln  Cys  Arg  Asp  Gly  Phe  Phe  Gly
                    165                      170                      175
```

```
Leu  Ser  Ala  Ser  Asn  Pro  Arg  Gly  Cys  Gln  Arg  Cys  Gln  Cys  Asn  Ser
               180                      185                     190

Arg  Gly  Thr  Val  Pro  Gly  Gly  Thr  Pro  Cys  Asp  Ser  Ser  Ser  Gly  Thr
          195                      200                     205

Cys  Phe  Cys  Lys  Arg  Leu  Val  Thr  Gly  Asp  Gly  Cys  Asp  Arg  Cys  Leu
     210                      215                     220

Pro  Gly  His  Trp  Gly  Leu  Ser  His  Asp  Leu  Leu  Gly  Cys  Arg  Pro  Cys
225                      230                     235                     240

Asp  Cys  Asp  Val  Gly  Gly  Ala  Leu  Asp  Pro  Gln  Cys  Asp  Glu  Ala  Thr
               245                      250                     255

Gly  Gln  Cys  Pro  Cys  Arg  Pro  His  Met  Ile  Gly  Arg  Arg
               260                      265
```

( 2 ) INFORMATION FOR SEQ ID NO:15:

( i ) SEQUENCE CHARACTERISTICS:
        ( A ) LENGTH: 243 amino acids
        ( B ) TYPE: amino acid
        ( D ) TOPOLOGY: linear ( x i ) SEQUENCE DESCRIPTION: SEQ ID NO:15:

```
Cys  Ile  Cys  Tyr  Gly  His  Ala  Ser  Ser  Cys  Pro  Trp  Asp  Glu  Thr  Thr
1              5                        10                      15

Lys  Lys  Leu  Gln  Cys  Gln  Cys  Glu  His  Asn  Thr  Cys  Gly  Glu  Ser  Cys
               20                       25                      30

Asn  Arg  Cys  Cys  Pro  Gly  Tyr  His  Gln  Gln  Pro  Trp  Arg  Pro  Gly  Thr
          35                       40                      45

Val  Ser  Ser  Gly  Asn  Thr  Cys  Glu  Ala  Cys  Asn  Cys  His  Asn  Lys  Ala
     50                       55                      60

Lys  Asp  Cys  Tyr  Tyr  Asp  Glu  Ser  Val  Ala  Lys  Gln  Lys  Lys  Ser  Leu
65                       70                      75                       80

Asn  Thr  Ala  Gly  Gln  Phe  Arg  Gly  Gly  Gly  Val  Cys  Ile  Asn  Cys  Leu
               85                                  90                      95

Gln  Asn  Thr  Met  Gly  Ile  Asn  Cys  Glu  Thr  Cys  Ile  Asp  Gly  Tyr  Tyr
               100                      105                     110

Arg  Pro  His  Lys  Val  Ser  Pro  Tyr  Glu  Asp  Glu  Pro  Cys  Arg  Pro  Cys
          115                      120                     125

Asn  Cys  Asp  Pro  Val  Gly  Ser  Leu  Ser  Ser  Val  Cys  Ile  Lys  Asp  Asp
     130                      135                     140

Leu  His  Ser  Asp  Leu  Glu  Asn  Gly  Lys  Gln  Pro  Gly  Gln  Cys  Pro  Cys
145                      150                     155                     160

Lys  Glu  Gly  Tyr  Thr  Gly  Glu  Lys  Cys  Asp  Arg  Cys  Gln  Leu  Gly  Tyr
               165                      170                     175

Lys  Asp  Tyr  Pro  Thr  Cys  Val  Ser  Cys  Gly  Cys  Asn  Pro  Val  Gly  Ser
               180                      185                     190

Ala  Ser  Asp  Glu  Pro  Cys  Thr  Gly  Pro  Cys  Val  Cys  Lys  Glu  Asn  Val
          195                      200                     205

Glu  Gly  Lys  Ala  Cys  Asp  Arg  Cys  Lys  Pro  Gly  Phe  Tyr  Asn  Leu  Lys
     210                      215                     220

Glu  Lys  Asn  Pro  Arg  Gly  Cys  Ser  Glu  Cys  Phe  Cys  Phe  Gly  Val  Ser
225                      230                     235                     240

Asp  Val  Cys
```

( 2 ) INFORMATION FOR SEQ ID NO:16:

( i ) SEQUENCE CHARACTERISTICS:
        ( A ) LENGTH: 243 amino acids (B) TYPE: amino acid
(D) TOPOLOGY: linear (xi) SEQUENCE DESCRIPTION: SEQ ID NO:16:

| Cys | Ile | Cys | Tyr | Gly | His | Ala | Ser | Ser | Cys | Pro | Trp | Asp | Glu | Glu | Ala |
|-----|-----|-----|-----|-----|-----|-----|-----|-----|-----|-----|-----|-----|-----|-----|-----|
| 1 | | | | 5 | | | | | 10 | | | | | 15 | |
| Lys | Gln | Leu | Gln | Cys | Gln | Cys | Glu | His | Asn | Thr | Cys | Gly | Glu | Ser | Cys |
| | | | 20 | | | | | 25 | | | | | 30 | | |
| Asp | Arg | Cys | Cys | Pro | Gly | Tyr | His | Gln | Gln | Pro | Trp | Arg | Pro | Gly | Thr |
| | | 35 | | | | | 40 | | | | | 45 | | | |
| Ile | Ser | Ser | Gly | Asn | Glu | Cys | Glu | Glu | Cys | Asn | Cys | His | Asn | Lys | Ala |
| | 50 | | | | | 55 | | | | | 60 | | | | |
| Lys | Asp | Cys | Tyr | Tyr | Asp | Ser | Ser | Val | Ala | Lys | Glu | Arg | Arg | Ser | Leu |
| 65 | | | | 70 | | | | | 75 | | | | | 80 | |
| Asn | Thr | Ala | Gly | Gln | Tyr | Ser | Gly | Gly | Val | Cys | Val | Asn | Cys | Ser |
| | | | | 85 | | | | | 90 | | | | 95 | |
| Gln | Asn | Thr | Thr | Gly | Ile | Asn | Cys | Glu | Thr | Cys | Ile | Asp | Gln | Tyr | Tyr |
| | | | 100 | | | | | 105 | | | | | 110 | | |
| Arg | Pro | His | Lys | Val | Ser | Pro | Tyr | Asp | Asp | His | Pro | Cys | Arg | Pro | Cys |
| | | | 115 | | | | | 120 | | | | | 125 | | |
| Asn | Cys | Asp | Pro | Val | Gly | Ser | Leu | Ser | Ser | Val | Cys | Ile | Lys | Asp | Asp |
| | 130 | | | | | 135 | | | | | 140 | | | | |
| Arg | His | Ala | Asp | Leu | Ala | Asn | Gly | Lys | Trp | Pro | Gly | Gln | Cys | Pro | Cys |
| 145 | | | | | 150 | | | | | 155 | | | | | 160 |
| Arg | Lys | Gly | Tyr | Ala | Gly | Asp | Lys | Cys | Asp | Arg | Cys | Gln | Phe | Gly | Tyr |
| | | | | 165 | | | | | 170 | | | | | 175 | |
| Arg | Gly | Phe | Pro | Asn | Cys | Ile | Pro | Cys | Asp | Cys | Arg | Thr | Val | Gly | Ser |
| | | | 180 | | | | | 185 | | | | | 190 | | |
| Leu | Asn | Glu | Asp | Pro | Cys | Ile | Glu | Pro | Cys | Leu | Cys | Lys | Lys | Asn | Val |
| | | | 195 | | | | | 200 | | | | | 205 | | |
| Glu | Gly | Lys | Asn | Cys | Asp | Arg | Cys | Lys | Pro | Gly | Phe | Tyr | Asn | Leu | Lys |
| | 210 | | | | | 215 | | | | | 220 | | | | |
| Glu | Arg | Asn | Pro | Glu | Gly | Cys | Ser | Glu | Cys | Phe | Cys | Phe | Gly | Val | Ser |
| 225 | | | | | 230 | | | | | 235 | | | | | 240 |
| Gly | Val | Cys | | | | | | | | | | | | | |

(2) INFORMATION FOR SEQ ID NO:17:

(i) SEQUENCE CHARACTERISTICS:
(A) LENGTH: 241 amino acids
(B) TYPE: amino acid
(D) TOPOLOGY: linear (xi) SEQUENCE DESCRIPTION: SEQ ID NO:17:

| Cys | Ile | Cys | Tyr | Gly | His | Ala | Arg | Ala | Cys | Pro | Leu | Asp | Pro | Ala | Thr |
|-----|-----|-----|-----|-----|-----|-----|-----|-----|-----|-----|-----|-----|-----|-----|-----|
| 1 | | | | 5 | | | | | 10 | | | | | 15 | |
| Asn | Lys | Ser | Arg | Cys | Glu | Cys | Glu | His | Asn | Thr | Cys | Gly | Asp | Ser | Cys |
| | | | 20 | | | | | 25 | | | | | 30 | | |
| Asp | Gln | Cys | Cys | Pro | Gly | Phe | His | Gln | Lys | Pro | Trp | Arg | Ala | Gly | Thr |
| | | 35 | | | | | 40 | | | | | 45 | | | |
| Phe | Leu | Thr | Lys | Thr | Glu | Cys | Glu | Ala | Cys | Asn | Cys | His | Gly | Lys | Ala |
| | 50 | | | | | 55 | | | | | 60 | | | | |
| Glu | Glu | Cys | Tyr | Tyr | Asp | Glu | Asn | Val | Ala | Arg | Arg | Asn | Leu | Ser | Leu |
| 65 | | | | 70 | | | | | 75 | | | | | 80 | |
| Asn | Ile | Arg | Gly | Lys | Tyr | Ile | Gly | Gly | Val | Cys | Ile | Asn | Cys | Thr |
| | | | | 85 | | | | | 90 | | | | 95 | |

```
Gln  Asn  Thr  Ala  Gly  Ile  Asn  Cys  Glu  Thr  Cys  Thr  Asp  Gly  Phe  Phe
               100                 105                      110

Arg  Pro  Lys  Gly  Val  Ser  Pro  Asn  Tyr  Pro  Arg  Pro  Cys  Gln  Pro  Cys
               115                 120                      125

His  Cys  Asp  Pro  Ile  Gly  Ser  Leu  Asn  Glu  Val  Cys  Val  Lys  Asp  Glu
          130                      135                      140

Lys  His  Ala  Arg  Arg  Gly  Leu  Ala  Pro  Gly  Ser  Cys  His  Cys  Lys  Thr
145                           150                 155                           160

Gly  Phe  Gly  Gly  Val  Ser  Cys  Asp  Arg  Cys  Ala  Arg  Gly  Tyr  Thr  Gly
                    165                      170                      175

Tyr  Pro  Asp  Cys  Lys  Ala  Cys  Asn  Cys  Ser  Gly  Leu  Gly  Ser  Lys  Asn
               180                 185                                190

Glu  Asp  Pro  Cys  Phe  Gly  Pro  Cys  Ile  Cys  Lys  Glu  Asn  Val  Glu  Gly
               195                 200                 205

Gly  Asp  Cys  Ser  Arg  Cys  Lys  Ser  Gly  Phe  Phe  Asn  Leu  Gln  Glu  Asp
          210                 215                      220

Asn  Trp  Lys  Gly  Cys  Asp  Glu  Cys  Phe  Cys  Ser  Gly  Val  Ser  Asn  Arg
225                      230                 235                           240

Cys
```

( 2 ) INFORMATION FOR SEQ ID NO:18:

( i ) SEQUENCE CHARACTERISTICS:
        ( A ) LENGTH: 219 amino acids
        ( B ) TYPE: amino acid
        ( D ) TOPOLOGY: linear ( x i ) SEQUENCE DESCRIPTION: SEQ ID NO:18:

```
Cys  Lys  Cys  Asn  Gly  His  Ala  Ser  Glu  Cys  Met  Lys  Asn  Glu  Phe  Asp
1                   5                    10                       15

Lys  Leu  Val  Cys  Asn  Cys  Lys  His  Asn  Thr  Tyr  Gly  Val  Asp  Cys  Glu
               20                 25                      30

Lys  Cys  Leu  Pro  Phe  Phe  Asn  Asp  Arg  Pro  Trp  Arg  Arg  Ala  Thr  Ala
          35                 40                      45

Glu  Ser  Ala  Ser  Glu  Cys  Leu  Pro  Cys  Asp  Cys  Asn  Gly  Arg  Ser  Gln
     50                  55                      60

Glu  Cys  Tyr  Phe  Asp  Pro  Glu  Leu  Tyr  Arg  Ser  Thr  Gly  His  Gly  Gly
65                       70                      75                           80

His  Cys  Thr  Asn  Cys  Gln  Asp  Asn  Thr  Asp  Gly  Ala  His  Cys  Glu  Arg
               85                      90                           95

Cys  Arg  Glu  Asn  Phe  Phe  Arg  Leu  Gly  Asn  Asn  Glu  Ala  Cys  Ser  Ser
               100                 105                      110

Cys  His  Cys  Ser  Pro  Val  Gly  Ser  Leu  Ser  Thr  Gln  Cys  Asp  Ser  Tyr
          115                      120                      125

Gly  Arg  Cys  Ser  Cys  Lys  Pro  Gly  Val  Met  Gly  Asp  Lys  Cys  Asp  Arg
     130                      135                      140

Cys  Gln  Pro  Gly  Phe  His  Ser  Leu  Thr  Glu  Ala  Gly  Cys  Arg  Pro  Cys
145                      150                      155                           160

Ser  Cys  Asp  Pro  Ser  Gly  Ser  Ile  Asp  Glu  Cys  Asn  Val  Glu  Thr  Gly
               165                      170                      175

Arg  Cys  Val  Cys  Lys  Asp  Asn  Val  Glu  Gly  Phe  Asn  Cys  Glu  Arg  Cys
               180                 185                      190

Lys  Pro  Gly  Phe  Phe  Asn  Leu  Glu  Ser  Ser  Asn  Pro  Arg  Gly  Cys  Thr
          195                      200                      205

Pro  Cys  Phe  Cys  Phe  Gly  His  Ser  Ser  Val  Cys
     210                 215
```

( 2 ) INFORMATION FOR SEQ ID NO:19:

( i ) SEQUENCE CHARACTERISTICS:
        ( A ) LENGTH: 314 amino acids
        ( B ) TYPE: amino acid
        ( D ) TOPOLOGY: linear ( x i ) SEQUENCE DESCRIPTION: SEQ ID NO:19:

```
Cys Met Cys Asn Gly His Ala Asp Thr Cys Asp Val Lys Asp Pro Lys
  1           5                  10                  15
Ser Pro Val Arg Ile Leu Ala Cys Arg Cys Gln His His Thr Cys Gly
             20                  25                  30
Ile Gln Cys Asn Glu Cys Cys Pro Gly Phe Glu Gln Lys Lys Trp Arg
         35                  40                  45
Gln Asn Thr Asn Ala Arg Pro Phe Asn Cys Glu Pro Cys Asn Cys His
     50                  55                  60
Gly His Ser Asn Glu Cys Lys Tyr Asp Glu Val Asn Arg Lys Gly
 65                  70                  75                  80
Leu Ser Leu Asp Ile His Gly His Tyr Asp Gly Gly Gly Val Cys Gln
                 85                  90                  95
Asn Cys Gln His Asn Thr Val Gly Ile Asn Cys Asn Lys Cys Lys Pro
            100                 105                 110
Lys Tyr Tyr Arg Pro Lys Gly Lys His Trp Asn Glu Thr Asp Val Cys
        115                 120                 125
Ser Pro Cys Gln Cys Asp Tyr Phe Phe Ser Thr Gly His Cys Glu Glu
    130                 135                 140
Glu Thr Gly Asn Cys Glu Cys Arg Ala Ala Phe Gln Pro Pro Ser Cys
145                 150                 155                 160
Asp Ser Cys Ala Tyr Gly Tyr Tyr Gly Tyr Pro Asn Cys Arg Glu Cys
                165                 170                 175
Glu Cys Asn Leu Asn Gly Thr Asn Gly Tyr His Cys Glu Ala Glu Ser
            180                 185                 190
Gly Gln Gln Cys Pro Cys Lys Ile Asn Phe Ala Phe Ala Tyr Cys Lys
        195                 200                 205
Gln Cys Ala Glu Gly Tyr Tyr Gly Phe Pro Glu Cys Lys Ala Cys Glu
    210                 215                 220
Cys Asn Lys Ile Gly Ser Ile Thr Asn Asp Cys Asn Val Thr Thr Gly
225                 230                 235                 240
Glu Cys Lys Cys Leu Thr Asn Phe Gly Gly Asp Asn Cys Glu Arg Cys
                245                 250                 255
Lys His Gly Tyr Phe Asn Tyr Pro Thr Cys Ser Tyr Cys Asp Cys Asp
            260                 265                 270
Asn Gln Gly Thr Glu Ser Glu Ile Cys Asn Lys Gln Ser Gly Gln Cys
        275                 280                 285
Ile Cys Arg Glu Gly Phe Gly Gly Pro Arg Cys Asp Gln Cys Leu Pro
    290                 295                 300
Gly Phe Tyr Asn Tyr Pro Asp Cys Lys Pro
305                 310
```

( 2 ) INFORMATION FOR SEQ ID NO:20:

( i ) SEQUENCE CHARACTERISTICS:
        ( A ) LENGTH: 169 amino acids
        ( B ) TYPE: amino acid
        ( D ) TOPOLOGY: linear ( x i ) SEQUENCE DESCRIPTION: SEQ ID NO:20:

```
Cys  Asp  Cys  Asn  Gly  Lys  Ser  Arg  Gln  Cys  Ile  Phe  Asp  Arg  Glu  Leu
  1             5                       10                       15

His  Arg  Gln  Thr  Gly  Asn  Gly  Phe  Arg  Cys  Leu  Asn  Cys  Asn  Asp  Asn
            20                       25                       30

Thr  Asp  Gly  Ile  His  Cys  Glu  Lys  Cys  Lys  Asn  Gly  Phe  Tyr  Arg  His
          35                       40                       45

Arg  Glu  Arg  Asp  Arg  Cys  Leu  Pro  Cys  Asn  Cys  Asn  Ser  Lys  Gly  Ser
      50                       55                       60

Leu  Ser  Ala  Arg  Cys  Asp  Asn  Ser  Gly  Arg  Cys  Ser  Cys  Lys  Pro  Gly
 65                       70                       75                       80

Val  Thr  Gly  Ala  Arg  Cys  Asp  Arg  Cys  Leu  Pro  Gly  Phe  His  Met  Leu
                85                       90                       95

Thr  Asp  Ala  Gly  Cys  Thr  Gln  Asp  Gln  Arg  Leu  Leu  Asp  Ser  Lys  Cys
              100                      105                      110

Asp  Cys  Asp  Pro  Ala  Gly  Ile  Ala  Gly  Pro  Cys  Asp  Ala  Gly  Arg  Cys
          115                      120                      125

Val  Cys  Lys  Pro  Ala  Val  Thr  Gly  Glu  Arg  Cys  Asp  Arg  Cys  Arg  Ser
      130                      135                      140

Gly  Tyr  Tyr  Asn  Leu  Asp  Gly  Gly  Asn  Pro  Glu  Gly  Cys  Thr  Gln  Cys
 145                      150                      155                      160

Phe  Cys  Tyr  Gly  His  Ser  Ala  Ser  Cys
                165
```

( 2 ) INFORMATION FOR SEQ ID NO:21:

( i ) SEQUENCE CHARACTERISTICS:
        ( A ) LENGTH: 7 amino acids
        ( B ) TYPE: amino acid
        ( D ) TOPOLOGY: linear ( x i ) SEQUENCE DESCRIPTION: SEQ ID NO:21:

```
Leu  Phe  Val  Gly  Gly  Leu  Pro
 1                 5
```

( 2 ) INFORMATION FOR SEQ ID NO:22:

( i ) SEQUENCE CHARACTERISTICS:
        ( A ) LENGTH: 14 amino acids
        ( B ) TYPE: amino acid
        ( D ) TOPOLOGY: linear ( x i ) SEQUENCE DESCRIPTION: SEQ ID NO:22:

```
Cys  Asn  Asn  Phe  Gly  Leu  Asp  Leu  Lys  Ala  Asp  Asp  Lys  Ile
 1                  5                        10
```

( 2 ) INFORMATION FOR SEQ ID NO:23:

( i ) SEQUENCE CHARACTERISTICS:
        ( A ) LENGTH: 14 amino acids
        ( B ) TYPE: amino acid
        ( D ) TOPOLOGY: linear ( x i ) SEQUENCE DESCRIPTION: SEQ ID NO:23:

```
Cys  Ser  Ile  Val  Asp  Ile  Asp  Thr  Asn  Gln  Glu  Glu  Asn  Ile
 1                  5                        10
```

NUCLEIC ACIDS ENCODING MEROSIN

This application is a continuation-in-part application of U.S. Ser. No. 919,951, filed Jul. 27, 1992, now abandoned, which in turn is a continuation application of U.S. Ser. No. 472,319, filed Jan. 30, 1990, now abandoned, the contents of which are hereby incorporated by reference into the present disclosure.

The present invention was supported by grants DK 30051, CA 45546, CA 28896 and Cancer Center Support Grant CA30199 from the National Institute of Health. The United States Government may have certain rights in this invention.

BACKGROUND OF THE INVENTION

This invention relates generally to basement membranes and specifically to a novel tissue-specific basement membrane-associated protein.

Basement membranes are thin sheets of extracellular matrix separating epithelial cells from underlying tissue stroma. They compartmentalize epithelial and endothelial organs and maintain tissue structures. In some tissues the basement membrane is a product of the interaction of several cell types; for example, the glomerular basement membrane is made by both epithelial and endothelial cells. In skeletal muscle, fibroblasts from the endomysium contribute type IV collagen to the assembly of the basement membrane. The formation of the neural basal lamina requires the interaction of Schwann cells and neurons. Further, basement membranes function in development and tissue repair by promoting attachment, migration and proliferation of cells and by mediating signals for tissue interactions.

All basement membranes contain laminin, type IV collagen, entactin and heparan sulfate proteoglycan. Laminin is a large glycoprotein composed of three polypeptide chains, a 400 kD A chain and two B chains of about 200 kD each. The amino-terminal two thirds of the A chain is homologous to the B1 and B2 chains while the carboxy-terminal third has a distinct structure.

Recent studies have revealed that several genetically distinct subunit chains and consequently several laminin isoforms exist. In addition to the EHS laminin chains, A, B1 and B2, merosin (also known as laminin M chain), a homologue of the A chain (Leivo et al., *Proc. Natl. Acad. Sci. USA* 85:1544–1548 (1988); Ehrig et al., *Proc. Natl. Acad. Sci. USA* 87:3264–3268 (1990)), s-laminin (S chain), a homologue of the B1 chain (Hunter et al., Nature 338:229–234 (1989)) and B2t, a truncated homologue of the B2 chain (Kallunki et al., J. Cell Biol. 119:679–693 (1992)), have been characterized. Recently partial sequence of another B1 chain variant in avian eye was reported (O'Rear et al., *J. Biol. Chem.* 267:20555–20557 (1992)). K-laminin and kalinin are laminin isoforms that are present in epithelial basement membranes. K-laminin contains the B1 and B2 chains and has a third 190 kD chain immunologically distinct from the A chain (Marinkovich et al., *J. Cell Biol.* 119:695–703 (1992)). Kalinin has three subunits of which the largest one is immunologically related to one chain of K-laminin (Rouselle et al., *J. Cell. Biol.* 114:567–576 (1991); Marinkovich et al.,*J. Biol. Chem.* 267:17900–17906 (1992)). For terminology of the laminins, see Engvall, 1993, *Kidney International* 43:2–6, which is incorporated herein by reference, and FIG. 13.

Laminin promotes attachment, spreading, motility and growth of a variety of cell types. One of the most striking features of laminin is its capacity to promote outgrowth of neurites from cultured neuronal cells. A major site of cell adhesion and the neurite-promoting activity appear to reside in the globular domain at the end of the long arm of this molecule.

The metastatic propensity of certain tumor cells may also be influenced by laminin. For example, laminin has been shown to mediate the attachment of malignant carcinoma cells to type IV collagen and to increase the metastatic potential of murine melanoma cells. Other basement membrane proteins and their receptors may be involved in the adhesion of metastasizing tumor cells to basement membranes of blood vessels and other epithelial tissues.

Because of the critical role of basement membranes in development, tissue repair, neurite growth and cancer, there exists a need for the identification of new basement membrane components. The present invention satisfies this need.

SUMMARY OF THE INVENTION

This invention provides an isolated nucleic acid molecule encoding a 380–400 KDa subunit of the protein merosin. Also provided are isolated nucleic acid molecules which encode merosin fragments. The invention further provides antibodies, vectors, and the expression of recombinant proteins by use of a host/vector system. The invention also provides the use of merosin to promote neurite growth.

BRIEF DESCRIPTION OF DRAWINGS

FIGS. 1A–1C shows the DNA sequence of a partial merosin polypeptide cDNA (SEQ ID NO: 1) and the deduced amino acid (SEQ ID NO: 2)sequence. Potential N-glycosylation sites are indicated by (▲) and cysteines are circled. Sequences obtained by amino acid sequencing are underlined. Conserved motifs of amino acid sequence are boxed.

FIGS. 3A,, 3B and 3C show immunoblotting of placental extract with antiserum. NaDodSO$_4$ extract of placenta (lanes 1) and the purified fragment of merosin polypeptide from a pepsin digest of placenta (lanes 2) were electrophoresed on a 2–16% gradient acrylamide gel in the presence of NaDodSO$_4$ and transferred to nitrocellulose. The blot in (3A) was stained with a peptide antiserum raised to a 13-amino acid peptide corresponding to residues 476–488 of the merosin polypeptide in FIG. 1 (SEQ ID NO: 2). The blot in (3B) was stained with monoclonal antibody that recognizes COOH-terminal fragments of merosin polypeptide. For comparison, a blot of mouse laminin was stained with anti-laminin (3C). Arrowhead shows the position of the top of the separating gel and numbers (KDa) indicated the positions of molecular weight markers.

FIGS. 4A through 4C-2 show an analysis of intact merosin from placenta. FIG. 4A: NaDodSO$_4$-polyacrylamide gel electrophoresis of rat laminin (lane 1) and the merosin-containing fraction from human placenta (lane 2). Positions of molecular weight markers are shown on the left. FIG. 4B: Electron microscopy after rotary shadowing of the merosin-containing preparation. FIGS. 4C-1 and 4C-2: ELISA in microtiter wells coated with the merosin-containing preparation and in wells coated with the large pepsin fragment of laminin. The antibodies were 3E5

(■; anti-B1), 2E8 (●; anti-B2), 11D5 (Δ; anti-A), and 2G9 (▲; anti-merosin).

Figure 5:
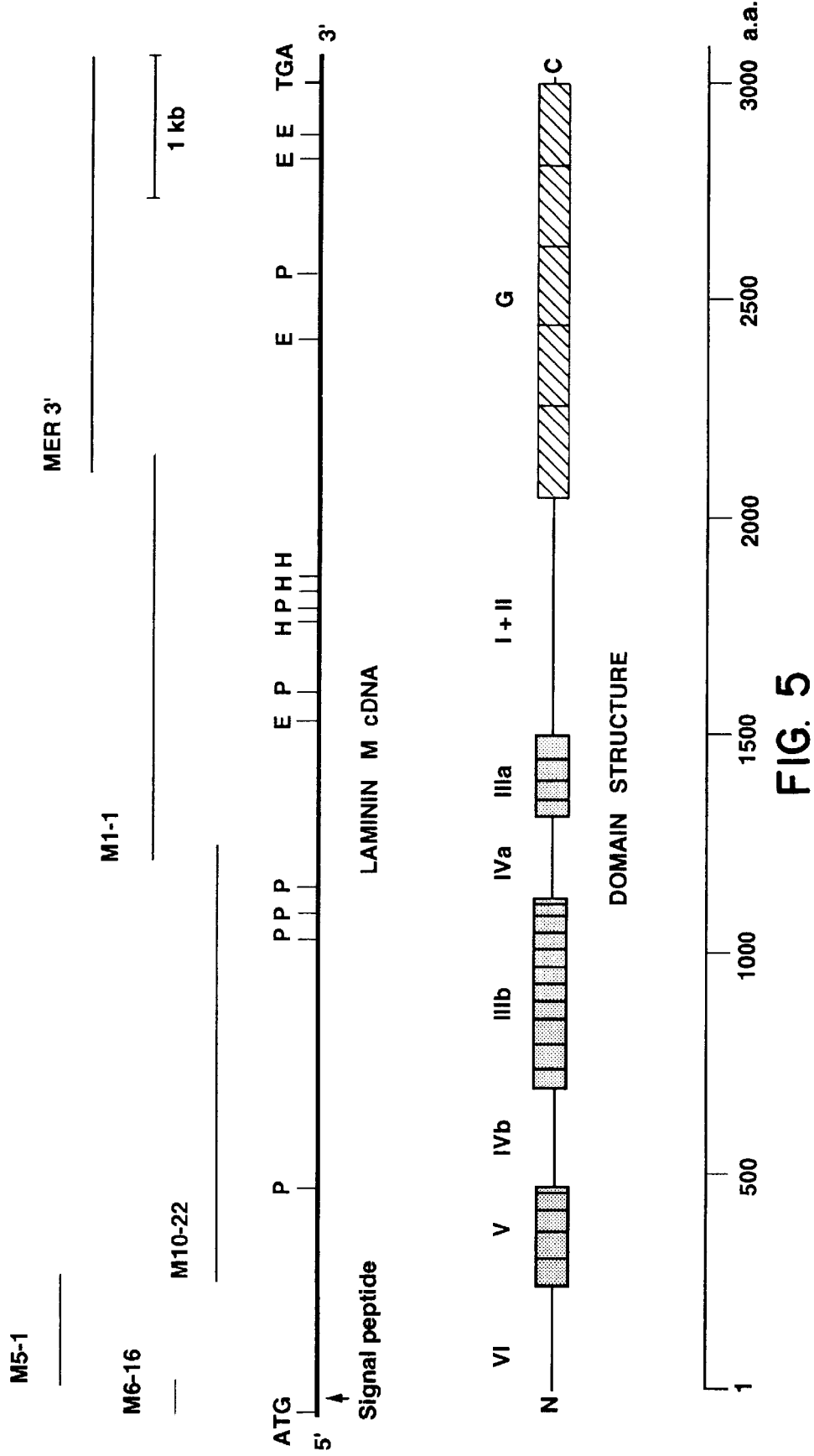

FIG. 5 shows the relative positions of the sequences of cDNA clones for human merosin polypeptide ("laminin M chain"), partial restriction maps and domain structure of the merosin subunit protein. At top, alignment of five overlapping cDNA clones and partial restriction maps of merosin cDNA. ATG indicates the translation initiation signal, and TGA the 3'-end translation stop codon. Restriction enzyme sites EcoRI (E), Hind III (H) and Pst I (P) are shown. Middle, structure of the protein with domains numbered according to Sasaki et al., Proc. Natl. Acad. Sci. USA 84:935–939 (1987); Sasaki et al., J. Biol. Chem. 263:16536–16544 (1988); Sasaki et al., J. Biol. Chem. 262:17111–17117 (1987)), incorporated herein by reference.] Five internal repeats in domain G are indicated by hatched boxes. Domains IIIa, IIIb and V consisting of cysteine-rich EGF modules are shown by shaded boxes. Bottom, scale in amino acids (aa).

Figure 6E:
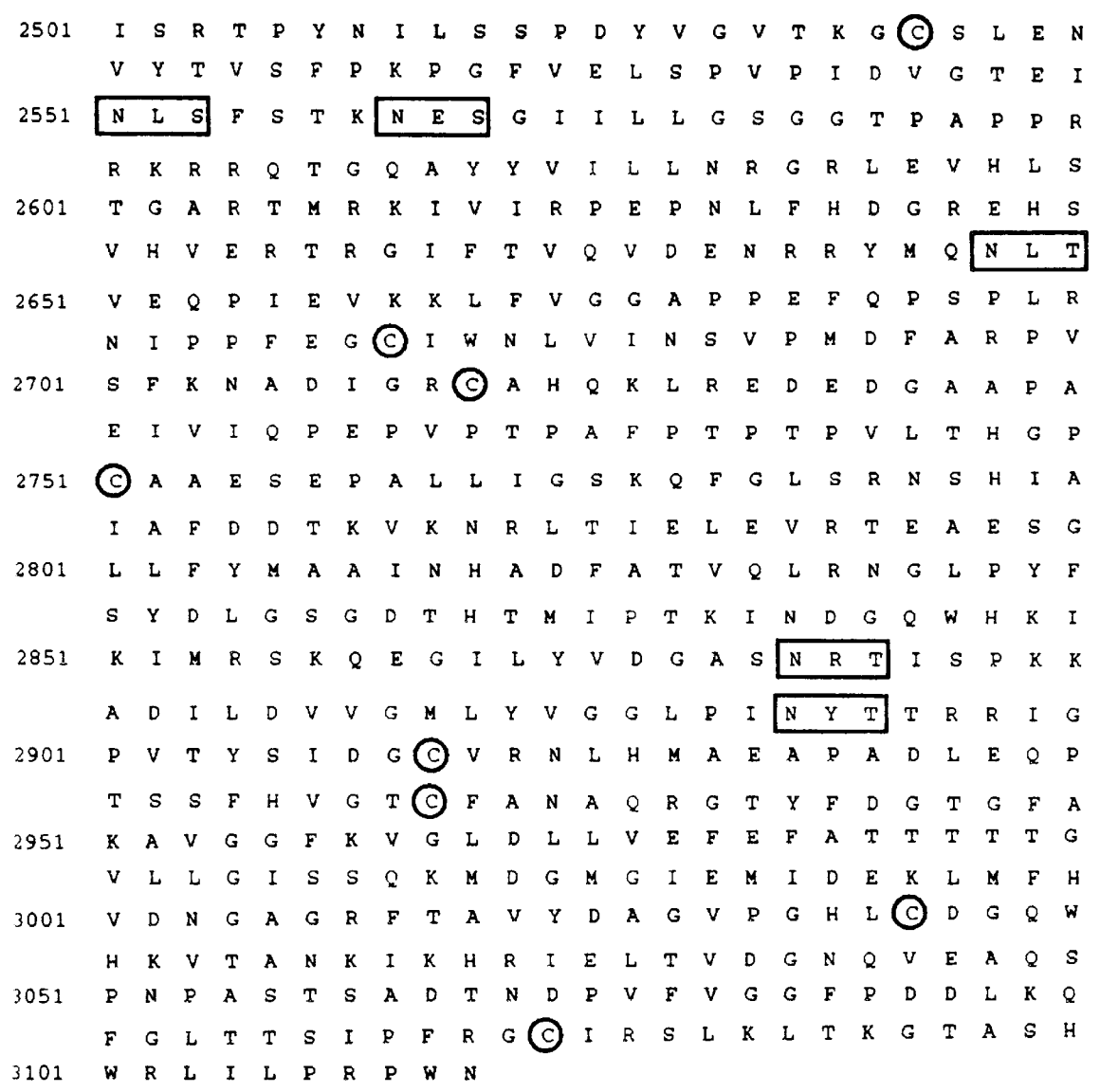

FIGS. 6A–6E shows the complete nucleotide sequence (SEQ ID NO: 3) of human merosin cDNA clones and deduced complete amino acid sequence of the entire protein. First line, nucleotide sequence of cDNA clones characterized in this study. Second line, deduced amino acid sequence from the cDNA clones together with the previously determined carboxyl terminal end amino acid sequence (Ehrig et al., Proc. Natl. Acad. Sci. USA 87:3264–3268 (1990)), incorporated herein by reference. The putative signal peptidase cleavage site is indicated by a triangle. The cysteine residues are circled, and potential attachment sites for asparagine-linked oligosaccharides are boxed.

Figure 7A:
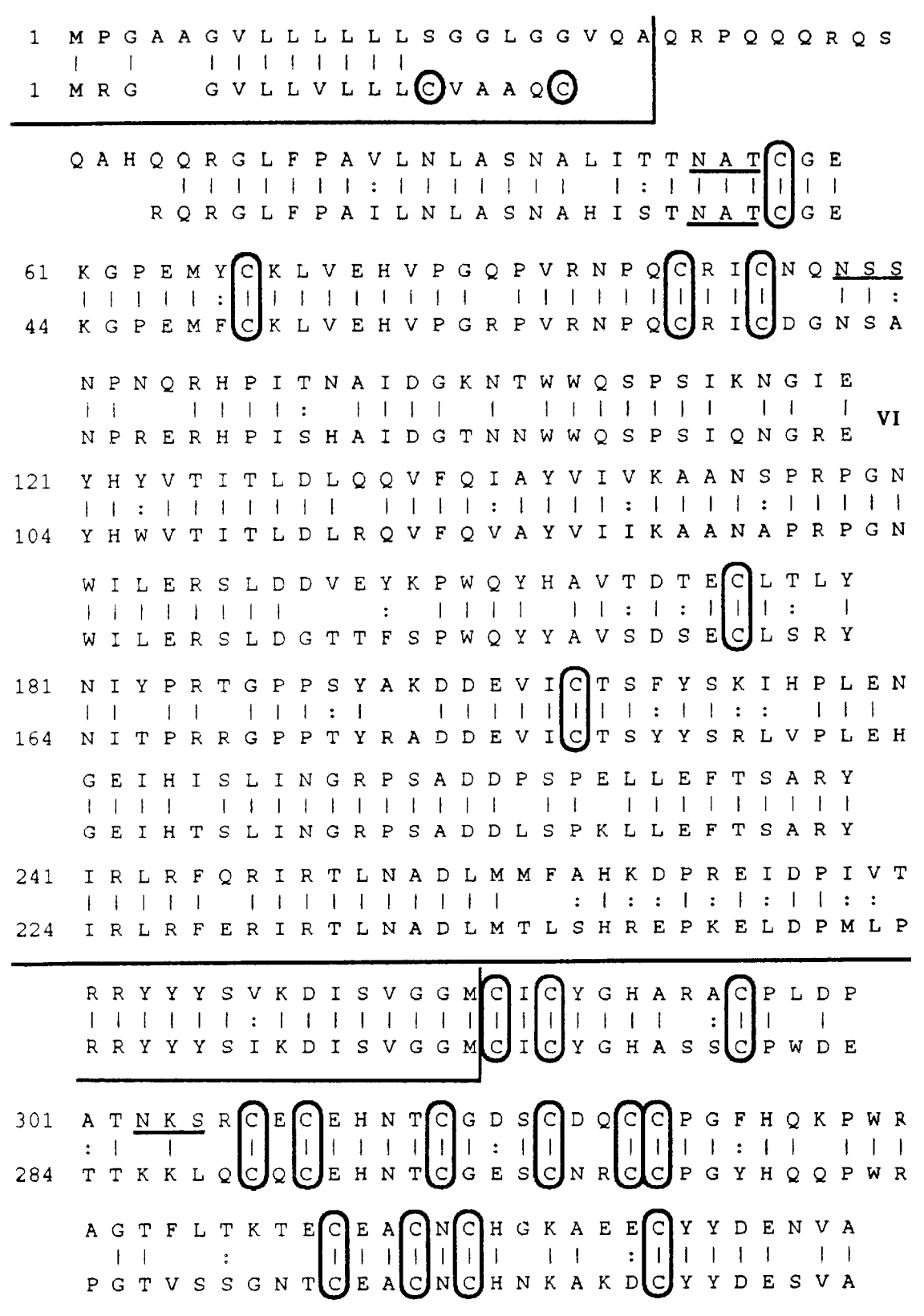
Figure 7B:
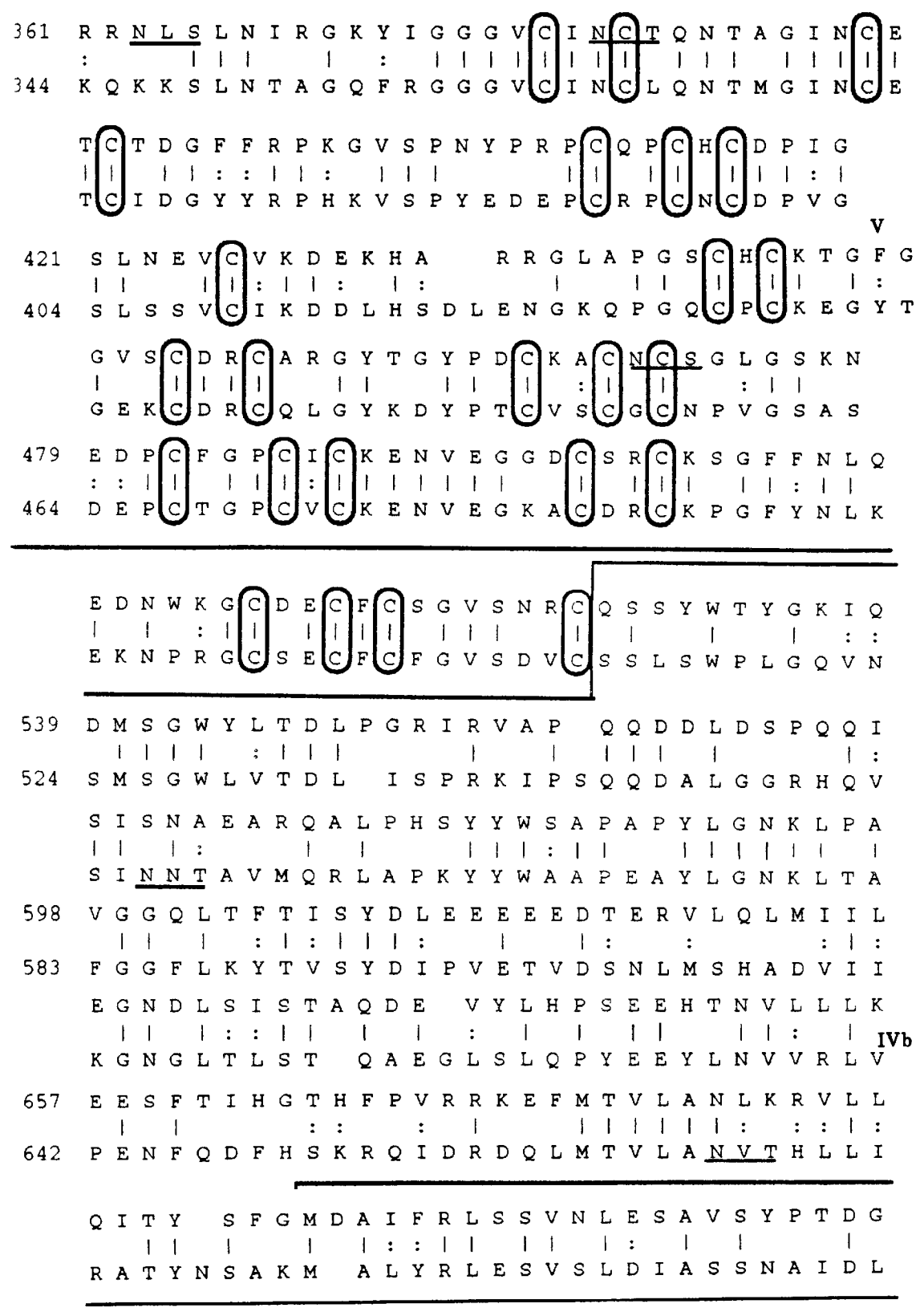
Figure 7C:
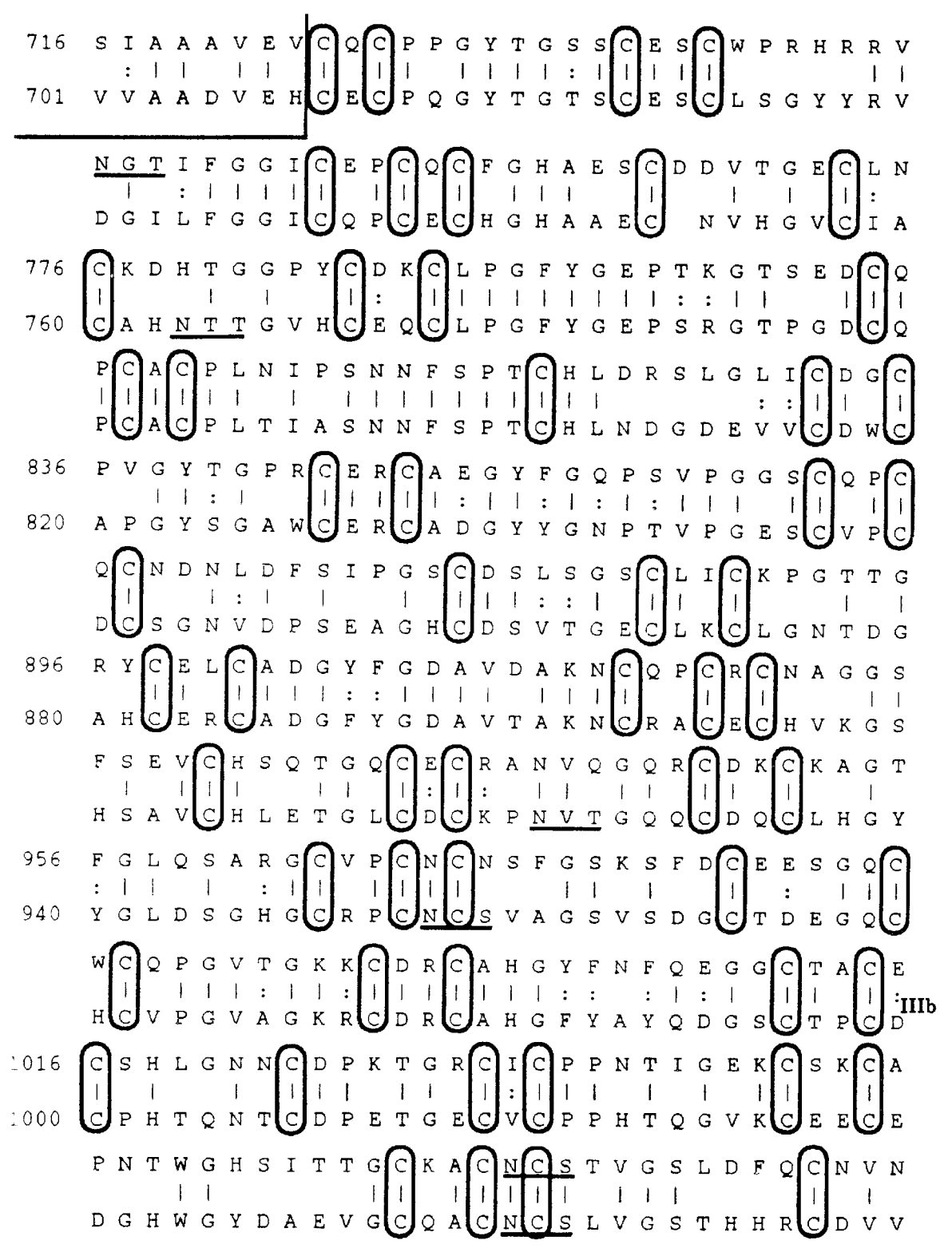
Figure 7D:
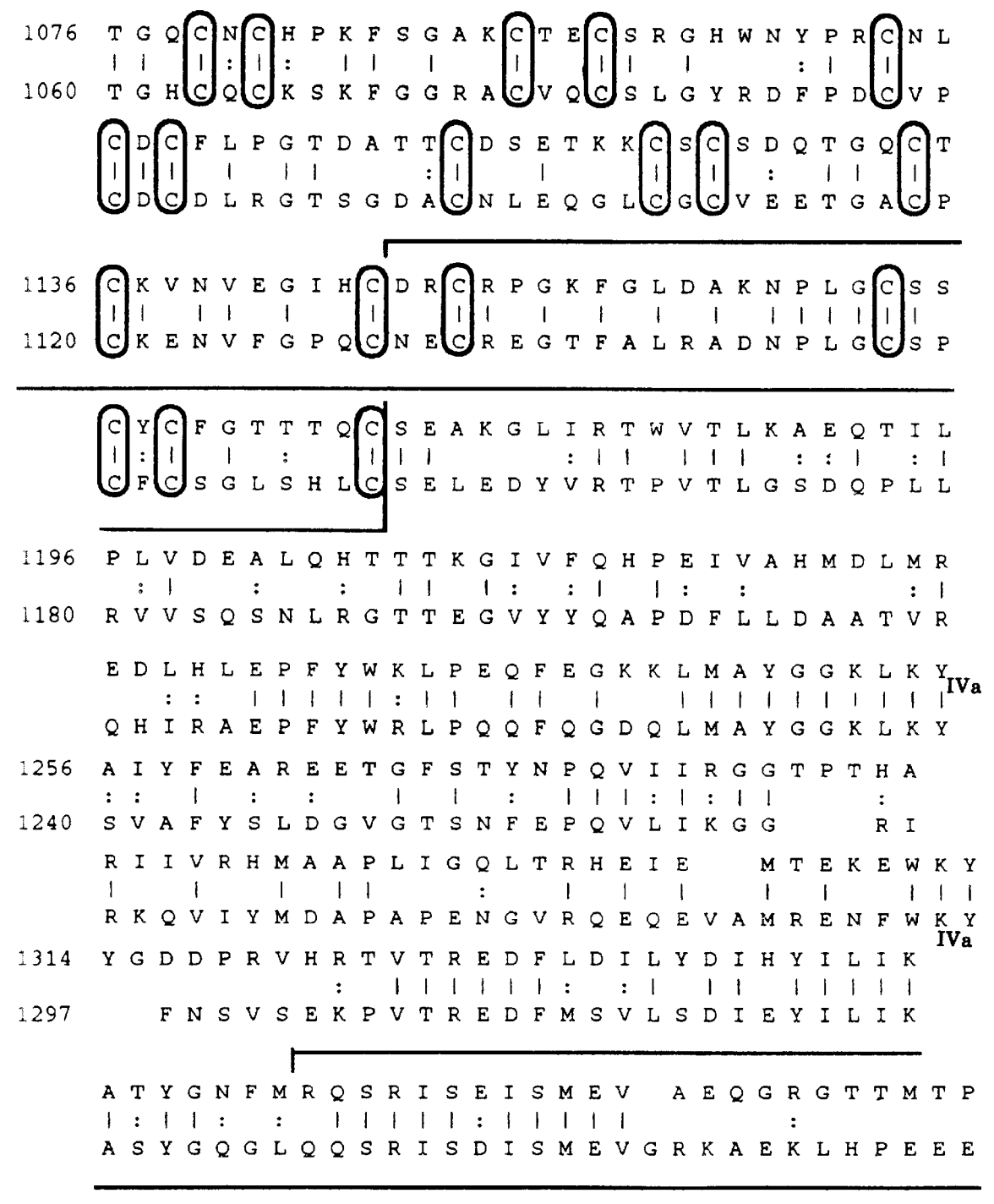
Figure 7E:
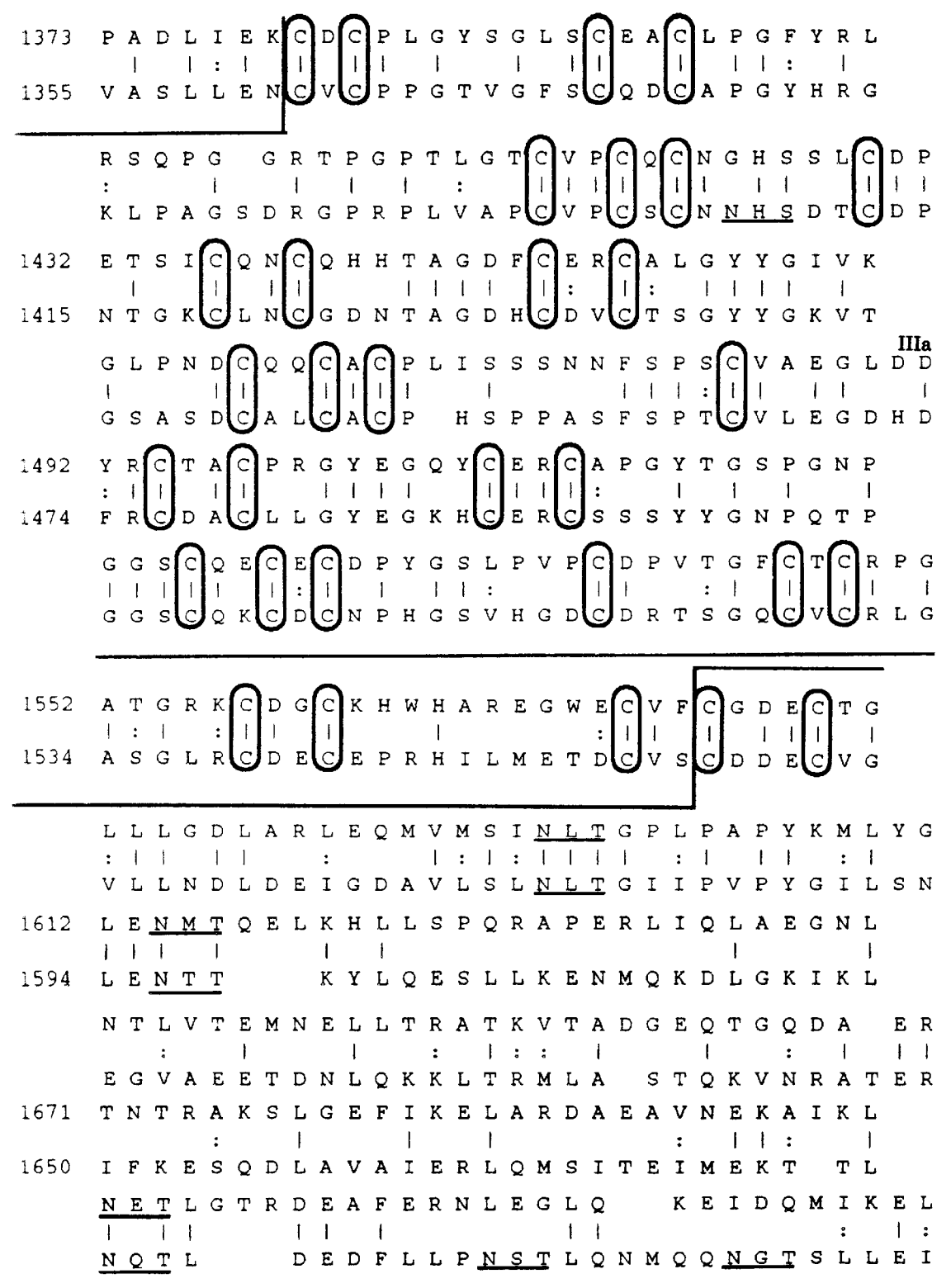
Figure 7F:
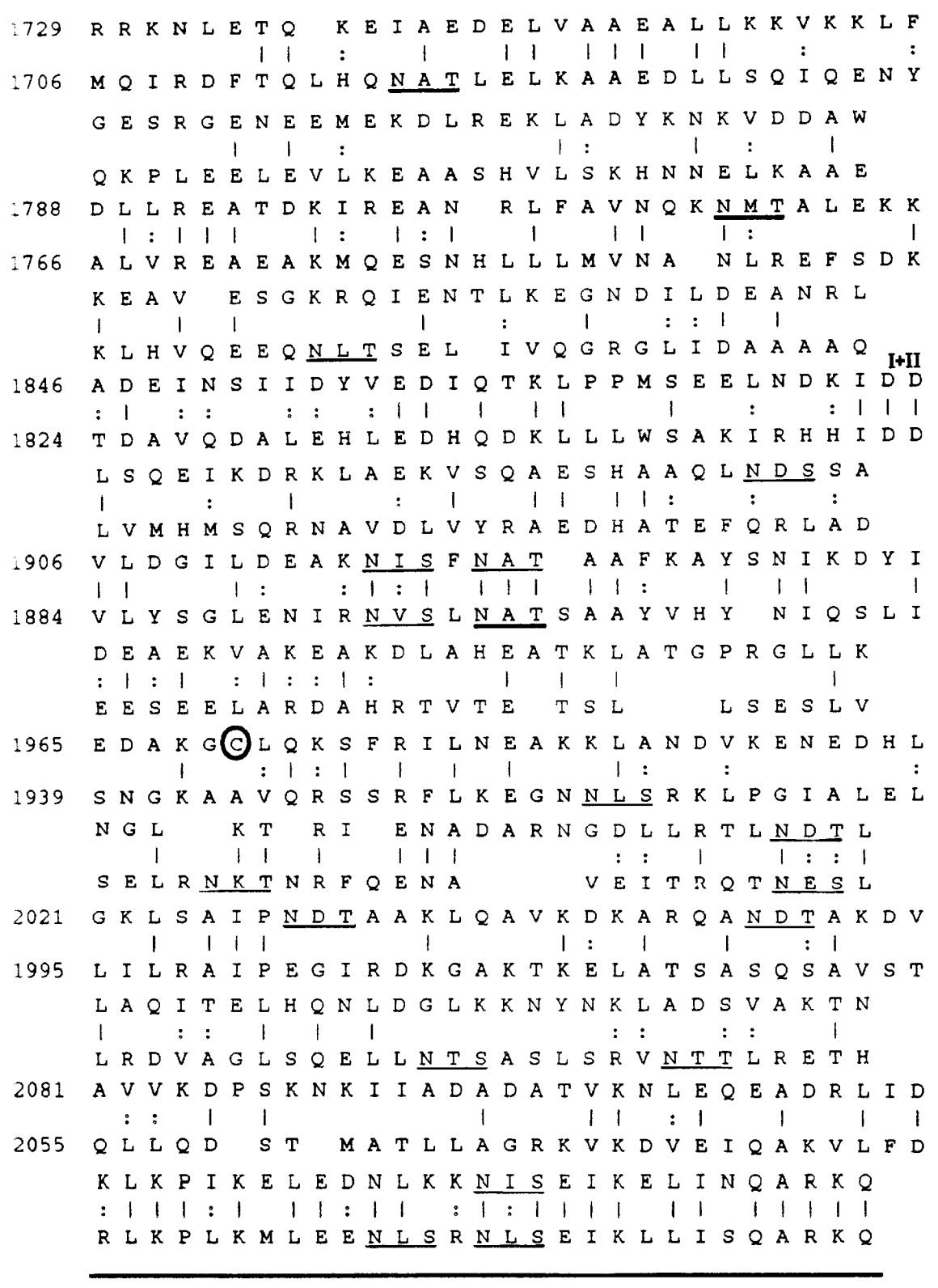
Figure 7G:
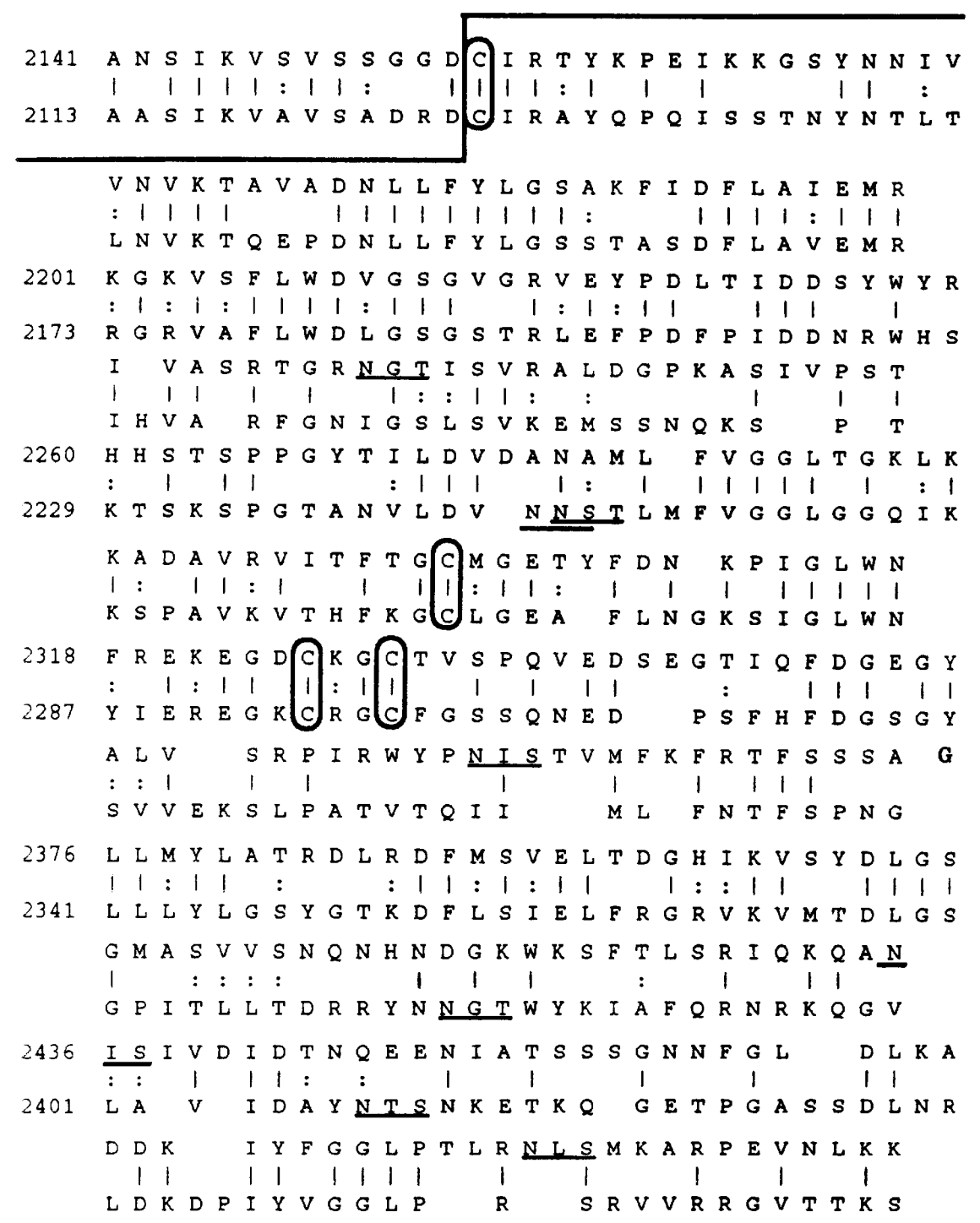
Figure 7H:
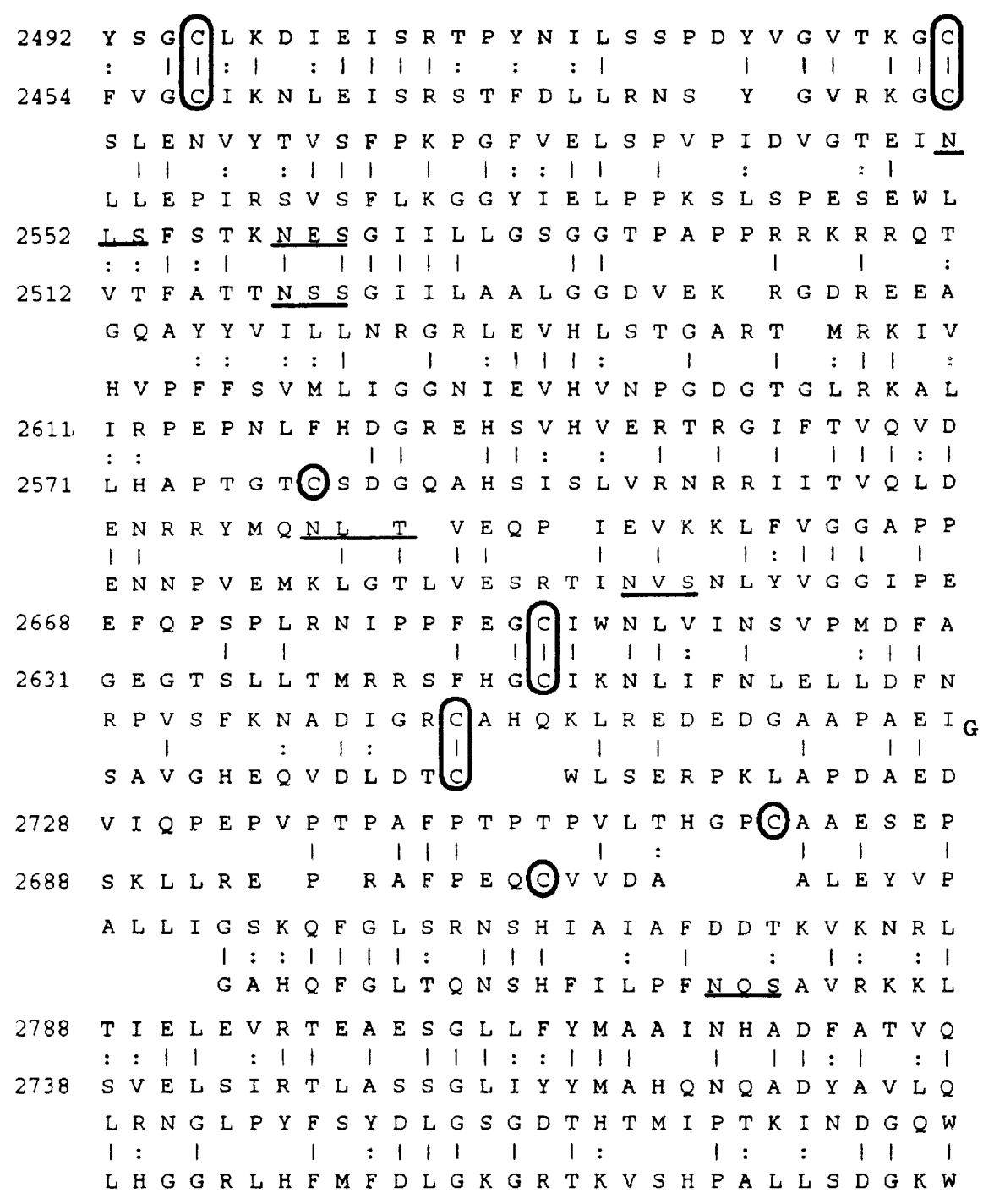

FIGS. 7A–7I are an alignment of amino acid sequences of the M (merosin) (SEQ ID NO: 4) and A (SEQ ID NO: 5) chains of human laminin-type proteins. The upper line shows the amino acid sequence of merosin, and the second line shows the amino acid sequence of the laminin A chain. Both amino acid sequences are numbered from the initiator methionine. All cysteines are circled and N-glycosylation sites are underlined. The structural domains are boxed and indicated by Roman numerals on the right. SP=signal peptide.

Figure 8:
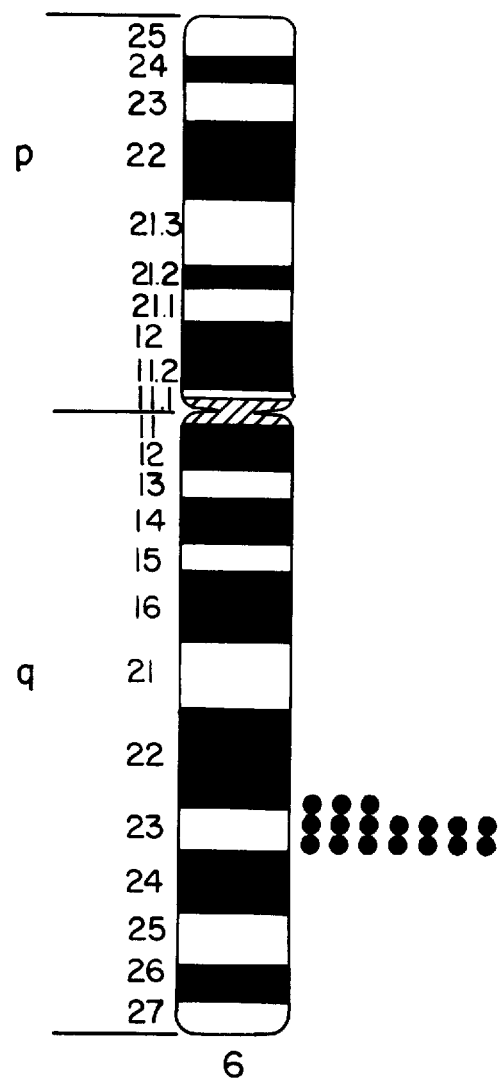

FIG. 8 shows the chromosomal localization of the merosin encoding sequences. The idiogram of chromosome 6 shows the distribution of signals on that chromosome and assignment of the merosin gene to 6q22→23.

Figure 9A:
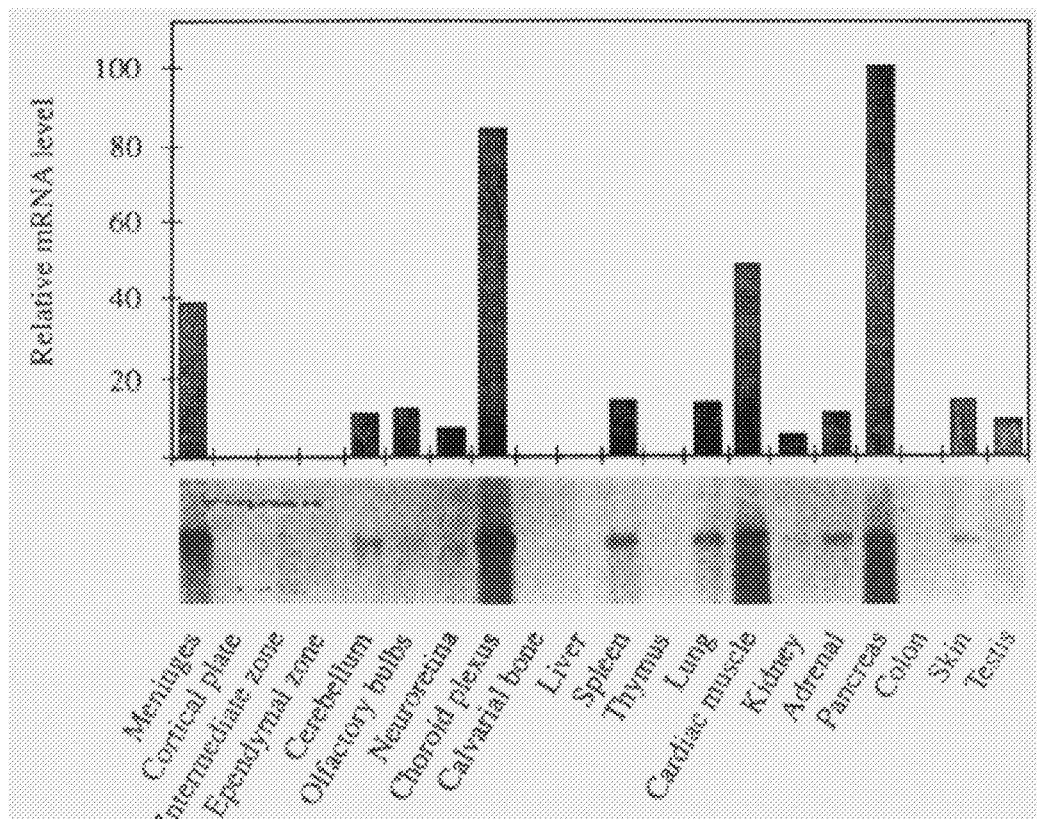
Figure 9B:
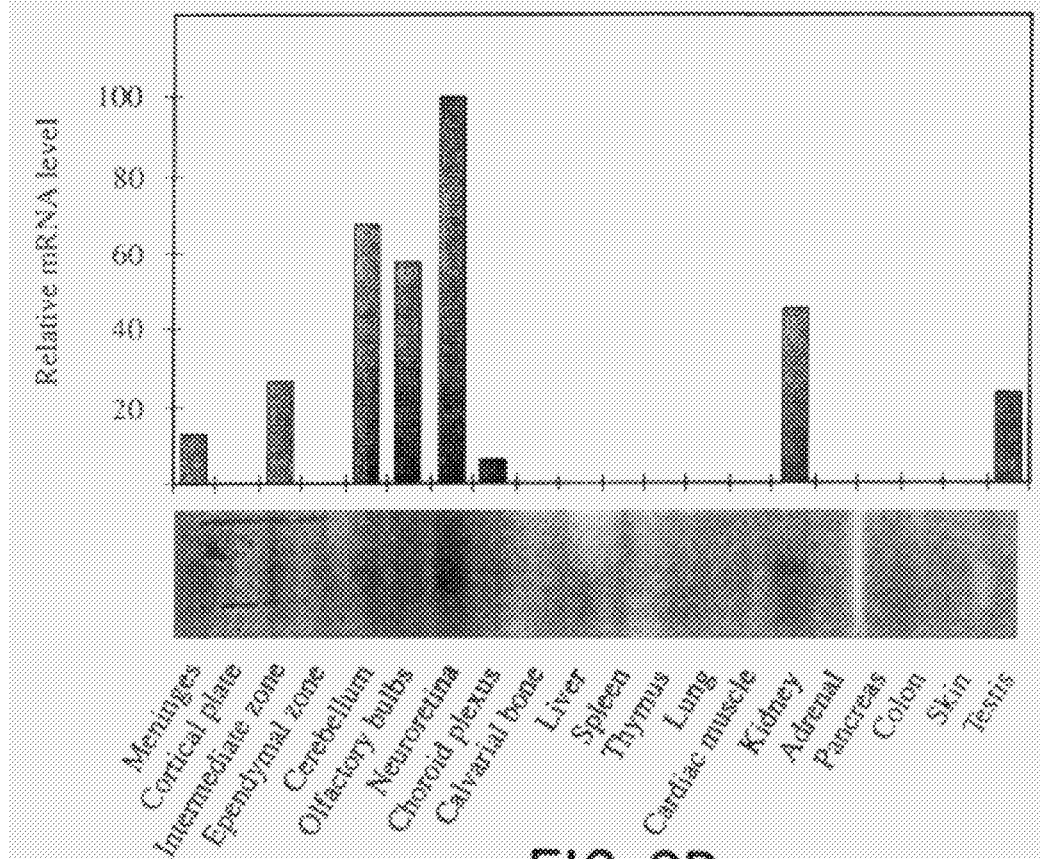

FIGS. 9A and 9B show expression of merosin and laminin A chain mRNA in 17-week-old human fetal tissues. Gene Screen Plus filter containing total RNA (~10 μg) was prepared and hybridized as described Example V below. Ethidium bromide (EtBr) staining of the filter (bottom) is shown to illustrate the relative amounts of RNA in each lane.

FIGS. 10A through 10H show in situ hybridization of merosin mRNA in 17-week-old fetal tissues. In kidney (FIGS. 10A and B) signals are seen in mesenchymal cells adjacent to condensing pretubular cells and ureter-derived tubules (t) in the outer cortex. Secretory tubules of the nephron and blood vessels are negative. In heart muscle (FIGS. 10C and D) signals can be observed in cardiomyocytes throughout the muscle. In sections of skin (FIGS. 10E and F) no grains are seen over the epithelial cells of epidermis (e), while strong signal can be observed in the condensing papillary mesenchymal cells (p) and a developing hair follicles (f). In lung (FIGS. 10G and H) signals are present in smooth muscle cells of the peribronchial arterial wall, but alveolar and bronchial cells are negative. Bar A–D 200 μm and E–H 100 μm.

Figure 11:
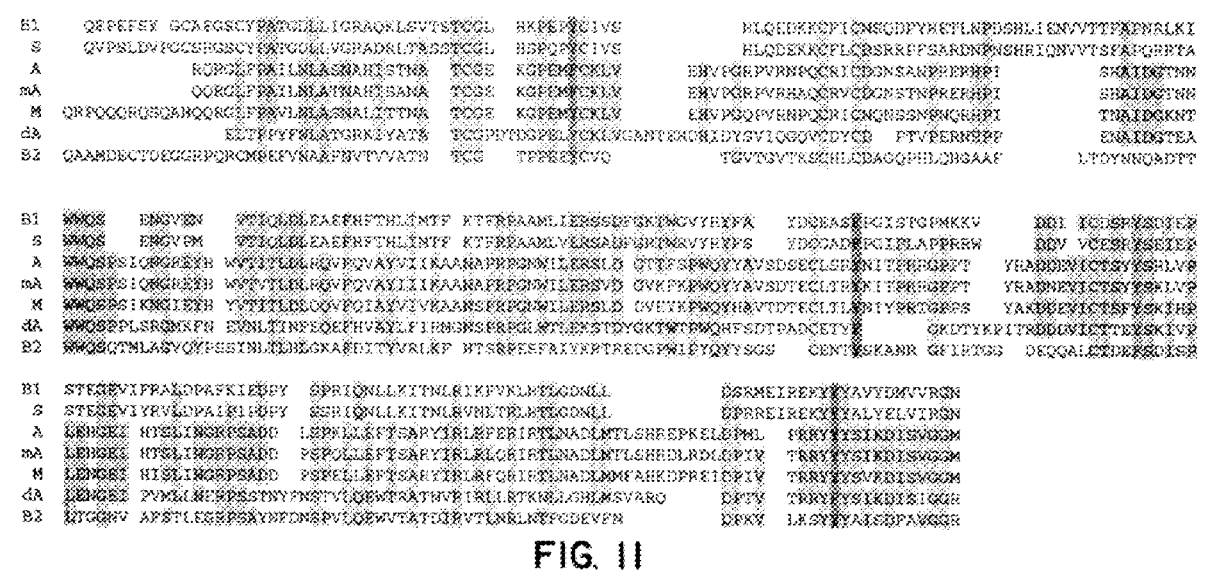

FIG. 11 is an alignment of domains VI of the known human A- and B-type laminin chains, the rat S chain, the mouse A chain and the Drosophila A chain. Amino acids that are identical in half of the chains are shaded, and dark shading indicates conserved change Phe (F)<-->Tyr (Y). Abbreviations: B1, human B1 chain (SEQ ID NO: 6); S, rat S chain (SEQ ID NO: 7); A, human A chain (SEQ ID NO: 8); mA, mouse A chain (SEQ ID NO: 9); M, human M chain (SEQ ID NO: 10); B2, human B2 chain (SEQ ID NO: 12); dA, Drosophila A chain (SEQ ID NO: 11).

Figure 1B:
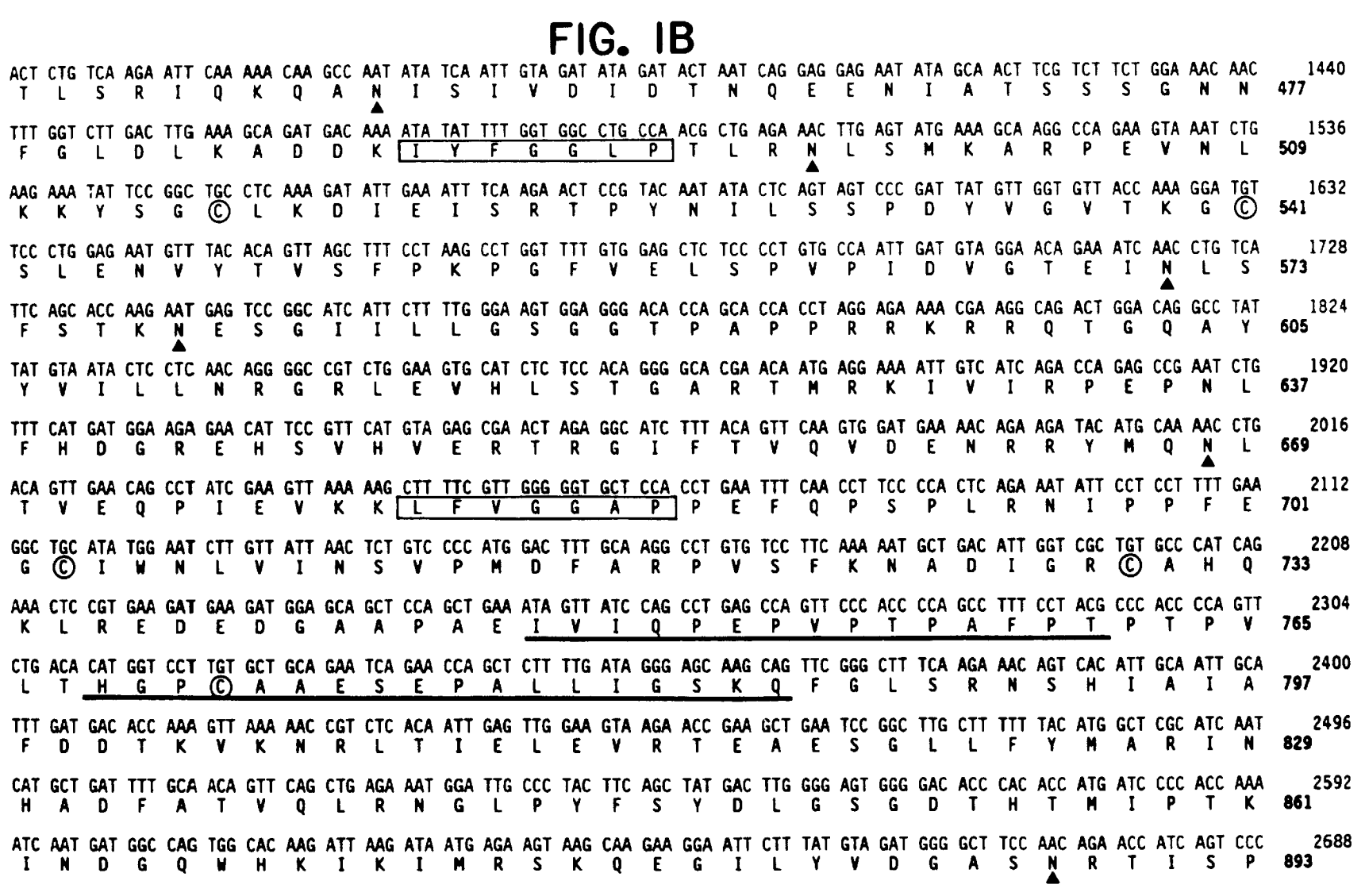
Figure 2:
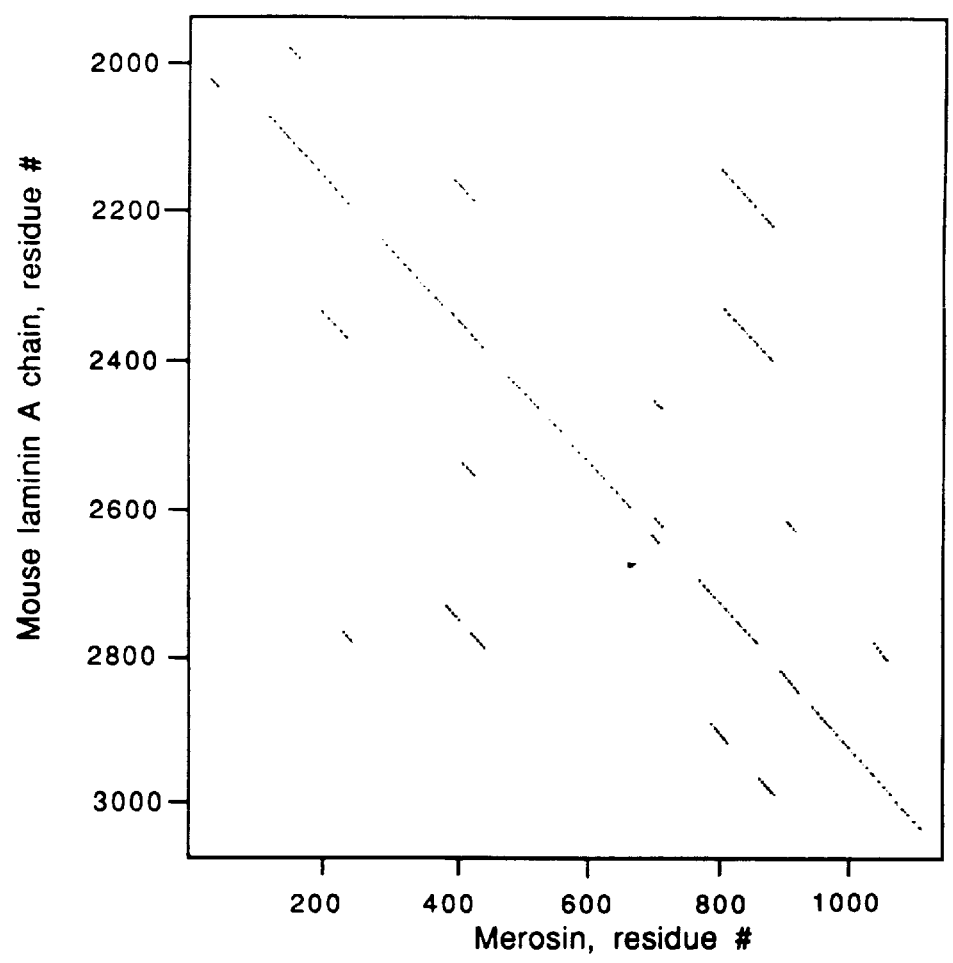
FIG. 2 shows a comparison of the amino acid sequences of merosin fragment and the COOH-terminal portion of the mouse laminin A chain by dot matrix plotting. Sequences were compared using the Micro Genie matrix comparison program. The frame was set at eight amino acids with a minimal match of 40%.
Figure 4A:
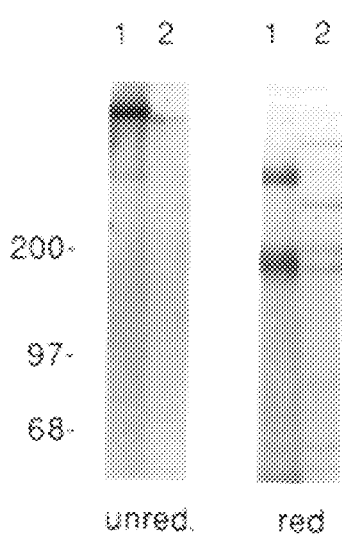
Figure 4B:
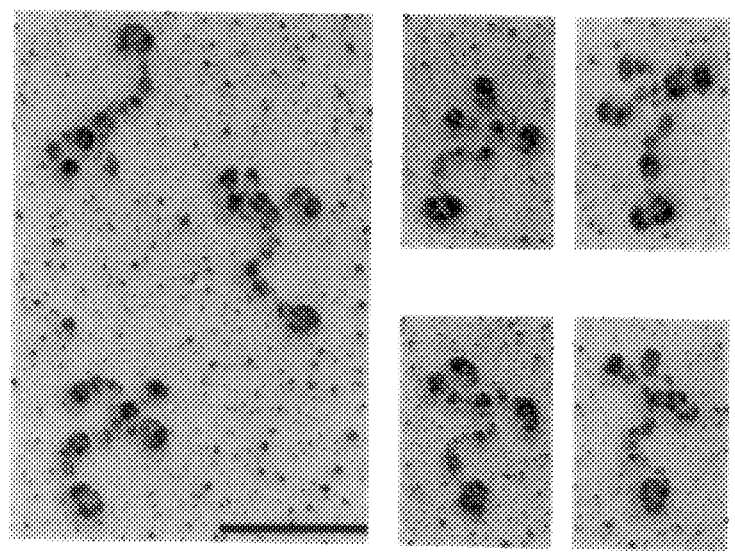
Figures 1, 4C:
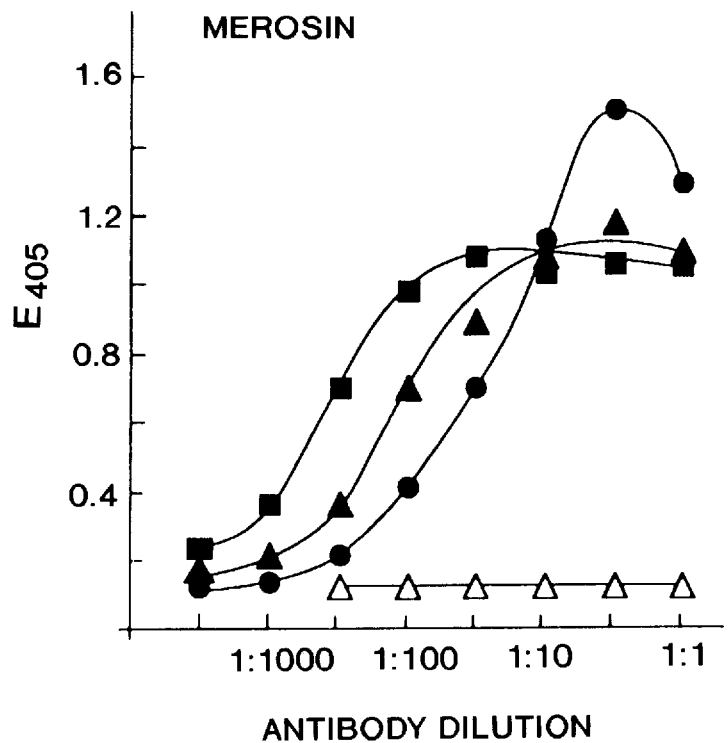
Figures 2, 4C:
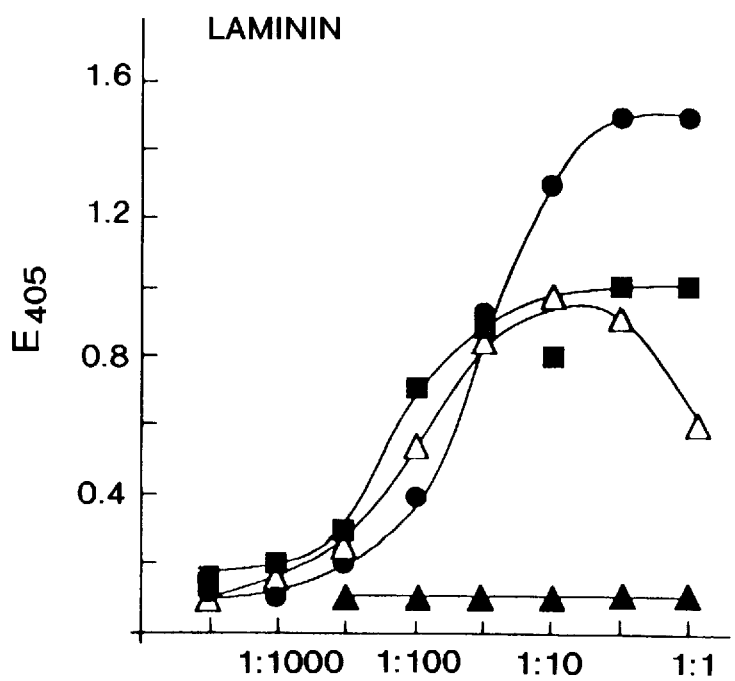

FIGS. 12-1 and 12-2 are an alignment of domains V of the known human A- and B-type chains, the rat S chain, the mouse A chain and the Drosophila A chain. Amino acids that are identical in half of the chains are shaded, and dark shading indicates conserved change Phe (F)<-->Tyr (Y). Abbreviations: B1, human B1 chain (SEQ ID NO: 14); S, rat S chain (SEQ ID NO: 14); A, human A chain (SEQ ID NO: 15); mA, mouse A chain (SEQ ID NO: 16); M, human M chain (SEQ ID NO: 17); B2, human B2 chain (SEQ ID NO: 18); dA, Drosophila A chain (SEQ ID NO: 19); B2t, human B2t chain (SEQ ID NO: 20).

Figure 13:
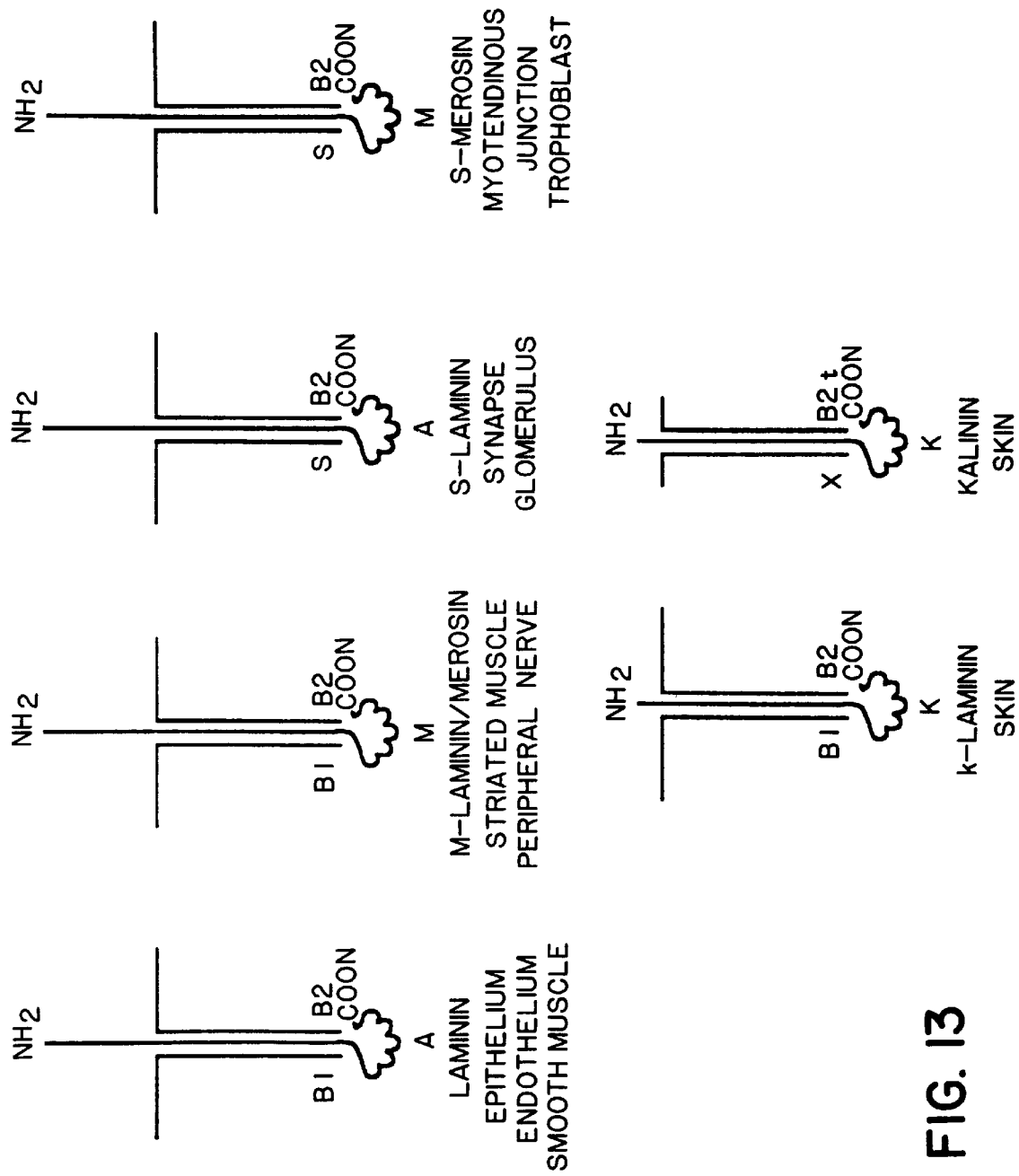

FIG. 13 is a diagramatic scheme of the structure of the laminins.

DETAILED DESCRIPTION OF THE INVENTION

This invention provides a cDNA molecule (SEQ ID NO: 3) encoding the major subunit of human merosin protein which is structurally related to laminin. The merosin protein has an apparent molecular weight of about 800 kd and is composed of four polypeptides having apparent molecular weights of 300, 200, 200 and 80 kD, the 300 kD polypeptide being joined to the 200 kD polypeptides by disulfide bonds, and the 300 kD and 80 kD polypeptides comprising the 380–400 KDa merosin subunit having substantially the amino acid sequence shown in FIG. 6. Merosin is found in placenta, striated muscle, peripheral nerve, trophoblasts and human Schwann cell neoplasms, among other tissues.

Leivo et al., Proc. Natl. Acad. Sci. USA 85:1544–1548 (1988), which is incorporated herein by reference, describes the isolation of a 65-KDa and an 80 KDa segment of the basement-membrane-associated polypeptide merosin. These two precursor segments, the full length merosin polypeptide, fragments of the merosin polypeptide, and proteins comprising any of these segments, polypeptide, or fragments have also been termed merosin. Because the 65 KDa and 80 KDa proteins appear to be segments of the 380–400 KDa merosin polypeptide contained within an 800 KDa protein complex, the term merosin has now also been applied to the 800 KDa protein described herein. The 380–400 KDa subunit is designated merosin polypeptide, merosin subunit, M chain, or laminin M chain.

It is understood that limited modifications may be made to the primary sequence of merosin subunit (SEQ ID NO: 3) without destroying its biological function, and that only a portion of the entire primary structure may be required in order to effect activity. One such biological active fragment is a molecule having substantially the sequence shown in FIG. 1 (SEQ ID NO: 2). In a separate embodiment of the invention, the merosin subunit has an amino acid sequence substantially similar to that shown in FIG. 6 (SEQ ID NO: 1). Minor modifications of these sequences which do not destroy the activity of the proteins also fall within the definition of merosin and within the definition of the protein claimed as such. Moreover, fragments of the sequences of FIGS. 1 or 6, but not a fragment consisting solely of the previously described 80 Kd fragment, which retain the function of the entire protein, as determined by the merosin activity assay described in Example II below, and as defined by the protein's ability to elicit merosin-specific antibodies are included within the definition. It is understood that minor modifications of primary amino acid sequence may result in proteins which have substantially equivalent or enhanced function as compared to the sequences set forth in FIGS. 1 or 6. These modifications may be deliberate, as through site-directed mutagenesis, or synthesis of merosin analogs, or may be accidental such as through mutation in hosts which are merosin producers. All of these modifications are included as long as merosin biological function is retained. The nucleic acid sequences shown in FIGS. 1 and 6 are useful in the production of recombinant merosin and merosin fragments. Nucleic acid fragments of at least 10 nucleotides are also useful as hybridization probes. The probes are useful to identify tissue (as set forth in more detail below) to isolate the genomic gene encoding merosin, which has now been localized to chromosome 6q22→23, or to identify nucleic acid encoding merosin-like proteins. The isolated nucleic acid fragments also are useful to generate novel peptides. These peptides, in turn, are useful as immunogens for the generation of polyclonal and monoclonal antibodies. Methods of preparing and using the probes and immunogens are well known in the art, and are briefly described below.

Also included within the scope of this invention are nucleic acid molecules that hybridize under stringent conditions to the nucleic acid molecules, the sequences of which are shown in FIGS. 1 and 6. Such hybridizing nucleic acid molecules or probes, can by prepared, for example, by nick translation of the nucleic acid molecules of FIGS. 1 or 6, in which case the hybridizing nucleic acid molecules can be random fragments of the molecules, the sequences of which are shown in FIGS. 1 and 6. For methodology for the preparation of such fragments, see Sambrook et al., *Molecular Cloning: A Laboratory Manual* Cold Spring Harbor Press, Cold Spring Harbor, N.Y. (1989), incorporated herein by reference. As used herein, "nucleic acid" shall mean single and double stranded DNA and RNA.

Further, various molecules can be attached to merosin subunit, for example, other proteins, carbohydrates, or lipids. Such modifications are included within the definition of merosin.

"Purified", when used to describe the state of merosin, denotes the protein free of a portion of the other proteins and molecules normally associated with or occurring with merosin in its native environment. As used herein the term "native" refers to the form of a protein, polypeptide, antibody or a fragment of thereof that is isolated from nature or that which is without an intentional amino acid substitution.

As used herein, the term "antibody" or "immunoglobulin" refers to a protein that is produced in response to immunization with an antigen and specifically reacts with the antigen. This includes polyclonal as well as monoclonal antibodies. Human and mammalian, for example, mouse, rat, rabbit and goat, are intended to be included in this definition. The most predominant human antibody produced is of the IgG isotype, having two light and two heavy chains linked by disulfide bonds, which constitute about 80% of total serum antibodies.

As used herein, "antibody" also encompasses fragments of antibodies. The antibody fragments retain at least some ability to selectively bind with its antigen. Also encompassed by this invention are antibody fragments that have been recombinantly or chemically synthesized that retain the ability to bind the antigen of the corresponding native antibody. The ability to bind with an antigen or hapten is determined by antigen-binding assays known in the art such as antibody capture assays (See, for example, Harlow and Lane, *Antibodies, A Laboratory Manual*, Cold Spring Harbor Laboratory, Cold Spring Harbor, N.Y. (1988)). Antibody fragments retaining some binding affinity include, but are not limited to: Fab (the fragment which contains a monovalent antigen-binding fragment of an antibody molecule produced by digestion with the enzyme papain to yield an intact light chain and a portion of one heavy chain); Fab' (the fragment of an antibody molecule obtained by treating with pepsin, followed by reduction, to yield an intact light chain and a portion of the heavy chain; two Fab' fragments are obtained per antibody molecule); $(Fab')_2$, the fragment of the antibody that is obtained by treating with the enzyme pepsin without subsequent reduction; $F(ab')_2$ is a dimer of two Fab' fragments held together by two disulfide bonds; Fv and single chain antibodies (SCA).

"Isolated" when used to describe the state of the nucleic acids encoding merosin, denotes the nucleic acids free of at least a portion of the molecules associated with or occurring with nucleic acids in the native environment.

"Recombinant expression vector" includes vectors which are capable of expressing DNA sequences contained therein, where such sequences are operatively linked to other sequences capable of effecting their expression. It is implied, although not always explicitly stated, that these expression vectors must be replicable in the host organisms either as episomes or as an integral part of the chromosomal DNA. In sum, "expression vector" is given a functional definition, and any DNA sequence which is capable of effecting expression of a specified DNA sequence disposed therein is included in this term as it is applied to the specified sequence. In general, expression vectors of utility in recombinant DNA techniques are often in the form of "plasmids" which refer to circular double stranded DNA loops which, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Host-vector system" refers to cells which have been transfected with vectors constructed using recombinant DNA techniques. The vectors and methods disclosed herein are suitable for use in host cells over a wide range of procaryotic and eucaryotic organisms.

Reference is made to standard textbooks of molecular biology that contain definitions and methods and means for carrying out basic techniques, encompassed by the present invention. See, for example, Maniatis et al., *Molecular Cloning: A Laboratory Manual*, Cold Spring Harbor Laboratory, N.Y. (1982) and Sambrook et al., *Molecular Cloning: A Laboratory Manual*, Cold Spring Harbor Laboratory, N.Y. (1989) and the various references cited therein. This reference and the cited publications are expressly incorporated by reference into this specification.

In addition, recombinant DNA methods currently used by those skilled in the art include the polymerase chain reaction (PCR) which, combined with the synthesis of oligonucleotides, allows easy reproduction of DNA sequences. A DNA segment of up to approximately 6000 base pairs in length may be amplified exponentially starting from as little as a single gene copy by means of PCR. In this technique a denatured DNA sample is incubated with two oligonucleotide primers that direct the DNA polymerase-dependent synthesis of new complementary strands. Multiple cycles of synthesis each afford an approximate doubling of the amount of target sequence. Each cycle is controlled by varying the temperature to permit denaturation of the DNA strands, annealing the primers, and synthesizing new DNA strands. The use of a thermostable DNA polymerase eliminates the necessity of adding new enzyme for each cycle, thus permitting fully automated DNA amplification. Twenty-five amplification cycles increase the amount of target sequence by approximately $10^6$-fold. The PCR technology is the subject matter of U.S. Pat. Nos. 4,683,195, 4,800,159, 4,754,065, and 4,683,202 all of which are hereby incorporated by reference.

With regard to the present invention, the cDNA shown in FIGS. 1 (SEQ ID NO: 1) or 6 (SEQ ID NO: 3), or any portion of them can be reproduced for cloning and expression purposes by amplifying the desired sequence with PCR and cloning it into a suitable vector as is well known in the art.

Detection methods for the presence of nucleic acid or protein in cells include hybridization of a nucleic acid probe with the nucleic acid of a cell and cell staining with polyclonal or monoclonal antibodies. Such techniques are accomplished by methods well-known to those skilled in the art. See, for example, Harlow and Lane, *Antibodies: A Laboratory Manual*, Cold Spring Harbor, 1988, hereby incorporated by reference.

Monoclonal and polyclonal antibodies against merosin were prepared according to procedures well known in the art. The specificity of the antibodies is examined by carrying out enzyme immunoassays and immunoblotting of placental extracts.

For example, monoclonal antibodies are prepared by immunizing an animal with material containing the protein, such as an extract of human placenta tissue, followed by isolating antibody-producing hybridoma cells, as is well known in the art. (See, for example, Harlow and Lane, *Antibodies: A Laboratory Manual*, supra, and the references cited therein, all which are incorporated by reference into this specification.) Anti-merosin antibodies are selected by performing immunofluorescence analysis of tissue sections where merosin is localized in the basement membranes of trophoblasts, striated muscle and Schwann cells, and other sites. The identification of antibodies is confirmed by immunoblotting and immunoprecipitation which reveals one or more of the polypeptides described above. The appropriate hybridoma is reactive with purified merosin subunit or merosin fragments. Merosin fragments can be prepared by expressing the merosin cDNA shown in FIG. 1, or alternatively, subjecting the cDNA molecules, the sequences of which are shown in FIGS. 1 and 6, to restriction enzyme digestion and subsequent purification of the restriction enzyme fragments. These methods are well known to those of skill in the art, Sambrook et al., supra, hereby incorporated by reference. The nucleic acid fragments are then expressed in a procaryotic or eucaryotic expression vector as described above.

Alternatively, anti-merosin antibodies can be prepared by immunizing an animal with synthetic peptides or recombinant protein fragments prepared from molecules having the sequences shown in FIGS. 1 or 6, or from restriction enzyme fragments, described above. One molecule demonstrated to be suitable for antibody production is the molecule having the sequence shown in FIG. 1 (SEQ ID NO: 1). A synthetic peptide suitable for antibody production is described in Example I. Selection of anti-merosin antibodies is performed as described above.

The COOH-terminal portion of merosin is structurally related to the COOH-terminus of the laminin A-chain. However, the amino acid sequence of merosin is 61% and 62% different from the homologous portions of mouse and human laminin A chains, respectively. Affinity purified antibodies stain two bands, suggesting that the merosin polypeptide is processed into two fragments of approximately 300 kD and 80 kD respectively. cDNA clones for merosin A chain were isolated from a human placental lambda gtll cDNA expression library using affinity purified antibodies specific for merosin. Two cDNA clones, designated 271 and 225, with inserts of 3.6 and 1.7 kb respectively were selected for sequencing. The nucleic acid sequence of the cDNA revealed a 3.4 kb open reading frame followed by a 155 bp untranslated 3' region. The cDNA and deduced amino acid sequences are shown in FIG. 1. $NH_2$-terminal amino acid sequences of the fragments isolated from peptic or chymotryptic digests of placenta, and the $NH_2$-terminal amino acid sequences of a 16 kD fragment generated with thrombin were contained within the deduced sequence, thus defining the clones as merosin cDNA. RNA blot analysis revealed a single transcript of about 10 kb in human placental RNA.

The deduced partial sequence of merosin comprises 1130 amino acids and contains 13 potential sites of N-glycosylation. The sequence includes five repeats of about 190 amino acids. These repeats contain a conserved seven amino acid long sequence, LFVGGLP (SEQ ID NO: 21) or variations thereof. This is followed 17–21 and 40–43 residues later by cysteines most of which are preceded by glycines. The average identity among the five repeats is about 25%.

Comparative analysis of the amino acid sequence of merosin with known proteins revealed a striking similarity to the mouse and human laminin A chains. No other significant similarities were found upon search of the data banks. The five repeats of merosin are also present in the COOH-terminal portion of the laminin A chain. The overall identity between the merosin sequence in FIG. 1 and the corresponding portion of the mouse laminin A chain is 39%.

The partial cDNA clone, the sequence of which is provided in FIG. 1 (SEQ ID NO: 1), was used to isolate the full length sequence encoding merosin polypeptide. Several libraries were made from human placental poly(A) RNA and probed with merosin-encoding sequences. Five overlapping cDNA inserts were pieced together to generate the full length sequence, which is shown in FIG. 6 (SEQ ID NO: 3).

The human M chain is 30 residues longer than the human A chain, which contains 3058 residues. Comparison of the two sequences demonstrates that the domain structure of the M chain is similar to that of the A chain, and these two laminin heavy chains have considerable homology. The overall sequence similarity is 46.6%, and 58.6% when conservative changes are included.

Expression of the M and A chain genes was compared by Northern hybridization; in situ hybridization was also conducted for the M chain in human fetal tissue. Both procedures confirmed the different tissue expression pattern of these polypeptides.

It has further been discovered that malignant tumors have an insubstantial amount of merosin compared to non-malignant tumors. The precise amount of merosin depends on the specific tumor and can be determined by one skilled in the art given the teaching of this invention.

The following examples are intended to illustrate but not to limit the invention.

EXAMPLE I

Purification of Merosin

Screening of cDNA Library

A human placental cDNA library in lambda gt11 was screened using affinity purified antibodies to the denatured 65 kD chymotrypsin fragment of merosin as described in Leivo and Engvall, supra. The identity of the isolated cDNA clones was confirmed immunologically following the procedure described by Argraves et al., J. Cell Biol. 105, 1183–1190 (1987) which is incorporated herein by reference.

Determination and Analysis of cDNA Sequences

Two cDNA clones, designated 271 and 225, with inserts of 3.6 and 1.7 kilobases, respectively, were selected for sequencing. Multiple overlapping fragments were sequenced. Nonoverlapping fragments were sequenced in both directions. Alignment of the fragments that were cloned and sequenced is summarized in FIG. 1 (SEQ ID NO: 1). cDNA inserts were cleaved with various restriction enzymes, and fragments subcloned into either M13mp19(+) (Bethesda Research Laboratories, Gaithersburg, Md.) or Bluescript SK M13(+) (Stratagene Cloning Systems, La Jolla, Calif.). Nucleic acid sequencing was done by the dideoxy chain termination method of Sanger et al. using deoxyadenosine 5'-α-[$^{35}$S]thiophosphate (New England Nuclear, Boston, Mass.) and a kit from USB (Cleveland, Ohio). Some areas were sequenced using 15-base oligo-nucleotide primers synthesized using a DNA synthesizer (Applied Biosystems, Foster City, Calif.). Sequence analysis was done using the MicroGenie program (Beckman). Homology searches were carried out using Bionet with EMBL, Genbank, NBRF/PIR and Swiss-Prot databases.

The nucleic acid sequence of the cDNA revealed a 3.4-kilobase open reading frame followed by a 155-base-pair 3' untranslated region. The deduced amino acid sequence is shown in FIG. 1 (SEQ ID NO: 2). The NH$_2$-terminal amino acid sequence of fragments isolated from peptic or chymotryptic digests of placenta and the NH$_2$-terminal amino acid sequence of a 16-kDa fragment generated with thrombin were contained within the deduced sequence, thus defining the clones as merosin cDNA.

The deduced partial sequence of merosin comprises 1130 amino acids and contains 13 potential sites of N-glycosylation. The sequence includes five repeats of about 190 amino acids. These repeats contain a conserved 7-amino acid sequence, Leu-Phe-Val-Gly-Gly-Leu-Pro (SEQ ID NO: 21), or variations thereof (FIG. 1 SEQ ID NO: 2). This is followed 17–21 and 40–43 residues later by cysteines most of which are preceded by glycines. The average percentage of identity among the five repeats is about 25%.

Protein Sequencing

A 55 kD merosin fragment was isolated from a pepsin digest of human placenta using monoclonal antibody affinity chromatography as described in Leivo and Engvall, supra. The pepsin fragment of merosin was digested further with thrombin and a 16 kD fragment was selected for sequence analysis. The merosin fragments were electrophoretically separated on a 10 to 20% gradient polyacrylamide gel in the presence of NaDodSO$_4$, blotted onto polyvinylidene difluoride membranes (Millipore, Boston, MA) and sequenced on an Applied Biosystems sequenator as described by Matsudaira, J. Biol. Chem. 262 10035–10038 (1987) incorporated by reference herein.

Synthetic Peptides, Antibody Production, and Immunoblotting

The length of the open reading frame of the merosin cDNA indicated that the mature merosin polypeptide was much larger than the 80 kD fragment identified originally in placental extracts. The deduced amino acid sequence suggested that the 65 kD fragment and the 80 kD tissue polypeptide are COOH-terminal fragments of merosin. The missing portion of the intact merosin polypeptide was identified after synthesizing two 13-amino acid long peptides from the part of the deduced amino acid presumed to be NH$_2$-terminal of the 80 kD fragment (residues 475–488 and 457–469 in FIG. 1 SEQ ID NO: 2). Two 13 amino acid long peptides CNNFGLDLKADDKI (SEQ ID NO: 22) and CSIVDIDTNQEENI (SEQ ID NO: 22) were synthesized based on amino acid sequences deduced from the cDNA sequence. The cysteine at the NH$_2$-terminus of these peptides was added to facilitate coupling to carrier protein. The peptides were coupled to keyhole limpet hemocyanin using m-maleimidobenzoyl-N-hydroxysuccinimide ester (Pierce Chemical Co., Rockford, Ill.) according to O'Sullivan et al. (Anal. Biochem 100, 100–108 (1979) incorporated by reference herein. The resulting conjugates were emulsified in Freund's complete adjuvant and injected into rabbits. Boosting immunizations of the conjugate in Freund's incomplete adjuvant were provided one and two months later.

The dose of each injection was equivalent to 0.6 mg of peptide. Blood was collected 10 days after the third injection. The antisera obtained were tested against the glutaraldehyde-cross linked peptides in ELISA and against NaDodSO$_4$ extracts of tissue and isolated proteins in immunoblotting as described in Leivo and Engvall, supra.

Immunization of rabbits with these peptides resulted in antisera which, in immunoblotting, stained a polypeptide of about 300 kD in NaDodSO$_4$-extracts of placenta. This anti-peptide antisera did not react with the 80 kD or the 65 kD COOH-terminal fragments of merosin. The presence of the 80 kD fragment in the same extract was revealed by a monoclonal antibody (FIG. 3B, lane 1). Antibodies affinity purified from the anti-peptide antiserum on immobilized peptide also stained the 300 kD band. The other peptide antiserum and preimmune sera did not give any staining in immunoblotting. These results suggest that the merosin polypeptide is processed into two fragments of approximately 300 kD and 80 kD, respectively.

Isolation of Intact Merosin from Placenta

Merosin was then isolated using methods previously employed in the isolation of laminin from mouse tissues, Paulsson et al., Eur. J. Biochem, 166:11–19 (1987) incorporated by reference herein. These methods are based on the selective solubilization of laminin from basement membranes with EDTA-containing buffers. When human placenta was sequentially extracted with a neutral buffer and with the same buffer containing EDTA, merosin antigenic activity was found mainly in the EDTA extract. Merosin could be precipitated from the extract with either 4M NaCl or 40% saturated ammonium sulphate. Upon gel filtration on Sepharose 6B, merosin antigenic activity eluted in the void volume peak. It bound to DEAE cellulose and was eluted at about 0.2M NaCl.

FIG. 4 shows NaDodSO$_4$-polyacrylamide gel electrophoresis, electron microscopy after rotary shadowing, and ELISA analysis of the peak merosin-containing fraction from DEAE-cellulose chromatography. The predominant component in this fraction had a molecular weight of about 700 kD, slightly smaller than the 800 kD rat laminin, as determined by gel electrophoresis (FIG. 4A). After reduction with mercaptoethanol, the merosin fraction contained polypeptides of about 600 kD, 300 kD, and 180–200 kD in addition to some minor components of 60–90 kD (FIG. 4A). The synthetic peptide antiserum bound to the 500–600 kD and 300 kD bands in immunoblotting. Antibodies against the COOH-terminal fragment of merosin bound to an 80 kD band.

Electron microscopy after rotary shadowing was used to further characterize the merosin fraction. Cross-shaped images strongly resembling mouse and rat laminin were the predominant structures seen (FIG. 4B).

Analysis of the fraction by ELISA with merosin-specific and laminin subunit-specific monoclonal antibodies showed that the preparation contained the merosin polypeptide and the laminin BI and B2 light chains. No reactivity was obtained with laminin heavy chain-specific antibodies (FIG. 4C). The truncated pepsin fragment of laminin, isolated with laminin heavy chain-specific monoclonal antibody, reacted with antibodies specific for the heavy chain as well as with antibodies specific for the B1 and B2 chains. This laminin preparation did not react with merosin antibodies (FIG. 4C). These results show that the high molecular weight, laminin-like molecule isolated from EDTA-extracts of placenta contained no detectable laminin heavy chain but contained laminin light chains associated with the merosin heavy chain.

EXAMPLE II

Merosin Activity

Merosin Promotes Cell Attachment

Cell attachment promotion by merosin was determined by methods well known in the art and set forth in Engvall and Ruoslahti, Collagen Rel. Res., 3:359–369 (1983) hereby incorporated by reference. Briefly, polystyrene microtiter plates (Flow Laboratories, Irvine, Calif.) were coated with various proteins by incubating the wells with 100 μl of different concentrations of the protein in PBS for 3–16 h at room temperature. Nonbound protein was removed by three washes in PBS. In some experiments, the wells with protein solution were air dried at 37° C. and then washed. Cells were trypsinized and washed twice with 0.5 mg/ml soy bean trypsin inhibitor in EMEM. A suspension of approximately 250,000 cells per ml EMEM with 10 mM HEPES was prepared and 0.1 ml was added to each well already containing 0.1 ml EMEM. The plate was then incubated at 37° C. for 30–90 min in an atmosphere of 10% $CO_2$ in air. Cell attachment was evaluated by one or more of the following methods: 1) Nonattached cells were removed and counted; 2) attached cells were fixed, stained with toluidine blue, and counted using an Artek cell counter (Dynatech Corporation, Alexandria, Va.); or 3) the light absorbed by the fixed and stained cells was measured using an automatic ELISA reader (Multiscan, Flow Laboratories). When laminin was tested in solution, it was serially diluted in the plate with a solution of 1 mg/ml BSA in EMEM containing 10 mM HEPES before adding the cells. All assays were done with samples in triplicates.

The cell lines in Table 1 have been tested for cell attachment to merosin. Successful attachment is indicated as a "+." The better the attachment the more "+'s."

TABLE 1

| | Degree of Attachment | |
| Cell Line | Merosin | Laminin |
| --- | --- | --- |
| JAR, Chonocarcinoma | – | ++ |
| Endothelial Cells | – | +++ |
| SKLMS, Muscle | ++ | +++ |
| MG63, Osteosarcoma | +++ | +++ |
| U251, Glioma | +++ | +++ |
| JMR 32, Neuroblastoma | +++ | +++ |

The results show that merosin promotes attachment by many but not all types of cells.

Merosin Promotes Neurite Outgrowth

Neurite promoting activity by merosin was determined by known methods as set forth in Engvall et al., J. Cell Biol., 103:2457–2465 (1986) and Manthorpe et al., A Dissection and Tissue Culture, Manual of the Nervous System, 322–326 (1989), Alan R. Liss, Inc., both of which are hereby incorporated by reference. Briefly, embryonic day 8 chick ciliary ganglion neuronal cultures were used. Polyornithine-coated tissue culture plastic wells (6-mm diameter, 96-well microplates) were treated with 5 μg/ml of human laminin or merosin in PBS for 2–3 h at 37° C. The wells were washed once with 100 μl PBS containing 1% BSA. 100 μl culture medium (Dulbecco's modified Eagle's basal medium supplemented with 0.5% BSA, $8 \times 10^{-7}$M insulin, $3.3 \times 10^{-2}$M glucose, $2.6 \times 10^{-2}$M $NaHCO_3$, $2 \times 10^{-3}$M L-glutamine, 100 μm/ml penicillin, and 100 trophic units/ml ciliary neuronotrophic factor) containing 1,000 neurons was added. Cultures were fixed after 3 h by the addition of 200 μl 2% glutaraldehyde for 20 min., washed with water, and stained with 0.1% toluidine blue in water. About 150 neurons were observed microscopically for each culture condition. Neurons were recorded as neurite-bearing if they possessed at least 50 μm of total neurite length.

In addition, surfaces were coated with 100 μg/ml polyoruithine (PORN) for attachment. 25 μg/ml laminin or merosin were then added for neurite outgrowth. Cells were allowed to extend neurites for 72 hours. The degree of promotion is set forth in table 2. Promotion of neurite growth is indicated as a "+." The greater the promotion, the more "+'s."

TABLE 2

| | No Protein | Laminin | Merosin |
| --- | --- | --- | --- |
| No Porn | – | – | – |
| Porn | + | +++ | +++ |

The results show merosin is a promotor of neurite outgrowth and, as such, is as efficient as laminin. This suggests that for certain applications (clinical) merosin would be better than laminin for nerve regeneration because it may not have e.g. angiogenic activity.

EXAMPLE III

Merosin Distribution in Human Schwann Cell Neoplasms

The expression of the basement membrane proteins merosin and laminin was studied immunohistochemically in a series of benign and malignant schwannomas and plexiform neurofibromas. Fresh tissue samples were frozen in liquid nitrogen. Monoclonal antibodies to merosin and laminin were applies to frozen sections, and indirect immunoperoxidase or indirect immunofluorescence techniques were used to detect the two proteins in tissues. The results are described in Leivo et al., Laboratory Investigation, 61:426–432 (1989). This reference and the references cited therein are hereby incorporated by reference.

Tissue Material

Human neurogenic tumors were obtained fresh without fixation at the Department of Pathology, University of Helsinki. In one instance tissue was derived from the autopsy of a patient with von Recklinghausen's disease who died of a buccal malignant schwannoma. The tissue samples were frozen in liquid nitrogen and embedded in Tissue-Tek OCT (Miles, Naperville, Ill.). The frozen sections were air-dried for 1–2 hours and fixed in acetone. Part of each tissue sample was fixed in formalin and embedded in paraffin for conventional histologic evaluation using hematoxylin-eosin.

Antibodies

Monoclonal antibodies raised to the reduced and alkylated 65-kD polypeptide fragment of merosin were used. These antibodies detect denatured human merosin, and they blotted an 80-kD polypeptide band in sodium dodecyl sulfate extracts of human placenta. The following clones of these antibodies giving identical staining results were used: 5H2, 4E10, 2G9, 4H2, 1F6, 2E10, and 2D10. Staining results identical to those obtained with monoclonal antibodies have also been obtained in normal tissues with a polyclonal antiserum to merosin. Monoclonal antibodies to nearly intact human laminin have been described, Engvall et al. supra. The monoclonal antibody 2E8 that blots the 200-kD B1 chain of laminin transferred from sodium dodecyl sulfate-polyacrylamide gels was used.

In immunohistochemical characterization of the Schwann cell tumors, we used a polyclonal rabbit antibody to bovine S-100 protein (Dakopatts, Glostrup, Denmark) at 1:300 dilution and a monoclonal antibody to glial fibrillary acidic protein (Labsystems, Helsinki, Finland) at 1:30 dilution.

Immunohistochemistry

Frozen sections were treated with hybridoma culture media at 1:2–1:5 dilution. The primary mouse antibodies were applied on sections for 30 minutes or overnight, followed by a 30-minute incubation with biotinylated rabbit antimouse IgG anti-serum (Dako, Copenhagen, Denmark) at 1:500 dilution. Finally, the bound biotin was detected with avidin combined in vitro with biotinylated peroxidase (AB Complex, Dakopatts), both diluted at 1:160. The color was developed with 3-amino-9-ethylcarbazole (Sigma, St. Louis, Mo.) supplemented with 0.02% hydrogen peroxide. In some cases, fluorescein isothiocyanate-coupled goat antimouse IgG (Bio-Rad, Richmond, Calif.) was used to detect bound primary antibodies in indirect immunofluorescence.

For controls of specificity for the staining of merosin, normal mouse serum (1:10) or phosphate-buffered saline were used instead of the hybridoma medium. Controls of specificity for the staining of laminin by monoclonal antibodies have been documented. No significant staining was observed in control experiments. The preparations stained with the immunoperoxidase technique were lightly counterstained with Mayer's hemalum (Merck, Darmstadt, West Germany) to show nuclei. Immunoperoxidase stainings and immunofluorescence preparations were observed and photographed in a Zeiss Axiophot microscope equipped for epi-illumination.

Four human schwannomas, two plexiform neurofibromas, and four malignant schwannomas were examined. Two schwannomas were retroperitoneal; one was mediastinal, and one was from the gastric wall exhibiting the histological features of gastric schwannomas. Histologically, all schwannomas showed a relatively uniform spindle cell morphology with focally palisading arrangement of nuclei. Two cases showed an alternating pattern of cellular and loose areas, representing the so-called Antoni A and Antoni B areas, respectively. Electron microscopic examination performed in three cases disclosed spindle cells rich in rough endoplasmic reticulum exhibiting multiple slender cell processes covered by prominent deposition of basement membrane material. These findings were compatible with the ultrastructural features of schwannomas. In immunohistological studies, all schwannomas were strongly positive for S-100 protein. Glial fibrillary acidic protein (GFAP) was focally seen in three cases.

Prominent staining for laminin was seen in parallel layers of basement membranes in the cellular areas and in the entire thickness of the walls of all blood vessels. The loose, less cellular areas of the tumors and the connective tissue sheaths around vessel walls contained no immunoreactive laminin. The cellular areas including the Verocay bodies contained no or only negligible amounts of merosin. However, distinct staining for merosin was regularly seen at the interface where the cellular areas bordered the loose stromal areas or where the cellular areas bordered vascular septa.

Plexiform Neurofibromas

Two plexiform neurofibromas were from nerve trunks of the subcutis of the back and the mediastinum of patients with von Recklinghausen's disease. These tumors represented enlarged tortuous nerve trunks containing wavy collagen and spindle cells compatible with Schwann cells and fibroblasts. In both tumors, merosin and laminin were colocalized in the form of linear immunoreactivity along basement membranes outlining the tortuous nerve fascicles. Laminin was also found in vessel walls. However, no merosin was seen in this location.

Malignant Schwannomas

These tumors originated from deep nerve trunks of femoral, retroperitoneal, and buccal tissues in patients with von Recklinghausen's disease. Histologically they represented malignant high grade spindle cell sarcomas with pronounced mitotic activity and focal areas of necrosis. The malignant schwannomas showed only minimal focal immunostaining for S-100 protein. No staining with antibody to GFAP was detected.

There was only minor focal staining for laminin in some perivascular tumor cells. All vessel walls were, however, strongly positive for laminin. Three of the four malignant schwannomas showed no immunostaining for merosin in the tumor cells. In contrast to laminin, only the external edges of vessel walls showed some staining. In sections where remnants of the original nerve trunks were microscopically identified, staining for merosin outlined the Schwann cell basement membranes of residual normal axons blending into merosin-negative tumor cell areas. A fibrous capsule surrounding malignant schwannomas was negative for merosin. However, in the adjacent striated muscle tissue, the basement membranes were positive for merosin. In one case, small but definite amounts of merosin were seen as punctate deposits between the tumor cells. In this case, a similar pattern of immunostaining for laminin was seen.

In brief, the distribution of merosin in schwannomas was more restricted than that of laminin, whereas in plexiform neurofibromas both proteins were present in the same location. No significant amounts of either protein were seen in malignant schwannomas.

In schwannomas, a strong staining for laminin was observed in basement membranes of the cellular Antoni A areas. In contrast, these areas were devoid of merosin. Immunoreactive merosin was seen at the border zone between tumor cells and vessel walls. The discordant distribution of the two basement membrane proteins in schwannomas differs from the situation in normal peripheral nerves where both the merosin and laminin are seen in the Schwann cell basement membranes. The reasons for this difference are unknown, but the result may reflect different biological roles for the two basement membrane proteins. Ultrastructurally, no apparent difference seems to exist between the neoplastic basement membranes of schwannomas and the normal basement membranes surrounding Schwann cells.

The presence of merosin only at the boundaries of the schwannoma cells and non-Schwann cell mesenchymal components demonstrates that the expression of merosin may be induced by a contact or an interaction of schwannoma cells with mesenchymal tissues or extracellular matrices and that no expression occurs by isolated schwannoma cells even in relatively well-differentiated tumors. Analogously, Schwann cells in peripheral nerves may require interactions with other cell types of the nerve fascicles such as the neurons, endoneurial fibroblasts, or perineurial cells for synthesis and/or deposition of merosin. It has been shown that the myelination and assembly of Schwann cell basal lamina in the developing nerve in vitro depend on interactions between the Schwann cell and neuron. Likewise, secretion of type IV collagen by cultured Schwann cells is modulated by a contact with neurons.

In plexiform neurofibromas, large amounts of both merosin and laminin were seen in an identical location. These neoplasms contain increased numbers of Schwann cells and perineurial cells as well as some residual axons contained within an intact perineurial sheath and enlarge the nerve fascicles. Thus, a relatively well-organized tissue architecture presumably essential for the expression of merosin is maintained. The presence of various cell elements within these nerve fascicles allows for many cellular contacts and interactions, and apparently some of these are essential for the secretion of merosin.

In the malignant schwannomas of this study, both merosin and laminin were absent or only minimally expressed. The concomitant lack of immunohistological markers for Schwann cell differentiation such as S-100 protein and GFAP suggests that these tumors are neurogenous sarcomas at a low level of Schwann cell differentiation.

Biosynthesis of laminin, type IV collagen, heparan sulfate proteoglycan, and entactin has been repeatedly shown in Schwann cell and schwannoma cell cultures. Moreover, in solid choriocarcinomas merosin was expressed by cells of the intermediate trophoblast type. No merosin could be detected in cultured choriocarcinoma cell lines, although these cell lines synthesized laminin. Apparently, cultured and neoplastic Schwann cells and other cells lose the capacity to secrete merosin but retain some other matrix proteins characteristic of the corresponding mature cells.

EXAMPLE IV

Isolation of cDNA Encoding Full Length Human Merosin

Generation and Characterization of cDNA Clones cDNA libraries were made from human placental poly(A) RNA. First, RNA was primed with primer ML-1 (nucleotide residues 6917–6942, FIG. 6) made according to the M chain (merosin) sequence in FIG. 1 and Ehrig et al., *Proc. Natl. Acad. Sci. USA* 87:3264–3268 (1990), incorporated herein by reference. The cDNA was prepared with a cDNA synthesis kit according to the manufacturer's instructions (Amersham International), purified and cloned into a λgt10 vector (Promega) using EcoRI/NotI adaptors (Pharmacia) and packaged using the Packagene extract system (Promega). Two other primer extension libraries were prepared similarly using primers M-10 (nucleotide residues 4153–4167, FIG. 6) and ML-5 (nucleotide residues 1028–1050, FIG. 6). The first library was screened using the previously characterized merosin cDNA (Example I and Ehrig et al., supra, incorporated herein by reference) as probe. The 5' end 1.4 kb EcoRI fragment of clone M1i-1 was used to screen the second extension library, and the third cDNA library was screened using a 1.3 kb NotI/AccI fragment of clone M10–22. To obtain clones for the 5' end of merosin, ML-6 (nucleotides 706–731, FIG. 6) primed cDNA was synthesized and EcoRI adaptors (Promega) were ligated to the cDNA. An EcoRI adapter primer and specific primers were used to amplify the 5' end of the cDNA by PCR. Purified cDNA clones and PCR products were subcloned into Bluescript II (Stratagene) and sequenced from both strands using dideoxy sequencing (Sanger et al., *Proc. Natl. Acad. Sci. USA* 84:935–939 (1977) hereby incorporated by reference).

Northern Analysis

Total RNA from 18–19 week-old human fetal tissues was isolated and samples containing 10 μg of each RNA were electrophoresed, transferred to a GeneScreen Plus filter and hybridized with human laminin A chain and merosin cDNA probes.

In situ Hybridization

To obtain sense and antisense probes for in situ hybridization a 260 bp NotI-SalI fragment from laminin A chain cDNA clone C2–12 and a 350 bp XhoI-ClaI fragment from merosin cDNA clone M1-1 were cloned into the Bluescript II vector. Probes were labeled with $^{35}$S-UTP (Amersham) using T3 and T7 polymerases. Human fetal tissues from the 17th gestational week were used. In situ hybridization was performed according to Cox et al., *Devl. Biol.* 101:485–502 (1984) and Wilkinson et al., *In: Postimplantation mammalian embryos: a practical approach* (A. J. Copp and D. L. Cockrof, eds.) IRL Press, Oxford 155–171 (1990), each of which is hereby incorporated by reference.

Characterization of cDNA Clones and Amino Acid Sequence of the Merosin Chain

A cDNA clone providing 1130 amino acid residues from the carboxyl terminal end of human merosin is described in Example 1, and by Ehrig et al., *Proc. Natl. Acad. Sci. USA* 87:3264–3268 (1990). This cDNA clone (MER 3') and its sequence were used for priming and screening of the first primer extension library. The longest positive 2.9 kb clone M1-1 (FIG. 5) was further characterized and its 5' end sequence was used to prime and screen the second primer extension library yielding clone M10–22 (3.2 kb). The 5' end of clone M10–22 was similarly used for screening of the third primer extension library resulting in the isolation of clone M5–1 (0.8 kb). Several libraries were made in order to obtain clones spanning the entire 5' end sequence. However, all clones obtained through those efforts were either of similar lengths or shorter than M5–1. Genomic clones that were characterized (data not shown) contained the putative exon 2, but not the coding region for the signal peptide and 5' untranslated region. The 5' end sequences were finally obtained by PCR amplification. The primer ML-6 was used to make cDNA to which EcoRI adaptors were ligated. An EcoRI adaptor primer and two specific primers were then used in PCR to amplify a 300 bp 5' end fragment, Mg-16 (FIG. 5), containing sequences for the 5' end untranslated region of the mRNA, the signal peptide and the amino-terminal end of merosin.

The nucleotide sequence (SEQ ID NO: 3) of the overlapping cDNA clones and the deduced amino acid sequence are shown in FIG. 6. The C-terminal end amino acid sequence described in Example I and in Ehrig et al., *Proc. Natl. Acad. Sci. USA* 87:3264–3268 (1990) is included in that sequence. The clones generated and characterized in this study covered a total of 6942 bp, consisting of a 49 bp 5' end untranslated region and 6893 bp of an open reading frame. The 5' end sequence has an open reading frame but the sequence ACUACGAUGC around the initiator methionine is in agreement with the Kozak consensus sequence for translation initiation (Kozak, M., *J. Cell. Biol.* 115:887–903 (1991) hereby incorporated by reference). The putative signal peptide contains 22 amino acids starting with the initiator methionine followed by a hydrophobic leucine-rich sequence. Computer program analysis predicting the signal peptidase cleavage site, based on the method of von Heijne (1986), incorporated here by reference, suggested a cleavage site after Ala22, whereby mature merosin would start with a glutamine residue as do most laminin chains. Altogether, merosin contains 3088 amino acid residues after cleavage of the tentative 22-residue signal peptide.

Domain Structure of Merosin Comparison with the Laminin A Chain Mature human merosin is 30 residues larger than the human laminin A chain which contains 3058 residues (Nissinen et al., *Biochem. J.* 276:369–379 (1991); Haaparanta et al., *Matrix* 11:151–160 (1991)). The amino acid sequences of both chains are aligned in FIG. 7 (SEQ ID NOs: 4 and 5). Similarly to all laminin chains, the merosin protein has distinct domains which are predicted to have globular regions, cysteine-rich rod-like regions and helical structures. Additionally, merosin, like the laminin A chain, has a large globular domain at the carboxy-terminal end (Ehrig et al., *Proc. Natl. Acad. Sci. USA* 87:3264–3268 (1990)). Comparison of the two sequences demonstrates that the domain structure of merosin is similar to that of the laminin A chain, and that these two laminin heavy chains have considerable homology.

The amino-terminal end domains VI (residues 23–286), IVb (residues 528–723) and IVa (residues 1176–1379) of merosin are predicted to form globular structures. Domains V (residues 287–527), IIIb (residues 724–1175) and IIIa (residues 1380–1573) contain cysteine-rich EGF-like repeats and are predicted to have rigid rod-like structures. The number of EGF-like repeats is identical in merosin and the laimin A chain. Domain V has four and one-half repeats, domain IIIb has ten and one-half, and domain IIIa has four repeats. Beck et al., *FASEB J.* 4:148–160 (1990) and Beck et al., In: W. Taylor and P. Argos, (eds) *Springer series in biophysics*, Springer-Verlag, Berlin 7:231–256 (1992) count the half repeats as one, and according to that both chains contain 17 cysteine-rich repeats. Domains I+II (residues 1574–2153), a part of which has previously been reported (Ehrig et al., Proc. Natl. Acad. Sci. USA 87:3264–3268 (1990)), participate together with two B-type chains in the formation of a triple coiled-coil structure that forms the long arm of the laminin molecule. In addition, merosin contains one cysteine residue in this region which has no counterpart in the laminin A chain or any of the B-type chains characterized thus far. The large carboxy-terminal G domain (residues 2154–3110) forms the large globule at the end of the long arm of the laminin molecule.

The amino-terminal domain VI in the M chain has 12, domain IVa two, domain IIIb one, domain I+II has 10 and domain G has seven amino acid residues more than the A chain. Domain V in the A chain has two residues more than the corresponding domain in the M chain. Comparison of the amino acid sequences of the human merosin (SEQ ID NO: 4) and laminin A (SEQ ID NO: 5) chain shows that the overall sequence similarity is 46.6% (Table 3) and 58.6% when conservative changes are included (FIG. 7). The sequence similarity is highest in the globular domains VI, or 73.9%, although this domain in merosin contains 12 residues more at the amino-terminus than the laminin A chain. If the additional glutamine rich amino-terminal sequence is excluded, the homology is 77.4%. All six cysteine sites in this domain are conserved. The amino acid sequence identities of the cysteine-rich domains V, IIIb and IIIa between merosin and laminin A chain are 60.1%, 54.9% and 50.2%, respectively. All cysteine residues in these domains are conserved and the length of domains are about the same. The globular domains IVb and IVa of the two chains also have approximately the same number of amino acids, although the sequence similarity is lower, or 42%. The sequence similarity is lowest between domains I+II where it is only 32.3%. There is also an extra cysteine residue (residue 1970) in domain I+II in merosin that has no counterpart in the laminin A chain. The sequence identity between domains G is 41.8%. There are 28 putative N-glycosylation sites in merosin and 34 in the laminin A chain, ten of these sites are conserved between the two chains. Most putative glycosylation sites are in domains G and I+II.

Chromosomal Assignment of Human Merosin Gene

The human merosin gene was mapped to chromosome 6 by hybridization of labeled cDNA clone M10–22 to DNA from a panel of 39 somatic cell hybrids. Hybridization of the merosin cDNA clone correlated with the distribution of chromosome 6. In situ hybridization of the cDNA to metaphase chromosomes confirmed the localization of the merosin gene to chromosome 6, and more precisely to bands 6q22→g23 (FIG. 8).

Expression of Merosin and Laminin A Chain Genes in Human Tissues

Expression of merosin and laminin A chain genes was compared by Northern hybridization using RNA from several 18–19-week-old human fetal tissues (FIG. 9). As previously reported (Nissinen et al., *Biochem. J.* 276:369–379 (1991)), the laminin A chain gene has highly restricted expression in human adult tissues. Signals for the laminin A chain were observed only in brain, neuroretina, kidney and testis, while no signals were obtained with RNA from skin, colon, pancreas, adrenal glands, cardiac muscle, lung, thymus, spleen, liver or calvarial bone, even after long exposures. The signal was by far the strongest in the neuroretina and in brain tissues the laminin A chain gene is expressed in the meninges, the intermediate zone, cerebellum, olfactory bulb and weak expression was observed also in choroid plexus and the ependymal zone.

The merosin protein has a different expression pattern, signals being observed with RNA from most tissues studied except thymus, liver, calvarial bone and ependymal and intermediate zones of brain. The strongest expression of the merosin gene was seen in cardiac muscle, pancreas, choroid plexus and meninges.

In situ Hybridization

Figure 10A:
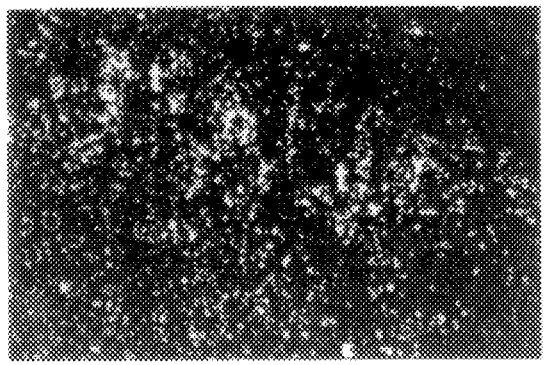
Figure 10B:
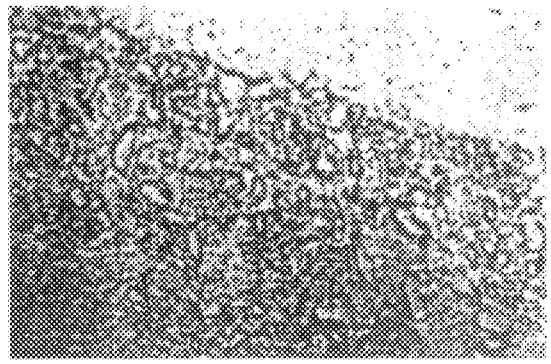
Figure 10C:
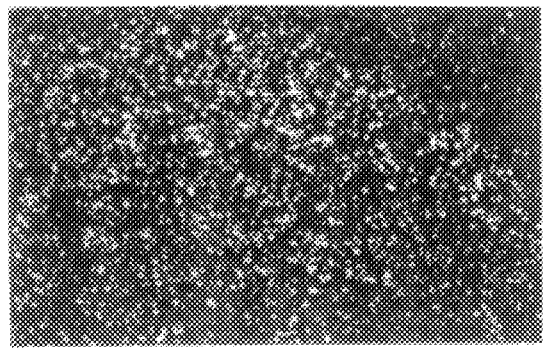
Figure 10D:
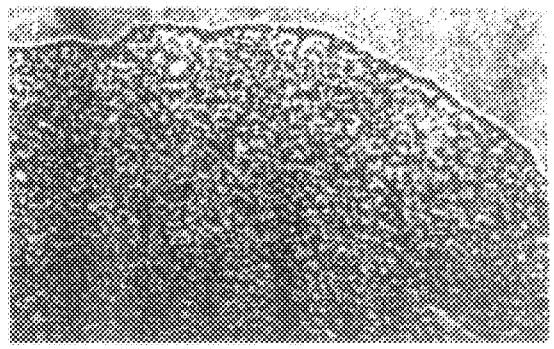
Figure 10E:
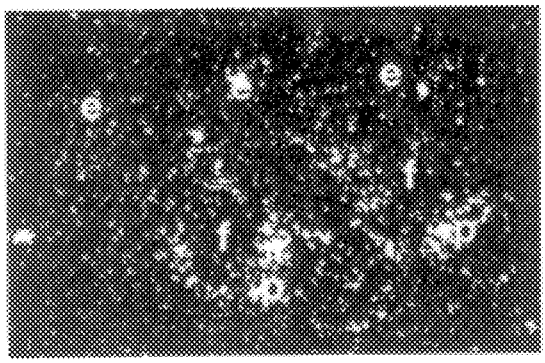
Figure 10F:
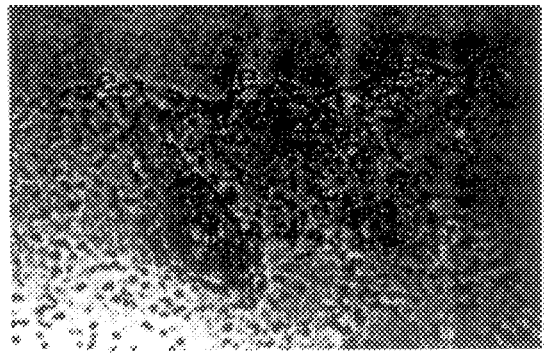
Figure 10G:
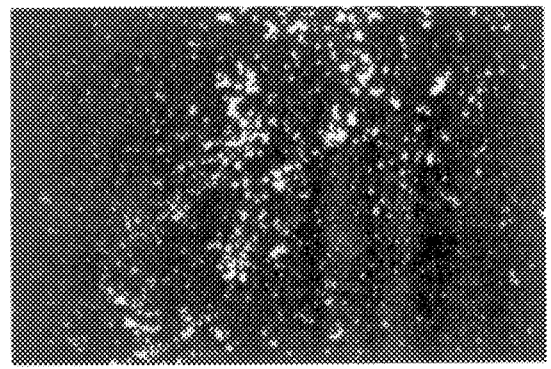
Figure 10H:
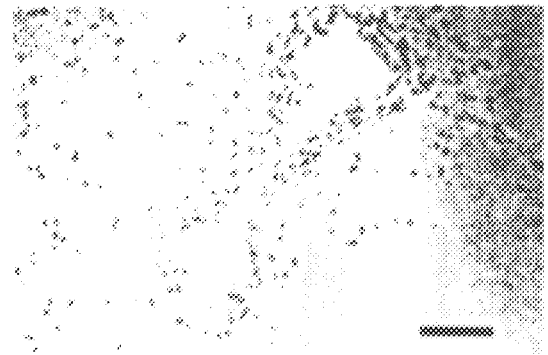

The location of merosin mRNA was analyzed by in situ hybridization in 17-week-old human fetal tissues. A cell-type-specific expression pattern for merosin mRNA was obvious in kidney, heart, skin and lung. In embryonic kidney, the transcripts for merosin were predominantly found in the undifferentiated nephrogenic mesenchyme of the outermost cortex (FIGS. 10A and 10B), whereas the nephric tubules and renal blood vessels remained negative. In heart muscle expression was observed in myocytes throughout the tissue (FIGS. 10C and 10D). The epidermal cells of the skin did not express merosin MRNA which, however, was abundant in the condensing mesenchyme around the tip of the developing hair follicles (FIGS. 10E and 10F). In the lung (FIGS. 10G and 10H) label was found in the smooth muscle cells of the pulmonary arteria, while the alveolar and bronchiolar cells were negative. Thus, the epithelial and endothelial cells were negative for merosin MRNA and the transcripts were found only in various mesenchymal cells. No cell specific signals were observed with the laminin A chain specific hybridizations in the tissues studied.

The present results, together with the 3' end sequence described in Example I and by Ehrig et al., *Proc. Natl. Acad. Sci. USA* 87:3264–3268 (1990), incorporated herein by reference, provide the complete primary structure for the human merosin. The merosin and laminin A chains were shown to be very similar. The overall sequence similarity between the two human chains (46.6%) is about the same as that between the homologous B1 and S chains. The human merosin and laminin chain genes have been localized to different chromosomes, with the exception of the genes for the closely related B2 and B2t which are located in the q25→q31 region of chromosome 1 (Fukushima et al., *Cytogen. Cell Genet.* 48:137–141 (1988). In this study, the merosin gene was assigned to 6q22→q23 while the related laminin A chain gene has been localized to chromosome 18p11.3 (Nagayoshi et al., *Genomics* 5:932–935 (1989)).

Domain Structure

The domain structure of merosin contains several features similar to other laminin chains and it is practically identical to that of the laminin A chain. The amino terminal globular domains VI share the highest homology, although merosin has additional 12 amino acids at the amino terminus. In fact, domain VI of all known human laminin chains, the mouse A chain, the rat S chain and the Drosophila A chain can be aligned so that the cysteine residues, some glycine, serine, proline and arginine residues, and short amino acid sequences RP, TCG and WWQS match in all chains (FIG. 11). A conserved sequence, Y(Y/F)Yxhxdhxh(G/R)G (h: hydrophobic residue, d: D, E or N) (according to Beck et al., In: W. Taylor and P. Argos, (eds) *Springer series in Biophysics*, Springer-Verlag, Berlin 7:231–256 (1992)), incorporated herein by reference, at the carboxyl terminus of domain VI also is found in merosin. The function of these conserved sequences is not known; but, while not wanting to be bound by any theory, the conserved regions can have significance for the role of this domain in laminin self-assembly which is apparently mediated by the amino terminal globular domains.

Domains V, IIIb and IIIa contain EGF-like repeats with eight cysteine residues at regular positions. The number of residues between the eighth to the second and the fifth to the seventh cysteine is the same in all laminin repeats and the order of repeats is specific. The number of repeats in merosin is 20 according to Sasaki et al., *J. Biol. Chem.* 263:16536–16544 (1988), incorporated herein by reference, or 17 according to Beck et al., *FASEB J.* 4:148–160 (1990); Beck et al., In: W. Taylor and P. Argos, (eds) *Springer series in biophysics*, Springer-Verlag, Berlin 7:231–256 (1992)), each incorporated herein by reference. The order of the repeats is conserved in human merosin and, generally, the repeats are very similar to the repeats present in human and mouse laminin A chains. The repeats in domain V of the human A (SEQ ID NO: 15), M (merosin) (SEQ ID NO: 17), B1 (SEQ ID NO: 13), B2 (SEQ ID NO: 18) and B2t (SEQ ID NO: 20) chains, the rat S chain (SEQ ID NO: 19), the murine A chain (SEQ ID NO: 14) and the Drosophila A chain (SEQ ID NO: 16) can be aligned in order (see FIG. 12). The human B2t chain lacks the first EGF-like repeat, but the rest of the repeats match with repeats of the other chains, except that after the second repeat there is an insertion making the distance between the eighth to the second cysteine longer than in the other chains. The alignment of domain V includes in addition to cysteine and glycine residues also other conserved sequences like HNT in first repeat between cysteines five and six. In contrast to other laminin chains, the Drosophila A chain contains 10 and a half EGF-like repeats in domain V. The two first cysteine-rich repeats in the Drosophila A chain can be aligned with repeats in the other chains but the rest of domain V differs more, although some similarities are found between repeats 3, 4, 5 and 6 in the Drosophila A chain and repeats 3, 4 and 5 in the other chains. All EGF-like repeats of known A-type chains can be aligned but this alignment is based mainly on conserved cysteines and glycines and the number of residues between them.

Globular domains IV of the A- and B2-type chains have been suggested to have evolved by an insertion between the third and fourth cysteines in one EGF-like repeat, and to be duplicated in A chains to form domains IVb and IVa. These domains are present in merosin and are, thus, well conserved in the laminin A-type chains, except for the Drosophila laminin A chain which contains only one domain IV. It also has another domain IV" that consists of duplicated sequences that are more similar to the Drosophila B1 chain domain IV.

Domains I+II form the long arm helical region. The EHS laminin chains have been shown to contain heptad repeats and similar repeats can be found also in the human laminin A chain and merosin. Proline residues are known to interrupt helices. There are four conserved proline residues in domain I+II in the mouse laminin A chain and the human laminin A chain and merosin. The cysteine pair that is suggested to form interchain disulfide bonds is conserved in merosin.

Domain G of merosin consists of five internal repeats that contain 107 to 178 amino acid residues (Ehrig et al., *Proc. Natl. Acad. Sci. USA* 87:3264–3268 (1990)), incorporated herein by reference. These repeats share 30 to 50% homology when compared with the human or mouse laminin A chain. The Drosophila laminin A chain also has five repeats in the G domain, but there is a large spacer sequence rich in threonine residues between subdomains G3 and G4 (Kusche-Gullberg et al., *EMBO J.* 11:4519–4527 (1992)). Several proteins are known to be homologous to the G domain in the laminin A chain and merosin. For example, one domain of the HSPG (heparin sulfate proteoglycan) core protein, perlecan, has 33% homology with the domain G of the human laminin A chain and merosin. Other homologous proteins are sex hormone binding globulin (Beck et al., In: W. Taylor and P. Argos, (eds) *Springer series in biophysics*, Springer-Verlag, Berlin 7:231–256 (1992)), androgen binding protein (Joseph et al., *FASEB J.* 6:2477–2481 (1992)) and neurexins (Ushkaryov et al., *Science* 257:50–56 (1992)), each of which is hereby incorporated by reference. Also Drosophila proteins fat, slit and crumbs share similarities with domain G of merosin and laminin A chain (Patthy, L., *FEBS Lett.* 298:182–184 (1992)).

TABLE I

Similarity of amino acid sequences of the human laminin Am and A chains as aligned in FIG. 3.

| Domain | Length of aligned sequence | Matches | Matches (conservative substitutions) | Un-matches | Matches % | Length |
|---|---|---|---|---|---|---|
| VI | 264 | 195 | 25 | 12 | 73.9 | (83.3) |
| V | 243 | 146 | 23 | 2 | 60.1 | (69.5) |
| IV-b | 199 | 85 | 28 | 6 | 42.7 | (56.8) |
| IIIb | 452 | 248 | 38 | 1 | 54.9 | (63.3) |
| IVa | 207 | 88 | 33 | 8 | 42.5 | (58.5) |
| IIIa | 195 | 98 | 14 | 2 | 50.2 | (57.4) |
| I + II | 591 | 191 | 79 | 32 | 32.3 | (45.7) |
| G | 987 | 413 | 136 | 67 | 41.8 | (55.6) |
| Total | 3138 | 1464 | 376 | 130 | 46.6 | (58.6) |

Expression of Merosin and Laminin A Chain in Human Fetal Tissues

Expression of the merosin gene was observed in many tissues known to contain the respective protein from immunohistological studies. However, the strong level of expression at an early embryonic stage contrasts previous immunostaining studies wherein merosin was not detected in the mouse embryo (Leivo et al., Proc. Natl. Acad. Sci. USA 85:1544–1548 (1988)). The reason for this discrepancy is obscure; but, while not intending to be bound by any theory, it could be due to some unknown limitation in the antibodies or the transcripts may not be efficiently translated into proteins. Merosin has been reported to appear in mouse muscle tissues first after birth (Leivo et al., Proc. Natl. Acad. Sci. USA 85:1544–1548 (1988)) and at adult stages also in some other tissues in several mammalian species (Sanes et al., J. Cell Biol. 111:1685–1699 (1990)). The data presented here on 17-week-old human fetal tissues revealed strong expression of the merosin gene in cardiac muscle, pancreas, choroid plexus and meninges, significant expression also being observed in testis, skin, adrenal glands, kidney, lung, spleen, neuroretina, olfactory bulbs and cerebellum. Practically no signals were observed in thymus, liver, bone or some brain tissues such as the intermediate and ependymal zones or cortical plates. The in situ hybridization analyses localized the expression of the merosin gene to myocytes of heart muscle, which agrees with several previous studies (Leivo et al., Proc. Natl. Acad. Sci. USA 85:1544–1548 (1988); Paulsson et al., J. Biol. Chem. 264:18726–18732 (1989); Klein et al., Development 110:823–837 (1990); Engvall et al., Cell Regul. 1:731–740 (1990); Paulsson et al., J. Biol. Chem. 266:17545–17551 (1991)). However, expression also was seen in stromal cells close to condensing mesenchyme in kidney and skin. Merosin has been localized by a monoclonal antibody to a narrow region located between the stromal cells and pretubular condensates in the outer cortex. A good concordance between merosin mRNA and protein expression also is seen in other embryonic tissues. The strong expression observed in mesenchymal cells located immediately beneath cells at the tip of the developing hair follicle and sebaceous glands indicates the potential role of merosin in exocrine gland development. Expression of merosin was not found in epithelial or endothelial cells of any of the tissues analyzed. Consequently, it can be concluded that during embryogenesis expression of merosin is primarily, if not only, the property of cells of mesenchyme origin.

Expression of the laminin A chain gene was shown to be considerably more restricted in human fetal tissues than that of the merosin gene. As previously reported for newborn human tissues (Nissinen et al., Biochem. J. 276:369–379 (1991)) Northern analysis revealed expression of the laminin A chain gene in kidney. The present studies did not locate the expression at this stage of kidney development to specific cells by in situ hybridizations. The laminin A chain has been localized in the kidney to tubular and glomerular basement membranes of adult tissues (Sanes et al., J. Cell Biol. 111:1685–1699 (1990)) and in polarized kidney epithelial cells (Holm et al., Cell Differ. 24:223–238 (1988); Klein et al., Cell 55:331–341 (1988); Ekblom et al., Cell 60:337–346 (1990). Klein et al., Development 110:823–837 (1990) reported the detection of laminin A chain mRNA in embryonic heart, liver, lung and intestine, and laminin containing the A chain has been isolated from skeletal and heart muscle, lung, liver, kidney and intestine (Paulsson et al., J. Biol. Chem. 264:18726–18732 (1989)). However, in this study on tissues from a 17-week-old human fetus, no signal for the A chain mRNA was observed in lung, heart or liver, even after long exposures. This discrepancy could be due to the differences in temporal expression during development. The intense expression of the laminin A chain gene in neuroretina, olfactory bulbs and cerebellum, is interesting and indicates its role in brain and nerve development. Detailed immunohistological and in situ hybridization analyses on developing brain tissues have been initiated to further analyze the temporal and spatial expression during brain development.

Several studies including the present study have demonstrated variability in both spatial and temporal expression of laminin subunit chains in vivo. This, in part, implicates tissue-specific functions of different laminin isoforms. With regard to merosin and the laminin A chain, Engvall et al., Cell Regul. 1:731–740 (1990) and Sanes et al., J. Cell Biol. 111:1685–1699 (1990), each incorporated herein by reference, showed that they are often mutually exclusive in a distinct type of basement membranes, suggesting that the laminin molecules contain either an M (merosin) or an A chain as a heavy chain. The present Northern blot and in situ hybridization analyses carried out on RNA from human fetal tissues supports the different tissue distribution of the M (merosin) and A chains. In particular, the results showed that the merosin gene is expressed in several tissues during embryonic development and possibly only by mesenchymal cells. However, the results also demonstrated that some laminin producing cells and tissues, such as skin and lung epithelia as well as vascular endothelia did not express either gene, or its expression was very weak in these tissues. This suggests that there exist laminin isoforms containing some, as yet, unidentified heavy A-type chains. Such isoforms may include kalinin or K-laminin.

Although the invention has been described with reference to the presently-preferred embodiment, it should be understood that various modifications can be made without departing from the spirit of the invention. Accordingly, the invention is limited only by the following claims.

What is claimed is:

1. An isolated nucleic acid molecule, comprising a nucleotide sequence encoding the contiguous amino acid sequence shown in FIG. 1 (SEQ ID NO.:2) or limited modifications to that sequence wherein cell attachment or neurite outgrowth is not destroyed.

2. A recombinant expression vector, comprising the nucleic acid molecule of claim 1.

3. A host-vector system, comprising a host cell containing the recombinant expression vector of claim 2.

4. The host-vector system of claim 3, wherein the host cell is a procaryotic cell.

5. The host-vector system of claim 4, wherein the procaryotic cell is an *Escherichia coli* cell.

6. The host-vector system of claim 3, wherein the host cell is a eukaryotic cell.

7. A cell culture, comprising the host cell of claim 4 or 6 and a suitable medium.

8. An isolated nucleic acid molecule, comprising the contiguous nucleic acid sequence set forth in FIG. 1 (SEQ ID NO:1).

9. A recombinant expression vector, comprising the nucleic acid molecule of claim 8.

10. A host-vector system, comprising a host cell containing the recombinant expression vector of claim 9.

11. The host-vector system of claim 10, wherein the host cell is a procaryotic cell.

12. The host-vector system of claim 11, wherein the procaryotic cell is an *Escherichia coli* cell.

13. The host-vector system of claim 10, wherein the host cell is a eukaryotic cell.

14. A cell culture, comprising the host cell of claim 11 or 13 and a suitable medium.

15. An isolated nucleic acid molecule, comprising a nucleic acid sequence encoding the contiguous amino acid sequence shown in FIG. 6 (SEQ ID NO.:4) or limited modifications to that sequence wherein cell attachment or neurite outgrowth is not destroyed.

16. The isolated nucleic acid molecule of claim 15, consisting of the nucleotide sequence encoding the amino acid sequence shown in FIG. 6 (SEQ ID NO: 4).

17. A recombinant expression vector, comprising the nucleic acid molecule of claim 15.

18. A host-vector system, comprising a host cell containing the recombinant expression vector of claim 17.

19. The host-vector system of claim 18, wherein the host cell is a procaryotic cell.

20. The host-vector system of claim 19, wherein the procaryotic cell is an *Escherichia coli* cell.

21. The host-vector system of claim 18, wherein the host cell is a eukaryotic cell.

22. A cell culture, comprising the host cell of claim 19 or 21 and a suitable medium.

23. An isolated nucleic acid molecule, comprising the contiguous nucleic acid sequence set forth in FIG. 6 (SEQ ID NO:3).

24. A recombinant expression vector, comprising the nucleic acid molecule of claim 23.

25. A host-vector system, comprising a host cell containing the recombinant expression vector of claim 24.

26. The host-vector system of claim 25, wherein the host cell is a procaryotic cell.

27. The host-vector system of claim 26, wherein the procaryotic cell is an *Escherichia coli* cell.

28. The host-vector system of claim 25, wherein the host cell is a eukaryotic cell.

29. A cell culture, comprising the host cell of claim 26 or 28 and a suitable medium.

* * * * *